United States Patent
Ariey et al.

(10) Patent No.: US 11,732,312 B2
(45) Date of Patent: Aug. 22, 2023

(54) MOLECULAR MARKER OF PLASMODIUM FALCIPARUM ARTEMISININ RESISTANCE

(71) Applicants: INSTITUT PASTEUR, Paris (FR); INSTITUT PASTEUR DU CAMBODGE, Phnom Penh (KH); CENTRE NATIONAL DE LA RECHERCHE SCIENTIFIQUE, Paris (FR)

(72) Inventors: Frederic Ariey, Choisy le Roi (FR); Odile Puijalon, Issy les Moulineaux (FR); Didier Menard, Le Gavre (FR); Francoise Benoit-Vical, Castanet Tolosan (FR); Johann Beghain, Conflans Sainte-honorine (FR); Benoit Witkowski, Montauban (FR); Jean-Christophe Barale, Vanves (FR); Christiane Bouchier, Paris (FR); Nimol Khim, Kandal (KH)

(73) Assignees: INSTITUT PASTEUR, Paris (FR); CENTRE NATIONAL DE LA RECHERCHE SCIENTIFIQUE, Paris (FR); INSTITUT PASTEUR DU CAMBODGE, Phnom Penh (KH)

( * ) Notice: Subject to any disclaimer, the term of this patent is extended or adjusted under 35 U.S.C. 154(b) by 135 days.

(21) Appl. No.: 17/124,478

(22) Filed: Dec. 16, 2020

(65) Prior Publication Data
US 2021/0198755 A1    Jul. 1, 2021

Related U.S. Application Data

(62) Division of application No. 15/036,064, filed as application No. PCT/IB2014/002910 on Nov. 14, 2014, now Pat. No. 10,900,093.

(60) Provisional application No. 61/904,651, filed on Nov. 15, 2013, provisional application No. 62/062,439, filed on Oct. 10, 2014.

(51) Int. Cl.
*C12Q 1/6893* (2018.01)

(52) U.S. Cl.
CPC ...... *C12Q 1/6893* (2013.01); *C12Q 2600/118* (2013.01); *C12Q 2600/156* (2013.01); *C12Q 2600/158* (2013.01); *C12Q 2600/16* (2013.01); *G01N 2333/445* (2013.01); *Y02A 50/30* (2018.01)

(58) Field of Classification Search
CPC . C12Q 1/6892; Y02A 50/30; G01N 2333/445
See application file for complete search history.

(56) References Cited

FOREIGN PATENT DOCUMENTS

WO    2008/146938 A1    12/2008

OTHER PUBLICATIONS

Ariey et al., Nature, 2014, 505, 50-55.*
Bosman et al., Malaria Journal, 2014, 13, 1-9.*
S.Takala-Harrison et al: "Genetic loci associated with delayed clearance of Plasmodium falciparum following artemisinin treatment in Southeast Asia", Proceedings of the National Academy of Sciences, vol. 110, No. 1, Dec. 17, 2012 (Dec. 17, 2012), pp. 240-245.
Ibrahim Maman Laminou et al: "Field-based evidence of fast and global increase of Plasmodium falciparum drug-resistance by DNA-microarrays and PCR/RFLP in Niger", Malaria Journal, Biomed Central, London, GB, vol. 8, No. 1, Feb. 23, 2009 (Feb. 23, 2009), p. 32.
Arjen M Dondorp et al: "Artemisinin Resistance in Plasmodium falciparum Malaria", The New England Journal o f Medicine, Jul. 30, 2009 (Jul. 30, 2009), pp. 455-467.
Elizabetha.Ashleyetal: "Spread of Artemisinin Resistance i n Plasmodium falciparum Malaria", New England Journal of Medicine, vol. 371, No. 5, Jul. 31, 2014 (Jul. 31, 2014), pp. 411-423.
Frederic Ariey et al: "A molecular marker of artemisinin-resistant Plasmodium falciparum malaria", NATURE, vol. 505, No. 7481, Dec. 18, 2013 (Dec. 18, 2013), pp. 50-55.
Gardner M J et al: "Genomesequenceof Thehuman Malaria Parasite Plasmodium Falciparum", Nature, Nature Publishing Group, United Kingdom, vol. 419, Jan. 1, 2002 (Jan. 1, 2002), pp. 498-511.
Cheeseman I.H. et al.,: "A mayor genome region underlying artemisinin resistance in Malaria", SCIENCE, vol. 336, Apr. 6, 2012 (Apr. 6, 2012), pp. 79-82.
International Search Report, PCT/OB2014/002910, dated Apr. 28, 2015.
Gharbi M, Flegg JA, Pradines B, Berenger A, Ndiaye M, et al. (2013) Surveillance of Travellers: an Additional Tool for Tracking Antimalarial Drug Resistance in Endemic Countries PLoS ONE 8(10): e77775.
Standwell C. Nkhoma, et al., "Genetic Evaluation of the Performance of Malaria Parasite Clearance Rate Metrics," The Journal of Infectious Diseases, 2013; 208: 346-50.
Van Schalkwyk et al., "Culture-adapted Plasmodium falciparum isolates from UK travellers: in vitro drug sensitivity, clonality and drug resistance markers," Malaria Journal 2013, 12:320.
Bosman et al., Malaria Journal, 2014, 13, 1-17.
Mahon et al., Malaria Journal, 2014, 431/1-431/6.
AL844509, 2009, https://www.ncbi.nlm.nih.gov/nuccore/AL844509.

(Continued)

*Primary Examiner* — Sun Jae Yoo
(74) *Attorney, Agent, or Firm* — Arrigo, Lee, Guttman & Mouta-Bellum LLP

(57) ABSTRACT

K13-propeller polymorphism is a useful molecular marker for tracking the emergence and spread of ART-resistant *P. falciparum*. The invention encompasses methods, compositions, and kits for detecting and genotyping *Plasmodium*, for example, *Plasmodium falciparum*. The methods, compositions, and kits can be used to detect the presence or absence of a mutated K-13 propeller nucleic acid or protein in the sample.

14 Claims, 31 Drawing Sheets

Specification includes a Sequence Listing.

(56) References Cited

OTHER PUBLICATIONS

Artermisinin Derivatives—2, 2018, htttps://www.pharmgkb.org/pathway/PA 165378192.
Artermisin—Wikipedia, 2018, https://en.wikipedia.org/wiki/Artemisinin.
Derivative, 2018, https://en .wikipedia.org/wiki/Derivative_(chemistry).
Plasmodium-falciparum-AL844509, 2009,https://www.ncbi.nlm.nih.gov/nuccore/AL844509.

* cited by examiner

```
F-XP_0013501S8    1  MEGEKVKTKANSISNFSMTYDRESGGNSNSDDKSGSSENDSNSEMNLTSDKNEKTENNSFLLANNSSYGNVKDSLLESID    80
V-XP_001614215    1  MEGEKIKS---NSISNFSVTYERESGANSNSDDKSGSSSENESNSFMNLTSDKNEKTENNSFILNNSSFANMKDSLLESID   78
C-XP_004223579    1  MEGEKIKT---NSISNFSVTYERESGANSNSDDKSGSSSENESNSFMNLTSDKNEKTENNSFILNNSSFANMKDSFLESID   78
K-XP_002259918    1  MEDEKIKS---NSISNFSVTYERESGANSNSDDKSVSSSENESNSFMNLTSDKNEKTENNSFILNNSSFANMKDSFLESID   78
B-XP_674094       1  MEDDKIKS---NSISNFSVTYERESGSNSNSEERDMSSDENESNLYMNLTGDKNEKIEDNS------SFVNIKDSLLESID   72
Y-XP_730901       1  MEDDKIKS---NSISNFSVTYERESGSNSNSEERDMSSDENESNLFMNLTGDKNEKIEDNS------SFVNMKDSLLESID   72
PCHAS_136130      1  MEDDKIKS---NSISNFSVTYERESGSNSNSEERDISSDENESNLFMNLTGDKNEKIEDNS------SFVNMKDSLLESID   72

F-XP_0013501S8   81  MSVLDSNFDSKKDFLPSNLSRUFNNMSKDNIGNKYLNKLLNKKKDTITNENNN         INENNNNNNLTANNIT[12]IMNT  165
V-XP_001614215   79  LSVLDSNFDSKKDFLPSNLSKNFNNLSKENLGNKYLNKLLNKSDSMFMSKGKD         MNLMENN--LGSNNLP   VKSS   149
C-XP_004223579   79  LSVLDSNFDSKKDFLPSNLSKNFNNLSKENLGNKYLNKLLNKSDSIFMSKSKD         MNLIENN--LGSNNLP   VKSS   149
K-XP_002259918   79  LSILDSNFDSKKDFLPSNLSKNFNNLSKENLGNKYLNKLLNKSDSLFMSKNKD         MNLMDNN--MGSNNLP   VKSS   149
B-XP_674094      73  LSVLDSNFDSKNDFLPNNFSKNLNNINNKYLNKYLNKNDSAFMAMNKD[8]LNVSNNN--LNGNNIV[22]GAPT          173
Y-XP_730901      73  LSVLDSNFDSKNDFLPNNFSKNLNNITKDNISNKYLNKYLNKNDSAFMTMSKD[8]LNVSNNN--LNGNNIV[22]GAPT     173
PCHAS_136130     73  LSVLDSNFDSKNDFLPNNFSKNLNNLTKDTIGNKYLSKYLNKNDPAFMAMAKD[8]LNVSNNN---INGNNIV[22]GAPA   173

F-XP_0013501S8  166  NKKENFLDA-ANLIN--DDSG-LNNLKEFSTVNNVNDTYEKKIIETELSDASDFENMVGDLRITFINWLKKTQMNFIREK    241
V-XP_001614215  150  NKKEGFMDS-STPINANEDNA-MNNLKKYSNANNINDTYEKKIIETELSDSSDFENMVGDLRITFINWLKKTQMNFIREK    227
C-XP_004223579  150  NKKEGFMDS-STPINANEDNA-MNNRKKYSNSNNINDTYEKKIIETELSDSSDFENMVGDLRITFINWLKKTQMNFIREK    227
K-XP_002259918  150  NKKEGFMDS-STPINANEDNA-MNNLKKYSNTNNINDTYEKKIIETELSDSSDFENMVGDLRITFINWLKKTQMNFIREK    227
B-XP_674094     174  NKKEIFMDSGASSINMNEDNSTMHNIRIYKNTNNINDTYEKKIIETELSDSSDFENMVGDLRITFINWLKKTQMNFIREK    253
Y-XP_730901     174  NKKEIFMDSGASSINMNEDNSTMHNIRIYKNTMNINDTYEKKIIETELSDSSDFENMVGDLRITFINWLKKTQMNFIREK    253
PCHAS_136130    174  NKKEMFMDSGASSINMNDDNTTMHNVRKYKSTNNVNDTYEKKIIETELSDSSDFENMVGDLRITFINWLKKTQMNFIREK    253

F-XP_0013501S8  242  DKLFKDKKELEMEKVRLYKELENRKNIEEQKLHADERKKLDIDISNGYKDKKEKEEHRKRFDEERLRFLQEIDKIKLVLY    321
V-XP_001614215  228  DKLFKDKKELEMERIRLYKEIENRKSIEEQKLHDERKKLDIDISNGYKQIKKEKEEHRKRFDEERLRFLQEIDKIKLVLY    307
C-XP_004223579  228  DKLFKDKKELEMERIRLYKEIENRKSIEEQKLHDERKKLDIDISNGYKQIKKEKEEHRKRFDEERLRFLQEIDKIKLVLY    307
K-XP_002259918  228  DKLFKDKKELEMERIRLYKEIENRKSIEEQKLHDERKKLDIDISNGYKQIKKEKEEHRKRFDEERLRFLQEIDKIKLVLY    307
B-XP_674094     254  DKLFKDKKELEMERIRLYKEIENRKAIEEQKLQDERKKLDIDISNGYKQIKKEKEHRKRFDDERLRFLQEIDKIKLVLY    333
Y-XP_730901     254  DKLFKDKKELEMERIRLYKEIENRKAIEEQKLQDERKKLDIDISNGYKQIKKEKEHRKRFDDERLRFLQEIDKIKLVLY    333
PCHAS_136130    254  EKLFKDKKELEMERIRLYKEIENRKNIEEQKLQDERKKLDIDISNGYKQIKKEKEHRKRFDDERLRFLQEIDKIKLVLY    333
```

*FIG. 10A*

```
F-XP_001350158   322  LEKEKYFQEYKNFENDKKKIVDANIATETMIDINVGGAIFETSRHTLTQQKDSFIEKLLSGRHHVTRDKQGRIFLDRDSE  401
V-XP_001614215   308  LEKEKYFQEYKNFENDKKKIVDANIATETMIDINVGGAIFETSRHTLTQQKDSFIEKLLSGRYHVTRDKQGRIFLDRDSE  387
C-XP_004223579   308  LEKEKYFQEYKNFENDKKKIVDANIATETMIDINVGGAIFETSRHTLTQQKDSFIEKLLSGRYHVTRDKQGRIFLDRDSE  387
K-XP_002259918   308  LEKEKYFQEYKNFENDKKKIVDANIATETMIDINVGGAIFETSRHTLTQQKDSFIEKLLSGRYHVTRDKQGRIFLDRDSE  387
PBANKA_135670    334  LEKEKYFQEYKNFENDKKKIVDANIATETMIDINVGGALFETSRHTLTQQKDSFIEKLLSGRYHITRDKQGRIFLDRDSE  413
Y-XP_730901      334  LEKEKYFQEYKNFENDKKKIVDANIATETMIDINVGGALFETSRHTLTQQKDSFIEKLLSGRYHITRDKQGRIFLDRDSE  413
PCHAS_136130     334  LEKEKYFQEYKNFENDKKKIVDANIATETMIDINVGGALFETSRHTLTQQKDSFIEQLLSGRYHITRDKQGRIFLDRDSE  413

F-XP_001350158   402  LFRIILNFLRNPLTIPIPKDLSESEALLKEAEFYGIKFLFPPLVFCIQGFDGVEYLNSMELLDISQQCWRMCPMSTKKA  481
V-XP_001614215   388  LFRIILNFLRNPLTVPIPKDLSESEALLKEAEFYGIKFLFPPLVFCMGGFDGVEYLNSMELLDISQQCWRMCTPMSTKKA  467
C-XP_004223579   388  LFRIILNFLRNPLTVPIPKDLSESEALLKEAEFY--------VFCMGGFDGVEYLNSMELLDISQQCWRMCTPMSTKKA  458
K-XP_002259918   388  LFRIILNFLRNPLTVPIPKDLSESEALLKEAEFYGIKFLFPPLVFCMGGFDGVEYLNSMELLDISQQCWRMCTPMSTKKA  467
PBANKA_135670    414  LFRIILNFLRNPLTIPIPKDLGESEALLKEAEFYGIKFLFPPLVFSIGGFDGVEYLNSMELLDISQQCWRMCTPMSTKKA  493
Y-XP_730901      414  LFRIILNFLRNPLTIPIPKDLGESEALLKEAEFYGIKFLFPPLVFSIGGFDGVEYLNSMELLDISQQCWRMCTPMSTKKA  493
P CHAS_136130    414  LFRIILNFLRNPLTIPIPKDLGESEALLKEAEFYGIKFLFPPLVFCIGGFDGVEYLNSMELLDISQQCWRMCTPMSTKKA  493

F-XP_001350158   482  YFGSAVLNNFLYVFGGNNYDYKALFETEVYDRLRDVWYVSSNLNIPRRNNCGVTSNGRIYCIGGYDGSSIINVEAYDHR  561
V-XP_001614215   468  YFGSAVLNNFLYVFGGNNYDYKALFETEVYDRLRDTWFVSSNLNIPRRNNCGVTSNGRIYCIGGYDGSSIIPNVEAYDHR  547
C-XP_004223579   459  YFGSAVLNNFLYVFGGNNYDYKALFETEVYDRLRDTWFVSSNLNIPRRNNCGVTSNGRIYCIGGYDGSSIIPNVEAYDHR  538
K-XP_002259918   468  YFGSAVLNNFLYVFGGNNYDYKALFETEVYDRLRDTWFVSSNLNIPRRNNCGVTSNGRIYCIGGYDGSCIIPNVEAYDHR  547
PBANKA_135670    494  YFGSAVLNNFLYVFGGNNYDYKALFETEVYDRLRDTWFLSSNLNIPRRNNCGITSNGRIYCIGGYDGSSIIPNVEAYDHR  573
Y-XP_730901      494  YFGSAVLNNFLYVFGGNNYDYKALFETEVYDRLRDTWFLSSNLNIPRRNNCGITSNGRIYCIGGYDGSSIIPNVEAYDHR  573
PCHAS_136130     494  YFGSAVLNNFLYVFGGNNYDYKALFETEVYDRLRDTWFLSSNLNIPRRNNCGITSNGRIYCIGGYDGSSIIPNVEAYDHR  573

F-XP_001350158   562  MKAWVEIAPLNTPRSSAMCVAFDNKIYVIGGTNGERLNSIEVYEEKMNKWEQFPYALLEARSGAAFNYLNQIYVVGGID  641
V-XP_001614215   548  MKAWVEIAPLNTPRSSSMCVAFDNKIYVIGGTNGERLNSIEVYDEKMNKWEQFPYALLEARSSGAAFNYLNQIYVVGGID  627
C-XP_004223579   539  MKAWVEIAPLNTPRSSMCVAFDNKIYVIGGTNGERLNSIEVYDEKMNKWEQFPYALLEARSSGAAFNYLNQIYVVGGID  618
K-XP_002259918   548  MKAWVEIAPLNTPRSSSMCVAFDNKIYVIGGTNGERLNSIEVYDEKMNKWEQFPYALLEARSSGAAFNYLNQIYVVGGID  627
PBANKA_135670    574  MKAWIEVAPLNTPRSSAMCVAFDNKIYVVGGANGERLNSIEVYDEKMNKWENFPYALLEARSSGAAFNYLNQIYVVGGID  653
Y-XP_730901      574  MKAWIEVAPLNTPRSSAMCVAFDNKIYVVGGANGERLNSIEVYDEKMNKWENFPYALLEARSSGAAFNYLNQIYVVGGID  653
PCHAS_136130     574  MKAWIEVAPLNTPRSSAMCVAFDNKIYVIGGANGERLNSIEVYDEKMNKWEKFPYALLEARSSGAAFNYLNQIYVVGGID  653
```

*FIG. 10B*

```
F-XP_001350158  642  NEHNILDSVEQYQPFNKRWQFLNGVPEKKMNFGAATLSDSYIITGGENGEVLNSCHFFSPDTNEWQLGPSLLVPRFGHSV  721
V-XP_001614215  628  NEHNILDSVEQYQPFNKRWQFLNGVPEKKMNFGAATLSDSYIITGGENGDVLNSCHFFSPDTNEWQIGPSLLVPRFGHSV  707
C-XP_004223579  619  NEHNILDSVEQYQPFNKRWQFLNGVPEKKMNFGAATLSDSYIITGGENGDVLNSCHFFSPDTNEWQIGPSLLVPRFGHSV  698
K-XP_002259918  628  NEHNILDSVEQYQPFNKRWQFLNGVPEKKMNFGAATLSDSYIITGGENGDVLNSCHFFSPDTNEWQIGPSLLVPRFGHSV  707
PBANKA_135670   654  NEHNILESVEQYQPFNKRWQFLNGIPEKKMNFGATTLSDSYIITGGENGDVLNSCHFFSPDTNEWQIGPPLLVPRFGHSV  733
Y-XP_730901     654  NEHNILESVEQYQPFNKRWQFLNGIPEKKMNFGATTLSDSYIITGGENGDVLNSCHFFSPDTNEWQIGPSLLVPRFGHSV  733
PCHAS_136130    654  NEHNILESVEQYQPFNKRWQFLANGIFEKKMNFGATTLSDSYIITGGENGDVLNSCHFFSPDTNEWQIGPSLLVPRFGHSV 733

F-XP_001350158  722  LIANI  726
V-XP_001614215  708  LIANI  712
C-XP_004223579  699  LIANI  703
K-XP_002259918  708  LIANI  712
PBANKA_135670   734  LVANI  738
Y-XP_730901     734  LVANI  738
PCHAS_136130    734  LVANI  738
```

GCCTTGTGTTGAAAGAAGCAGAATTTTATGGTATTAAATTTTTACCATTCCCATTAGTATTTTTGTATAGGTGGATTTGATGGTGTAGAATATTTAAATT

CGATGGAATTATTAGATATTAGTCAACAATGCTGGCGTATGTGTACACCTATGTGTACCAAAAAAGCTTATTTTGGAAGTGCTGTATTGAATAATTT

CTTATACGTTTTTGGTAATAACTATGATTATATAAGGCTTTATTGAAACTGAGGTGTATGATCGTTTAAGAGATGTATGTTGTATGTTTCAAGTAAT

TTAAATATACCTAGAGAATAATTGTGTGTTACGTCAAATGGTAGAATTTATTGTATTGGGGATATGATGGCTCTTCTATTATACCGAATGTAG

AAGCATATGATCATCGTATGAAAGCATGGGTAGAGGTGGCACCTTTGAATACCCCCTAGATCATCAGCTATGTGTTGCTTTTGATAATAAAATTTA

TGTCATTGGGTGGAACTAATGGTGAGAGATTAAAATTCTATTGAAGTATATGAAGAAAAAATGAATAAGGAACAATTCCATATGCCTATTAGAA

GCTAGAAGTTCAGGAGCAGCTTTAATTACCTTAAATCAAATATGTTGTTGGAGGTATTGATAATGAACATATTAGATTCCGTTGAACAAT

ATCAACCATTTAATAAAAGATGGCAATTTCTAAATGGTGTACCAGAGAAAAATGAATTTGGAGCTGCCACATTGTCAGATTCTTATATAATTAC

AGGAGGAGAAATGGCGAAGTTCTAAATTCATGTCATTTCTTTTCACCAGATACAAATGAATGGCAGCTTGGC

*FIG. 12A*

PCR1 (SEQUENCE SIZE: 265)
AGGTGGATTTGATGGTGTAGAAT
CATACACCTCAGTTTCAAATAAAGC

PCR2 (SEQUENCE SIZE: 235)
AATTTCTTATACGTTTTGGTGGTAA
CTCTACCCATGCTTTCATACGAT

PCR3 (SEQUENCE SIZE: 204)
GGATATGATGGCTCTTCTATTATACCG
ACTTCAATAGAATTTAATCTCTCACCA

PCR4 (SEQUENCE SIZE: 231)
ATGTCATTGGTGGAACTAATGGT
TTAAATGGTTGATATTGTTCAACG

PCR5 (SEQUENCE SIZE: 279)
TTCAGGAGCAGCTTTTAATTACC
CTGGTGAAAAGAAATGACATGAA

PCR6 (SEQUENCE SIZE: 188)
CCTTGTTGAAAGAAGCAGAATTTT
ATTCAATACAGCAGTTCCAAATAA

| Targeted gene | Primer forward sequence | Primer reverse sequence |
|---|---|---|
| PF3D7_0110400 | 5'-ttgagttcttttccaataatggc-3' | 5'-tgatatatgtttgtaggagctgtgag-3' |
| PF3D7_0213400 | 5'-gtgaaaaggataataaattctatgcc-3' | 5'-tatctaccatatattctgattgtctc-3' |
| PF3D7_1115700 | 5'-agcaagaacgtttgtgtaaa-3' | 5'-gaattcttaatgtttgaagat-3' |
| PF3D7_1302100 | 5'-taatatgtaaagtgattatgtatatgc-3' | 5'-atgctagagaagtaaagagaagaaggg-3' |
| PF3D7_1343700 | 5'-agaagagccatcatatccccc-3' | 5'-agtggaagacatcatgtaaccag-3' |
| PF3D7_1459600 | 5'-atatgagtaaaatgtcaggtttgg-3' | 5'-tgctgtgtgattcatgggg-3' |
| PF3D7_1464500 | 5'-aaatagttgggcgtagctcag-3' | 5'-tatcacaattaagtgtatcacaacg-3' |

| Gene ID (Plasmodb 9.1) | Annotation | Chromosome / position mutated | Nucleotide positions in coding sequence | F32-TEM codon | Codon F32-ART5 lineage Drug pressure cycle # | | | | | Mutant codon |
|---|---|---|---|---|---|---|---|---|---|---|
| | | | | | Day 0 | 23 0.2 µM ART | 39 1.8 µM ART | 56 9 µM ART | 120 9 µM ART | |
| PF3D7_0110400 | DNA directed RNA polymerase 2 complex subunit, putative | 01/359452 | 173 | gAt | gAt | gAt | gTt | gTt | gTt | D56V |
| PF3D7_1343700 | kelch protein, called here K13 | 13/1725970 | 1428 | atG | atG | atG | atA | atA | atA | M476I |
| PF3D7_0213400 | protein kinase 7 (PK7) | 02/542525 02/542627 | 310 312 | GaA | GaA | GaA | GaA | GaA | TaG | E104stop |
| PF3D7_1115700 | cysteine proteinase falcipain 2a | 11/555578 | 208 | tCa | tCa | tCa | tCa | tGa | tGa | S69stop |
| PF3D7_1302100 | gamete antigen 27/25 (Pg27) | 13/121899 | 601 | Cca | Cca | Cca | Cca | Cca | Aca | P201T |
| PF3D7_1459600 | conserved Plasmodium membrane protein, unknown function | 14/2832240 | 895 | aGt | aGt | aAt | aAt | aAt | aAt | S299T |
| PF3D7_1464500 | conserved Plasmodium membrane protein, unknown function | 14/2613177 | 4886 | aAt | aAt | aAt | aAt | aAt | aGt | N1629S |

[a] 3D7-type sequence; the same codon sequence is also observed in the parental F32-Tanzania line.
[b] Artemisinin (ART) dose used for selection during the corresponding drug-pressure cycle.
[c] Genes found in the chromosomal location of top-ranked signatures of selection in Takala-Harrison et al.

PF3D7_0110400 (PFA0505c) is a two-exon gene that codes for the RNA Polymerase II subunit 9 (RPB9), a small integral Pol II subunit, which is highly conserved among eukaryotes. The yeast RPB9 ortholog has been shown to have a role in assuring the fidelity of transcription *in vivo*. Deletion of the gene results in error-prone transcription[52]. The protein has a predicted zinc-ribbon domain similar to the zinc-ribbon domain of TFIIS (RNA Polymerase II elongation factor) that contains the essential catalytic Asp-Glu dipeptide[53]. Very little is known about the protein in *Plasmodium* although the gene is expressed and the protein is present in blood-stage parasites (www.plasmodb.org). It is difficult to make any prediction on the possible phenotypic consequences of the D56V mutation, which is located in a *Plasmodium*-specific, well-conserved domain.

PF3D7_1343700 (PF13_0238) is a one-exon gene (called here K13) that codes for a putative kelch protein. K13 has a predicted 3-domain structure, with an approx. 225 residue-long, *Plasmodium*-specific and well conserved N-terminal domain, followed by a BTB/POZ domain and a 6-blade C-terminal propeller domain formed from canonical kelch motifs[43,48]. Little is known about the protein in malaria parasites. Proteomics data indicate that it is produced by asexual (merozoites, rings, trophozoites and schizonts) and sexual (gametocytes) blood-stages *P. falciparum* parasites, and that it possesses phosphorylated residues in the N-terminal *Plasmodium*-specific domain (www.plasmodb.org). The M476I mutation is located between the first and second blade of propeller domain.

PF3D7_0213400 (PFB0605w) is a four-exon gene that codes for protein kinase 7 (PK7) expressed in asexual blood-stage parasites, gametocytes and ookinetes. The E104 stop mutation (two SNPs affecting the same codon) observed in F32-ART5 interrupts the gene resulting in a truncated putative translation product lacking more than 2/3 of its sequence. Studies with genetically inactivated 3D7 parasites have shown that PK7-KO *P. falciparum* parasites have an asexual growth defect due to a reduced number of merozoites per schizont[51]. Furthermore, PK7 is important for mosquito transmission, with a collapsed number of ookinetes in PK7-KO *P. falciparum*[54] and PK7-KO *P. berghei*, where no sporoblasts and consequently no sporozoites are formed[55]. This transmission defective phenotype is unlikely to survive in the field.

PF3D7_1115700 (PF11_0165) is a one-exon gene that codes for falcipain 2a, a cysteine proteinase produced by maturing blood-stage parasites (trophozoites and schizonts) and involved in hemoglobin degradation[56]. The S69stop mutation located in the pro-enzyme region precludes expression of an active enzyme by F32-ART5 parasites. Gene inactivation has been shown to induce a transient reduction of hemoglobin degradation compensated by expression of other members of the cysteine proteinase family, with minimal impact on growth rate[57,58]. However, *falcipain 2a* is the only gene from the list of seven affected loci that has been associated with the *in vitro* response to artemisinin. Indeed, it has been convincingly shown that inhibition of falcipain2a-dependent hemoglobin digestion by specific inhibitors or by gene inactivation reduces parasite susceptibility to artemisinins[19]. Moreover, wildtype 3D7 ring stages that do not massively digest hemoglobin display a reduced susceptibility to artemisinins[39].

PF3D7_1302100 (PF13_0011) is a one-exon gene that codes for the gamete antigen 27/25 (Pfg27) produced at the onset of gametocytogenesis. The gene is specific to *P. falciparum* and its close relatives such as *P. reichenowi*. This is an abundant, dimeric phosphorylated cytoplasmic protein that binds RNA. The various KO lines generated display conflicting phenotypes with some *pfg27*KO 3D7 lines being deficient in gametocytogenesis[60] while other Pfg27-defective 3D7 lines undergo unimpaired gametocytogenesis up to mature stage V gametocytes and subsequently produce oocysts–although absence of Pfg27 is associated with abnormalities in the intracellular architecture of gametocytes[61]. The crystal structure shows that the protein forms a dimer, displays a particular RNA binding fold and possesses two Pro-X-X-Pro motifs (known ligands for various domains, including SH3 modules), which combine to form a receptacle for SH3 modules[62]. The P201T mutation is located in the C-terminal Pro-X-X-Pro motif and predicted to alter the spatial structure of the interaction domain and thus have functional consequences.

PF3D7_1459600 (PF14_0569) is a two-exon gene that codes for a 806 residue-long, conserved protein of unknown function. The *P. yoelii* ortholog has been annotated as the CAAT-box DNA binding subunit B. Close orthologs can be found only among the *Plasmodium* species. Proteomics data indicate that the protein is present in asexual (merozoites, rings, trophozoites and schizonts) and sexual (gametocytes) blood-stages of *P. falciparum* parasites. A predicted approx. 130 residue-long Interpro domain suggests the presence of an N-terminal multi-helical, alpha-alpha 2-layered structural VHS fold, possibly involved in intracellular membrane trafficking. The rest of the coding sequence has no specific domain signature. The S299T mutation is located in the "unknown" region.

PF3D7_1464500 (PF14_0603) is a five-exon gene that codes for a 3251 residue-long protein of unknown function, with 4 predicted trans-membrane domains, but otherwise no specific domain signature. Apart from proteomics data indicating its expression and phosphorylation in schizonts, with possible expression in gametocytes and sporozoites as well, little is known about its putative function. The N1629S mutation is located in the middle of the protein, with unpredictable phenotypic impact.

← FROM FIG. 16A

*FIG. 16B*

| Region | Province | Year of collection | | | | | | Total |
|---|---|---|---|---|---|---|---|---|
| | | 2001-2002 | 2003-2004 | 2005-2006 | 2007-2008 | 2009-2010 | 2011-2012 | |
| Western Cambodia | Battambang | 64 | 0 | 0 | 0 | 0 | 71 | 135 |
| | Pailin | 40 | 43 | 46 | 95 | 66 | 84 | 374 |
| | Pursat | 0 | 10 | 0 | 0 | 43 | 19 | 72 |
| Southern Cambodia | Kampot | 0 | 0 | 0 | 0 | 0 | 12 | 12 |
| | Kampong Som | 0 | 0 | 0 | 0 | 0 | 7 | 7 |
| Northern Cambodia | Oddar Meanchey | 0 | 0 | 0 | 0 | 0 | 33 | 33 |
| | Preah Vihear | 27 | 27 | 25 | 24 | 0 | 19 | 122 |
| Eastern Cambodia | Kratie | 15 | 0 | 0 | 0 | 0 | 17 | 32 |
| | Mondulkiri | 0 | 0 | 0 | 0 | 0 | 3 | 3 |
| | Ratanakiri | 56 | 30 | 22 | 0 | 8 | 35 | 151 |
| Total | | 202 | 110 | 93 | 119 | 117 | 300 | 941 |

| Codon position | Amino acid reference | Nucleotide reference | Amino acid mutation | Nucleotide mutation |
|---|---|---|---|---|
| 449 | G | Ggt | A | gCt |
| 458 | N | Aat | Y | Tat |
| 474 | T | Aca | T | aCa |
| 476* | M | Atg | I | atA |
| 481 | A | Gct | V | gTt |
| 493 | Y | Tac | Y | Tac |
| 508 | T | Act | T | aCt |
| 527 | P | Cct | T | Act |
| 533 | G | Ggt | S | Agt |
| 537 | N | Aat | I | aTt |
| 539 | R | Aga | T | aCa |
| 543 | I | Att | T | aCt |
| 553 | P | Ccg | L | cTg |
| 561 | R | Cgt | H | cAt |
| 568 | V | Gtg | G | gGg |
| 574 | P | Cct | L | cTt |
| 580 | C | Tgt | Y | tAt |
| 584 | D | Gat | V | gTt |
| 612† | E | Gaa | D | gaT |
| 623 | S | Agt | C | Tgt |

* observed in F32-ART5, not observed in Cambodia
† reported in The Gambia (ref 44), not observed in Cambodia

| KH group | Province | Mutations in the K13-propeller | | | | | Total |
|---|---|---|---|---|---|---|---|
| | | Wildtype | C580Y | R539T | Y493H | | |
| KH1 | Pursat | 7 | 0 | 0 | 2 | | 9 |
| | Ratanakiri | 46 | 0 | 0 | 0 | | 46 |
| KH2 | Pursat | 0 | 25 | 0 | 1 | | 26 |
| | Ratanakiri | 0 | 0 | 0 | 0 | | 0 |
| KH3 | Pursat | 3 | 7 | 4 | 0 | | 14 |
| | Ratanakiri | 0 | 0 | 0 | 0 | | 0 |
| KH4 | Pursat | 0 | 0 | 0 | 12 | | 12 |
| | Ratanakiri | 0 | 0 | 0 | 0 | | 0 |
| KHA | Pursat | 15 | 19 | 2 | 6 | | 42 |
| | Ratanakiri | 1 | 0 | 0 | 0 | | 1 |
| Total | | 72 | 51 | 6 | 21 | | 150 |

FIG. 19

| Mut | SNP | AFRICA | | ASIA | | Total | |
|---|---|---|---|---|---|---|---|
| 446 | F446I | | 0,0% | 42 | 5,4% | 4,8% | |
| 449 | G449A | 1 | 1,00% | 1 | 0,13% | 0,23% | |
| 458 | N458Y | | 0,0% | 7 | 0,9% | 0,8% | |
| 469 | C469Y | | 0,0% | 4 | 0,5% | 0,5% | |
| 470 | W470STOP | 1 | 1,00% | 1 | 0,13% | 0,23% | |
| 481 | A481V | | | 1 | 0,13% | 0,20% | detected in South America (n=1) |
| 493 | Y493H | 1 | 1,1% | 32 | 4,1% | 3,8% | |
| 503 | K503N | | 0,0% | 4 | 0,5% | 0,5% | |
| 522 | S522C | 5 | 5,3% | | 0,0% | 0,6% | |
| 534 | V534A | 3 | 3,2% | | 0,0% | 0,3% | |
| 539 | R539T | | 0,0% | 35 | 4,5% | 4,0% | |
| 543 | I543T | | 0,0% | 8 | 1,0% | 0,9% | |
| 548 | G548D | 2 | 2,1% | | 0,0% | 0,2% | |
| 553 | P553L | | 0,0% | 15 | 1,9% | 1,7% | |
| 555 | V555A | 3 | 3,2% | | 0,0% | 0,3% | |
| 557 | A557S | 2 | 2,1% | | 0,0% | 0,2% | |
| 561 | R561H | 1 | 1,00% | 1 | 0,13% | 0,23% | |
| 563 | K563R | 2 | 2,1% | | 0,0% | 0,2% | |
| 568 | V568G | | | 2 | 0,26% | 0,26% | |
| 574 | P574L | | 0,0% | 11 | 1,4% | 1,3% | |
| 578 | A578S | 21 | 22,1% | 1 | 0,1% | 2,5% | |
| 580 | C580Y | 1 | 1,1% | 591 | 75,9% | 67,7% | |
| 583 | F583L | 2 | 2,1% | | 0,0% | 0,2% | |
| 584 | D584V | | 0,0% | 3 | 0,4% | 0,3% | |
| 589 | V589I | 2 | 2,1% | | 0,0% | 0,2% | |
| 613 | Q613E | 2 | 2,1% | | 0,0% | 0,2% | |
| 641 | D641G | 2 | 2,1% | | 0,0% | 0,2% | |

*FIG. 20*

| Year | ID isolate | Sampling location (province) | Whole genome sequence[a] | RSA[0-3h,b] | PF3D7_ 0110400 | PF3D7_ 1343700 | PF3D7_ 0213400 | PF3D7_1115700 | PF3D7_ 1302100 | PF3D7_ 1459600 |
|---|---|---|---|---|---|---|---|---|---|---|
| N/A | 3D7 | N/A | Yes | 0.04 | WT | WT | WT | WT | WT | WT |
| 2011 | 4903 | Rattanakiri | Yes | 58 | WT | I543T | WT | WT | WT | 330Y |
| 2011 | 5019 | Oddar Meanchey | Yes | 11.6 | WT | C580Y | WT | 15H/51I/59F/255R/257E/343P/345G/414E | WT | WT |
| 2011 | 5268 | Pursat | Yes | 27.2 | WT | C580Y | WT | 228T/255R/257E/343P/345G/414E | WT | WT |
| 2010 | 3445 | Pailin | Yes | 27.3 | WT | C580Y | WT | 15H/51I/59F/255R/257E/353T/393I/400P/414E | WT | 330Y |
| 2011 | 4024 | Oddar Meanchey | Yes | 11.3 | WT | C580Y | WT | 228T/255R/257E/343P/345G | WT | WT |
| 2010 | 3630 | Pailin | Yes | 0.2 | WT | WT | WT | 228T/255R/257E/343P/345G | WT | WT |
| 2010 | 3504 | Pailin | Yes | 28.9 | WT | R539T | WT | 15H/51I/59F/197K/204K/255R/257E/343P /345G/414E | WT | 330Y |
| 2011 | 4507 | Oddar Meanchey | Yes | 5.8 | WT | R539T | WT | 228T/255R/257E/343P/345G/414E | WT | 330Y |
| 2011 | 4685 | Oddar Meanchey | Yes | 31.3 | WT | R539T | WT | 228T/255R/257E/343P/345G/414E | WT | 324H |
| 2011 | 4763 | Oddar Meanchey | Yes | 24.2 | WT | R539T | WT | 228T/255R/257E/343P/345G/414E | WT | WT |
| 2011 | 5333 | Kratie | Yes | 23.1 | WT | C580Y | WT | 228T/255R/257E/343P/345G | WT | 330Y |
| 2011 | 5457 | Kratie | Yes | 13.5 | WT | C580Y | WT | 228T/255R/257E/343P/345G | WT | WT |
| 2011 | 5529 | Kratie | Yes | 14.7 | WT | C580Y | WT | 228T/255R/257E/343P/345G | WT | 330Y |
| 2011 | 5540 | Kratie | Yes | 13.6 | WT | C580Y | WT | 228T/255R/257E/343P/345G | WT | WT |
| 2011 | 5560 | Kratie | Yes | 3.8 | WT | C580Y | WT | 228T/255R/257E/343P/345G | WT | 330Y |
| 2011 | 5693 | Kratie | Yes | 7.5 | WT | C580Y | WT | 228T/255R/257E/343P/345G | WT | 330Y |
| 2010 | 3629 | Pailin | Yes | 19.2 | WT | C580Y | WT | 228T/255R/257E/343P/345G | WT | 323N/326Y /327Y |
| 2011 | 5680 | Battambang | Yes | 12.6 | WT | C580Y | WT | 228T/255R/257E/343P/345G | WT | 323N/326Y |
| 2011 | 5131 | Pursat | Yes | 6.9 | WT | C580Y | WT | 228T/255R/257E/343P/345G | WT | WT |
| 2011 | 5269 | Pursat | Yes | 8.1 | WT | C580Y | WT | 228T/255R/257E/343P/345G | WT | 323N/326Y |
| 2010 | 3670 | Pailin | Yes | 19.2 | WT | WT | WT | 15H/51I/59F/255R/257E/353T/393I/400P/414E | WT | WT |
| 1992 | K1992 | Pailin | Yes | N/A | WT | WT | WT | 15H/51I/59F/255R/257E/393I/400P/414E | WT | WT |
| 1978 | 89F5 | Uganda | Yes | N/A | WT | WT | WT | 15H/51I/59F/255R/257E/343P/345G/414E | WT | 161K/204C |

| | | | | | | |
|---|---|---|---|---|---|---|
| 2011 5188 Rattanakiri | No | 0.09 | N/A | WT | N/A | N/A |
| 2011 4749 Oddar Meanchey | No | 0.15 | N/A | WT | N/A | N/A |
| 2011 5150 Rattanakiri | No | 0.16 | N/A | WT | N/A | N/A |
| 2012 6138 Pailin | No | 0.24 | N/A | WT | N/A | N/A |
| 2011 5211 Mondolkiri | No | 0.5 | N/A | WT | N/A | N/A |
| 2011 4208 Kampong Som | No | 0.51 | N/A | WT | N/A | N/A |
| 2010 3663 Pailin | No | 0.1 | N/A | WT | N/A | N/A |
| 2011 4248 Pailin | No | 13.5 | N/A | C580Y | N/A | N/A |
| 2010 3601 Pailin | No | 14.9 | N/A | R539T | 15H/5I/59F/197K/204K/255R/257E/343P /345G/414E | N/A |
| 2011 4914 Rattanakiri | No | 0.06 | N/A | WT | 15H/5I/59F/228T/255R/257E/343P/345G/414E | N/A |

FROM FIG. 21A

| PF3D7_1464500 |
|---|
| WT |
| 11N/479N/483N/490Y/768V/779D/1271N/2322Q/2399G/2418T/2571N/2825I |
| 11N/479N/483N/490Y/768V/779D/1271N/2322Q/2399G/2418T/2571N/2825I |
| 11N/179N/479N/483N/490Y/768V/779D/1271N/2322Q/2399G/2418T/2571N/2825I |
| 11N/179N/479N/483N/768V/779D/1271N/2322Q/2399G/2418T/2571N/2825I |
| 81H/179N/1271N/1650Y/1939D/1940D/1943D/1944D/2418T/2571N/2954R |
| 479N/483N/490Y/1271N/1373R/1939D/1940D/1943D/1944D/2322Q/2418T/2571N/2825I |
| 179N/479N/1271N/1705L/1939D/1940D/1943D/1944D/2418T/2571N/2617N/2637G |
| 179N/479N/1271N/1705L/1939D/1940D/1943D/1944D/2418T/2571N/2617N/2637G |
| 179N/479N/1271N/1705L/1939D/1940D/1943D/1944D/2418T/2571N/2617N/2637G |
| 179N/479N/1271N/1705L/1939D/1940D/1943D/1944D/2418T/2571N/2617N/2637G |
| 179N/479N/1271N/1705L/1939D/1940D/1943D/1944D/2418T/2571N/2617N/2637G |
| 179N/479N/1271N/1705L/1939D/1940D/1943D/1944D/2418T/2571N/2617N/2637G |
| 179N/479N/1271N/1705L/1939D/1940D/1943D/1944D/2418T/2571N/2617N/2637G |
| 179N/479N/1271N/1705L/1939D/1940D/1943D/1944D/2418T/2571N/2617N/2637G |
| 179N/479N/1271N/1705L/1939D/1940D/1943D/1944D/2418T/2571N/2617N/2637G |
| 179N/479N/1271N/1705L/1939D/1940D/1943D/1944D/2418T/2571N/2617N/2637G |
| 179N/479N/483N/1271N/1472Q/1519L/1939D/1940D/1943D/1944D/2571N |
| 179N/479N/483N/1271N/1472Q/1519L/1939D/1940D/1943D/1944D/2571N |
| 179N/479N/483N/490Y/1271N/1472Q/1519L/1939D/1940D/1943D/1944D/2571N |
| 179N/479N/483N/490Y/1271N/1472Q/1519L/1939D/1940D/1943D/1944D/2571N |
| 179N/479N/483N/1271N/1280N/1284N/1286D/1928N/1930D/1931E/1932H/1942D/2418T/2571N/2637G/2825I |
| 479N/483N/1271N/1277D/785N/779D/1271N/1277D/2397T/2418T/2571N/2825I |
| 11N/479N/483N/768V/1271N/1277D/1472Q/1939D/1940D/1939D/1940D/2288H/2571N/2594I/3206I |
| 479N/483N/490Y/1271N/1277D/1472Q/1939D/1940D/2288H/2571N/2594I/3206I |

↓ TO FIG. 22B

| | | | | | |
|---|---|---|---|---|---|
| 20125207 | Rattanakiri | No | 0.15 | N/A | WT |
| 20114974 | Rattanakiri | No | 0.18 | N/A | WT |
| 20114880 | Rattanakiri | No | 0.21 | N/A | WT |
| 20103592 | Rattanakiri | No | 0.32 | N/A | WT |
| 20114971 | Pailin | No | 18.3 | N/A | C580Y |
| 20103815 | Pailin | No | 23.6 | N/A | C580Y |
| 20115152 | Rattanakiri | No | 0.08 | N/A | WT |
| 20115055 | Rattanakiri | No | 0.12 | N/A | WT |
| 20115159 | Rattanakiri | No | 0.26 | N/A | WT |
| 20115208 | Pailin | No | 5.5 | N/A | C580Y |
| 20115100 | Pailin | No | 8.6 | N/A | C580Y |
| 20115035 | Pailin | No | 12.9 | N/A | C580Y |
| 20115145 | Pailin | No | 18.9 | N/A | C580Y |
| 20115168 | Pailin | No | 18.9 | N/A | C580Y |
| 20114970 | Pailin | No | 19.6 | N/A | C580Y |
| 20114992 | Pailin | No | 21.3 | N/A | C580Y |
| 20115160 | Pailin | No | 26.3 | N/A | C580Y |
| 20101009 | Pursat | No | 51.4 | N/A | Y493H |

[a]Yes (analysed by whole genome sequence), No (analysed by Sanger sequencing)
[b]RSA0-3h survival rates as described in ref 15
WT: wildtype (3D7 sequence)
N/A: Not available

| | | | |
|---|---|---|---|
| 15H/51I/59F/255R/257E/343P/345G/414E | N/A | N/A | N/A |
| 15H/51I/59F/255R/257E/343P/345G/414E | N/A | N/A | N/A |
| 15H/51I/59F/255R/257E/343P/345G/414E | N/A | N/A | N/A |
| 15H/51I/59F/255R/257E/343P/345G/414E | N/A | N/A | N/A |
| 15H/51I/59F/255R/257E/343P/345G/414E | N/A | N/A | N/A |
| 15H/51I/59F/255R/257E/393I/400P/414E | N/A | N/A | N/A |
| 15H/51I/59F/255R/257E/414E | N/A | N/A | N/A |
| 15H/51I/59F/255R/257E/414E | N/A | N/A | N/A |
| 15H/51I/59F/255R/257E/414E | N/A | N/A | N/A |
| 228T/255R/257E/343P/345G | N/A | N/A | N/A |
| 228T/255R/257E/343P/345G | N/A | N/A | N/A |
| 228T/255R/257E/343P/345G | N/A | N/A | N/A |
| 228T/255R/257E/343P/345G | N/A | N/A | N/A |
| 228T/255R/257E/343P/345G | N/A | N/A | N/A |
| 228T/255R/257E/343P/345G | N/A | N/A | N/A |
| 228T/255R/257E/343P/345G | N/A | N/A | N/A |
| 228T/255R/257E/343P/345G | N/A | N/A | N/A |
| 255R/257E/343P/345G | N/A | N/A | N/A |

FROM FIG. 23A

FIG. 23B

```
                        SEQUENCE LISTING

<160> NUMBER OF SEQ ID NOS: 134

<210> SEQ ID NO 1
<211> LENGTH: 2181
<212> TYPE: DNA
<213> ORGANISM: Plasmodium falciparum

<400> SEQUENCE: 1
atggaaggag aaaaagtaaa aacaaaagca aatagtatct cgaatttttc tatgacgtat      60
gatagggaat ctggtggtaa cagcaatagt gatgataaaa gcggaagtag tagcgagaat     120
gattctaatt catttatgaa tctaactagt gataaaaatg agaaaacgga aaataatagt     180
ttccttttaa ataatagtag ttatggaaat gttaaagata gcctattaga atccattgat     240
atgagtgtat tagattcgaa ctttgatagt aaaaaagatt ttttaccaag taatttatca     300
agaacattta ataatatgtc taaagataat ataggaaata aatatttaaa taaattgtta     360
```

```
aataaaaaaa aagatactat tacaaatgaa aataataata ttaatcataa taataataat       420
aataatctga cagcaaataa tataactaat aatcttatta ataataatat gaattctcca       480
tcaattatga ataccaacaa aaaagagaat tttttagatg cagcaaatct tataaatgat       540
gattctggat taaacaattt aaaaaaattt tcaactgtaa ataatgtaaa tgatacttat       600
gaaaagaaaa ttattgaaac ggaattaagt gatgctagtg attttgaaaa tatggtaggt       660
gatttaagaa ttcatttat taattggtta aaaaagacac aaatgaattt tattcgagaa        720
aaagataaat tatttaaaga taagaaagaa ctagaaatgg aaagagtacg attgtacaaa       780
gaattagaaa accgtaaaaa tattgaagaa cagaaattac atgatgaaag aagaaaatta       840
gatattgata tatctaatgg ttataaacaa ataaaaaaag aaaagaaga acataggaaa        900
cgatttgatg aagaaagatt aagattttta caagaaatcg ataaaattaa attagtatta       960
tatttagaaa aagaaaaata ttatcaagaa tataaaaatt ttgagaatga taaaaaaaaa      1020
attgttgatg caaatattgc tactgaaact atgattgata ttaatgttgg tggagctatt      1080
tttgaaacat ctagacatac cttaacacaa caaaagatt catttataga gaattatta        1140
agtggaagac atcatgtaac cagagataaa caaggaagaa tattcttaga tagggatagt      1200
gagttattta gaattatact taacttctta agaaatccgt taactatacc cataccaaaa      1260
gatttaagtg aaagtgaagc cttgttgaaa gaagcagaat tttatggtat taaattttta      1320
ccattcccat tagtattttg tataggtgga tttgatggtg tagaatattt aaattcgatg      1380
gaattattag atattagtca acaatgctgg cgtatgtgta cacctatgtc taccaaaaaa      1440
gcttattttg gaagtgctgt attgaataat ttcttatacg ttttggtgg taataactat       1500
gattataagg ctttatttga aactgaggtg tatgatcgtt taagagatgt atggtatgtt      1560
tcaagtaatt taaatatacc tagaagaaat aattgtggtg ttacgtcaaa tggtagaatt      1620
tattgtattg ggggatatga tggctcttct attataccga atgtagaagc atatgatcat      1680
cgtatgaaag catgggtaga ggtggcacct ttgaataccc tagatcatc agctatgtgt       1740
gttgcttttg ataataaaat ttatgtcatt ggtggaacta atggtgagag attaaattct      1800
attgaagtat atgaagaaaa aatgaataaa tgggaacaat ttccatatgc cttattagaa      1860
gctagaagtt caggagcagc ttttaattac cttaatcaaa tatatgttgt tggaggtatt      1920
gataatgaac ataacatatt agattccgtt gaacaatatc aaccatttaa taaaagatgg      1980
caatttctaa atggtgtacc agagaaaaaa atgaattttg gagctgccac attgtcagat      2040
tcttatataa ttacaggagg agaaaatggc gaagttctaa attcatgtca tttcttttca      2100
ccagatacaa atgaatggca gcttggccca tctttattag ttcccagatt tggtcactcc      2160
gttttaatag caaatatata a                                                2181
```

<210> SEQ ID NO 2
<211> LENGTH: 726
<212> TYPE: PRT
<213> ORGANISM: Plasmodium falciparum

<400> SEQUENCE: 2

Met Glu Gly Glu Lys Val Lys Thr Lys Ala Asn Ser Ile Ser Asn Phe
1               5                   10                  15

Ser Met Thr Tyr Asp Arg Glu Ser Gly Gly Asn Ser Asn Ser Asp Asp
            20                  25                  30

Lys Ser Gly Ser Ser Ser Glu Asn Asp Ser Asn Ser Phe Met Asn Leu
        35                  40                  45

```
Thr Ser Asp Lys Asn Glu Lys Thr Glu Asn Asn Ser Phe Leu Leu Asn
     50                  55                  60

Asn Ser Ser Tyr Gly Asn Val Lys Asp Ser Leu Leu Glu Ser Ile Asp
 65                  70                  75                  80

Met Ser Val Leu Asp Ser Asn Phe Asp Ser Lys Lys Asp Phe Leu Pro
                 85                  90                  95

Ser Asn Leu Ser Arg Thr Phe Asn Asn Met Ser Lys Asp Asn Ile Gly
            100                 105                 110

Asn Lys Tyr Leu Asn Lys Leu Leu Asn Lys Lys Lys Asp Thr Ile Thr
        115                 120                 125

Asn Glu Asn Asn Asn Ile Asn His Asn Asn Asn Asn Asn Asn Leu Thr
    130                 135                 140

Ala Asn Asn Ile Thr Asn Asn Leu Ile Asn Asn Asn Met Asn Ser Pro
145                 150                 155                 160

Ser Ile Met Asn Thr Asn Lys Lys Glu Asn Phe Leu Asp Ala Ala Asn
                165                 170                 175

Leu Ile Asn Asp Asp Ser Gly Leu Asn Asn Leu Lys Lys Phe Ser Thr
            180                 185                 190

Val Asn Asn Val Asn Asp Thr Tyr Glu Lys Lys Ile Ile Glu Thr Glu
        195                 200                 205

Leu Ser Asp Ala Ser Asp Phe Glu Asn Met Val Gly Asp Leu Arg Ile
    210                 215                 220

Thr Phe Ile Asn Trp Leu Lys Lys Thr Gln Met Asn Phe Ile Arg Glu
225                 230                 235                 240

Lys Asp Lys Leu Phe Lys Asp Lys Glu Leu Glu Met Glu Arg Val
                245                 250                 255

Arg Leu Tyr Lys Glu Leu Glu Asn Arg Lys Asn Ile Glu Glu Gln Lys
            260                 265                 270

Leu His Asp Glu Arg Lys Lys Leu Asp Ile Asp Ile Ser Asn Gly Tyr
        275                 280                 285

Lys Gln Ile Lys Lys Glu Lys Glu Glu His Arg Lys Arg Phe Asp Glu
    290                 295                 300

Glu Arg Leu Arg Phe Leu Gln Glu Ile Asp Lys Ile Lys Leu Val Leu
305                 310                 315                 320

Tyr Leu Glu Lys Glu Lys Tyr Tyr Gln Glu Tyr Lys Asn Phe Glu Asn
                325                 330                 335

Asp Lys Lys Lys Ile Val Asp Ala Asn Ile Ala Thr Glu Thr Met Ile
            340                 345                 350

Asp Ile Asn Val Gly Gly Ala Ile Phe Glu Thr Ser Arg His Thr Leu
        355                 360                 365

Thr Gln Gln Lys Asp Ser Phe Ile Glu Lys Leu Leu Ser Gly Arg His
    370                 375                 380

His Val Thr Arg Asp Lys Gln Gly Arg Ile Phe Leu Asp Arg Asp Ser
385                 390                 395                 400

Glu Leu Phe Arg Ile Ile Leu Asn Phe Leu Arg Asn Pro Leu Thr Ile
                405                 410                 415

Pro Ile Pro Lys Asp Leu Ser Glu Ser Glu Ala Leu Leu Lys Glu Ala
            420                 425                 430

Glu Phe Tyr Gly Ile Lys Phe Leu Pro Phe Pro Leu Val Phe Cys Ile
        435                 440                 445

Gly Gly Phe Asp Gly Val Glu Tyr Leu Asn Ser Met Glu Leu Leu Asp
    450                 455                 460
```

```
Ile Ser Gln Gln Cys Trp Arg Met Cys Thr Pro Met Ser Thr Lys Lys
465                 470                 475                 480

Ala Tyr Phe Gly Ser Ala Val Leu Asn Asn Phe Leu Tyr Val Phe Gly
                485                 490                 495

Gly Asn Asn Tyr Asp Tyr Lys Ala Leu Phe Glu Thr Glu Val Tyr Asp
            500                 505                 510

Arg Leu Arg Asp Val Trp Tyr Val Ser Ser Asn Leu Asn Ile Pro Arg
        515                 520                 525

Arg Asn Asn Cys Gly Val Thr Ser Asn Gly Arg Ile Tyr Cys Ile Gly
    530                 535                 540

Gly Tyr Asp Gly Ser Ser Ile Ile Pro Asn Val Glu Ala Tyr Asp His
545                 550                 555                 560

Arg Met Lys Ala Trp Val Glu Val Ala Pro Leu Asn Thr Pro Arg Ser
                565                 570                 575

Ser Ala Met Cys Val Ala Phe Asp Asn Lys Ile Tyr Val Ile Gly Gly
                580                 585                 590

Thr Asn Gly Glu Arg Leu Asn Ser Ile Glu Val Tyr Glu Glu Lys Met
            595                 600                 605

Asn Lys Trp Glu Gln Phe Pro Tyr Ala Leu Leu Glu Ala Arg Ser Ser
        610                 615                 620

Gly Ala Ala Phe Asn Tyr Leu Asn Gln Ile Tyr Val Val Gly Gly Ile
625                 630                 635                 640

Asp Asn Glu His Asn Ile Leu Asp Ser Val Glu Gln Tyr Gln Pro Phe
                645                 650                 655

Asn Lys Arg Trp Gln Phe Leu Asn Gly Val Pro Glu Lys Lys Met Asn
            660                 665                 670

Phe Gly Ala Ala Thr Leu Ser Asp Ser Tyr Ile Ile Thr Gly Gly Glu
        675                 680                 685

Asn Gly Glu Val Leu Asn Ser Cys His Phe Phe Ser Pro Asp Thr Asn
    690                 695                 700

Glu Trp Gln Leu Gly Pro Ser Leu Leu Val Pro Arg Phe Gly His Ser
705                 710                 715                 720

Val Leu Ile Ala Asn Ile
                725

<210> SEQ ID NO 3
<211> LENGTH: 712
<212> TYPE: PRT
<213> ORGANISM: Plasmodium vivax

<400> SEQUENCE: 3

Met Glu Gly Glu Lys Ile Lys Ser Asn Ser Ile Ser Asn Phe Ser Val
1               5                   10                  15

Thr Tyr Glu Arg Glu Ser Gly Ala Asn Ser Asn Ser Asp Asp Lys Ser
                20                  25                  30

Val Ser Ser Ser Glu Asn Glu Ser Asn Ser Phe Met Asn Leu Thr Ser
            35                  40                  45

Asp Lys Asn Glu Lys Thr Glu Asn Ser Phe Ile Leu Asn Asn Ser
        50                  55                  60

Ser Phe Ala Asn Met Lys Asp Ser Leu Leu Glu Ser Ile Asp Leu Ser
65                  70                  75                  80

Val Leu Asp Ser Asn Phe Asp Ser Lys Lys Asp Phe Leu Pro Ser Asn
                85                  90                  95

Leu Ser Lys Asn Phe Asn Asn Leu Ser Lys Glu Asn Leu Gly Asn Lys
            100                 105                 110
```

```
Tyr Leu Asn Lys Leu Leu Asn Lys Ser Asp Ser Met Phe Met Ser Lys
            115                 120                 125

Gly Lys Asp Met Asn Leu Met Glu Asn Asn Leu Gly Ser Asn Asn Leu
        130                 135                 140

Pro Val Lys Ser Ser Asn Lys Lys Glu Gly Phe Met Asp Ser Ser Thr
145                 150                 155                 160

Pro Ile Asn Ala Asn Glu Asp Asn Ala Met Asn Asn Leu Lys Lys Tyr
                165                 170                 175

Ser Asn Ala Asn Asn Ile Asn Asp Thr Tyr Glu Lys Lys Ile Ile Glu
            180                 185                 190

Thr Glu Leu Ser Asp Ser Ser Asp Phe Glu Asn Met Val Gly Asp Leu
            195                 200                 205

Arg Ile Thr Phe Ile Asn Trp Leu Lys Lys Thr Gln Met Asn Phe Ile
        210                 215                 220

Arg Glu Lys Asp Lys Leu Phe Lys Asp Lys Lys Glu Leu Glu Met Glu
225                 230                 235                 240

Arg Ile Arg Leu Tyr Lys Glu Ile Glu Asn Arg Lys Ser Ile Glu Glu
                245                 250                 255

Gln Lys Leu His Asp Glu Arg Lys Lys Leu Asp Ile Asp Ile Ser Asn
            260                 265                 270

Gly Tyr Lys Gln Ile Lys Lys Glu Lys Glu His Arg Lys Arg Phe
        275                 280                 285

Asp Glu Glu Arg Leu Arg Phe Leu Gln Glu Ile Asp Lys Ile Lys Leu
        290                 295                 300

Val Leu Tyr Leu Glu Lys Glu Lys Tyr Phe Gln Glu Tyr Lys Asn Phe
305                 310                 315                 320

Glu Asn Asp Lys Lys Lys Ile Val Asp Ala Asn Ile Ala Thr Glu Thr
                325                 330                 335

Met Ile Asp Ile Asn Val Gly Gly Ala Ile Phe Glu Thr Ser Arg His
            340                 345                 350

Thr Leu Thr Gln Gln Lys Asp Ser Phe Ile Glu Lys Leu Leu Ser Gly
        355                 360                 365

Arg Tyr His Val Thr Arg Asp Lys Gln Gly Arg Ile Phe Leu Asp Arg
        370                 375                 380

Asp Ser Glu Leu Phe Arg Ile Ile Leu Asn Phe Leu Arg Asn Pro Leu
385                 390                 395                 400

Thr Val Pro Ile Pro Lys Asp Leu Ser Glu Ser Glu Ala Leu Leu Lys
                405                 410                 415

Glu Ala Glu Phe Tyr Gly Ile Lys Phe Leu Pro Phe Pro Leu Val Phe
            420                 425                 430

Cys Met Gly Gly Phe Asp Gly Val Glu Tyr Leu Asn Ser Met Glu Leu
        435                 440                 445

Leu Asp Ile Ser Gln Gln Cys Trp Arg Met Cys Thr Pro Met Ser Thr
        450                 455                 460

Lys Lys Ala Tyr Phe Gly Ser Ala Val Leu Asn Asn Phe Leu Tyr Val
465                 470                 475                 480

Phe Gly Gly Asn Asn Tyr Asp Tyr Lys Ala Leu Phe Glu Thr Glu Val
                485                 490                 495

Tyr Asp Arg Leu Arg Asp Thr Trp Phe Val Ser Ser Asn Leu Asn Ile
            500                 505                 510

Pro Arg Arg Asn Asn Cys Gly Val Thr Ser Asn Gly Arg Ile Tyr Cys
        515                 520                 525
```

```
Ile Gly Gly Tyr Asp Gly Ser Ser Ile Ile Pro Asn Val Glu Ala Tyr
    530                 535                 540

Asp His Arg Met Lys Ala Trp Val Glu Ile Ala Pro Leu Asn Thr Pro
545                 550                 555                 560

Arg Ser Ser Ser Met Cys Val Ala Phe Asp Asn Lys Ile Tyr Val Ile
                565                 570                 575

Gly Gly Thr Asn Gly Glu Arg Leu Asn Ser Ile Glu Val Tyr Asp Glu
            580                 585                 590

Lys Met Asn Lys Trp Glu Gln Phe Pro Tyr Ala Leu Leu Glu Ala Arg
        595                 600                 605

Ser Ser Gly Ala Ala Phe Asn Tyr Leu Asn Gln Ile Tyr Val Val Gly
    610                 615                 620

Gly Ile Asp Asn Glu His Asn Ile Leu Asp Ser Val Glu Gln Tyr Gln
625                 630                 635                 640

Pro Phe Asn Lys Arg Trp Gln Phe Leu Asn Gly Val Pro Glu Lys Lys
                645                 650                 655

Met Asn Phe Gly Ala Ala Thr Leu Ser Asp Ser Tyr Ile Ile Thr Gly
            660                 665                 670

Gly Glu Asn Gly Asp Val Leu Asn Ser Cys His Phe Phe Ser Pro Asp
        675                 680                 685

Thr Asn Glu Trp Gln Ile Gly Pro Ser Leu Leu Val Pro Arg Phe Gly
    690                 695                 700

His Ser Val Leu Ile Ala Asn Ile
705                 710

<210> SEQ ID NO 4
<211> LENGTH: 703
<212> TYPE: PRT
<213> ORGANISM: Plasmodium cynomolgi

<400> SEQUENCE: 4

Met Glu Gly Glu Lys Ile Lys Thr Asn Ser Ile Ser Asn Phe Ser Val
1               5                   10                  15

Thr Tyr Glu Arg Glu Ser Gly Ala Asn Ser Asn Ser Asp Asp Lys Ser
            20                  25                  30

Val Ser Ser Ser Glu Asn Glu Ser Asn Ser Phe Met Asn Leu Thr Ser
        35                  40                  45

Asp Lys Asn Glu Lys Thr Glu Asn Asn Ser Phe Ile Leu Asn Asn Ser
    50                  55                  60

Ser Phe Ala Asn Met Lys Asp Ser Phe Leu Glu Ser Ile Asp Leu Ser
65                  70                  75                  80

Val Leu Asp Ser Asn Phe Asp Ser Lys Lys Asp Phe Leu Pro Ser Asn
                85                  90                  95

Leu Ser Lys Asn Phe Asn Asn Leu Ser Lys Glu Asn Leu Gly Asn Lys
            100                 105                 110

Tyr Leu Asn Lys Leu Leu Asn Lys Ser Asp Ser Ile Phe Met Ser Lys
        115                 120                 125

Ser Lys Asp Met Asn Leu Ile Glu Asn Asn Leu Gly Ser Asn Asn Leu
    130                 135                 140

Pro Val Lys Ser Ser Asn Lys Lys Glu Gly Phe Met Asp Ser Ser Thr
145                 150                 155                 160

Pro Ile Asn Ala Asn Glu Asp Asn Ala Met Asn Asn Arg Lys Lys Tyr
                165                 170                 175

Ser Asn Ser Asn Asn Ile Asn Asp Thr Tyr Glu Lys Lys Ile Ile Glu
            180                 185                 190
```

```
Thr Glu Leu Ser Asp Ser Ser Asp Phe Glu Asn Met Val Gly Asp Leu
        195                 200                 205

Arg Ile Thr Phe Ile Asn Trp Leu Lys Lys Thr Gln Met Asn Phe Ile
    210                 215                 220

Arg Glu Lys Asp Lys Leu Phe Lys Asp Lys Lys Glu Leu Glu Met Glu
225                 230                 235                 240

Arg Ile Arg Leu Tyr Lys Glu Ile Glu Asn Arg Lys Ser Ile Glu Glu
                245                 250                 255

Gln Lys Leu His Asp Glu Arg Lys Lys Leu Asp Ile Asp Ile Ser Asn
                260                 265                 270

Gly Tyr Lys Gln Ile Lys Lys Glu Lys Glu His Arg Lys Arg Phe
                275                 280                 285

Asp Glu Glu Arg Leu Arg Phe Leu Gln Glu Ile Asp Lys Ile Lys Leu
        290                 295                 300

Val Leu Tyr Leu Glu Lys Glu Lys Tyr Phe Gln Glu Tyr Lys Asn Phe
305                 310                 315                 320

Glu Asn Asp Lys Lys Lys Ile Val Asp Ala Asn Ile Ala Thr Glu Thr
                325                 330                 335

Met Ile Asp Ile Asn Val Gly Gly Ala Ile Phe Glu Thr Ser Arg His
                340                 345                 350

Thr Leu Thr Gln Gln Lys Asp Ser Phe Ile Glu Lys Leu Leu Ser Gly
        355                 360                 365

Arg Tyr His Val Thr Arg Asp Lys Gln Gly Arg Ile Phe Leu Asp Arg
        370                 375                 380

Asp Ser Glu Leu Phe Arg Ile Ile Leu Asn Phe Leu Arg Asn Pro Leu
385                 390                 395                 400

Thr Val Pro Ile Pro Lys Asp Leu Ser Glu Ser Glu Ala Leu Leu Lys
                405                 410                 415

Glu Ala Glu Phe Tyr Val Phe Cys Met Gly Gly Phe Asp Gly Val Glu
        420                 425                 430

Tyr Leu Asn Ser Met Glu Leu Leu Asp Ile Ser Gln Gln Cys Trp Arg
        435                 440                 445

Met Cys Thr Pro Met Ser Thr Lys Lys Ala Tyr Phe Gly Ser Ala Val
    450                 455                 460

Leu Asn Asn Phe Leu Tyr Val Phe Gly Gly Asn Asn Tyr Asp Tyr Lys
465                 470                 475                 480

Ala Leu Phe Glu Thr Glu Val Tyr Asp Arg Leu Arg Asp Thr Trp Phe
                485                 490                 495

Val Ser Ser Asn Leu Asn Ile Pro Arg Arg Asn Cys Gly Val Thr
                500                 505                 510

Ser Asn Gly Arg Ile Tyr Cys Ile Gly Gly Tyr Asp Gly Ser Ser Ile
                515                 520                 525

Ile Pro Asn Val Glu Ala Tyr Asp His Arg Met Lys Ala Trp Val Glu
    530                 535                 540

Ile Ala Pro Leu Asn Thr Pro Arg Ser Ser Met Cys Val Ala Phe
545                 550                 555                 560

Asp Asn Lys Ile Tyr Val Ile Gly Gly Thr Asn Gly Glu Arg Leu Asn
                565                 570                 575

Ser Ile Glu Val Tyr Asp Glu Lys Met Asn Lys Trp Glu Gln Phe Pro
        580                 585                 590

Tyr Ala Leu Leu Glu Ala Arg Ser Ser Gly Ala Ala Phe Asn Tyr Leu
        595                 600                 605
```

```
Asn Gln Ile Tyr Val Val Gly Gly Ile Asp Asn Glu His Asn Ile Leu
    610             615                 620
Asp Ser Val Glu Gln Tyr Gln Pro Phe Asn Lys Arg Trp Gln Phe Leu
625             630                 635                 640
Asn Gly Val Pro Glu Lys Lys Met Asn Phe Gly Ala Ala Thr Leu Ser
            645                 650                 655
Asp Ser Tyr Ile Ile Thr Gly Gly Glu Asn Gly Asp Val Leu Asn Ser
            660                 665                 670
Cys His Phe Phe Ser Pro Asp Thr Asn Glu Trp Gln Ile Gly Pro Ser
            675                 680                 685
Leu Leu Val Pro Arg Phe Gly His Ser Val Leu Ile Ala Asn Ile
            690                 695                 700

<210> SEQ ID NO 5
<211> LENGTH: 712
<212> TYPE: PRT
<213> ORGANISM: Plasmodium knowlesi

<400> SEQUENCE: 5

Met Glu Asp Glu Lys Ile Lys Ser Asn Ser Ile Ser Asn Phe Ser Val
1               5                   10                  15
Thr Tyr Glu Arg Glu Ser Gly Ala Asn Ser Asn Ser Asp Asp Lys Ser
                20                  25                  30
Val Ser Ser Ser Glu Asn Glu Ser Asn Ser Phe Met Asn Leu Thr Ser
            35                  40                  45
Asp Lys Asn Glu Lys Thr Glu Asn Asn Ser Phe Ile Leu Asn Asn Ser
    50                  55                  60
Ser Phe Ala Asn Met Lys Asp Ser Phe Leu Glu Ser Ile Asp Leu Ser
65                  70                  75                  80
Ile Leu Asp Ser Asn Phe Asp Ser Lys Lys Asp Phe Leu Pro Ser Asn
                85                  90                  95
Leu Ser Lys Asn Phe Asn Asn Leu Ser Lys Glu Asn Leu Gly Asn Lys
            100                 105                 110
Tyr Leu Asn Lys Leu Leu Asn Lys Ser Asp Ser Leu Phe Met Ser Lys
        115                 120                 125
Asn Lys Asp Met Asn Leu Met Asp Asn Asn Met Gly Ser Asn Asn Leu
130                 135                 140
Pro Val Lys Ser Ser Asn Arg Lys Glu Gly Phe Met Asp Ser Ser Thr
145                 150                 155                 160
Pro Ile Asn Ala Asn Glu Asp Asn Ala Met Asn Asn Leu Lys Lys Tyr
                165                 170                 175
Ser Asn Thr Asn Asn Ile Asn Asp Thr Tyr Glu Lys Lys Ile Ile Glu
            180                 185                 190
Thr Glu Leu Ser Asp Ser Ser Asp Phe Glu Asn Met Val Gly Asp Leu
        195                 200                 205
Arg Ile Thr Phe Ile Asn Trp Leu Lys Lys Thr Gln Met Asn Phe Ile
210                 215                 220
Arg Glu Lys Asp Lys Leu Phe Lys Asp Lys Lys Glu Leu Glu Met Glu
225                 230                 235                 240
Arg Ile Arg Leu Tyr Lys Glu Ile Glu Asn Arg Lys Ser Ile Glu Glu
                245                 250                 255
Gln Lys Leu His Asp Glu Arg Lys Lys Leu Asp Ile Asp Ile Ser Asn
            260                 265                 270
Gly Tyr Lys Gln Ile Lys Lys Glu Lys Glu Glu His Arg Lys Arg Phe
        275                 280                 285
```

```
Asp Glu Glu Arg Leu Arg Phe Leu Gln Glu Ile Asp Lys Ile Lys Leu
    290                 295                 300

Val Leu Tyr Leu Glu Lys Glu Lys Tyr Phe Gln Glu Tyr Lys Asn Phe
305                 310                 315                 320

Glu Asn Asp Lys Lys Ile Val Asp Ala Asn Ile Ala Thr Glu Thr
                325                 330                 335

Met Ile Asp Ile Asn Val Gly Gly Ala Ile Phe Glu Thr Ser Arg His
            340                 345                 350

Thr Leu Thr Gln Gln Lys Asp Ser Phe Ile Glu Lys Leu Leu Ser Gly
        355                 360                 365

Arg Tyr His Val Thr Arg Asp Lys Gln Gly Arg Ile Phe Leu Asp Arg
    370                 375                 380

Asp Ser Glu Leu Phe Arg Ile Ile Leu Asn Phe Leu Arg Asn Pro Leu
385                 390                 395                 400

Thr Val Pro Ile Pro Lys Asp Leu Ser Glu Ser Glu Ala Leu Leu Lys
                405                 410                 415

Glu Ala Glu Phe Tyr Gly Ile Lys Phe Leu Pro Phe Pro Leu Val Phe
            420                 425                 430

Cys Met Gly Gly Phe Asp Gly Val Glu Tyr Leu Asn Ser Met Glu Leu
        435                 440                 445

Leu Asp Ile Ser Gln Gln Cys Trp Arg Met Cys Thr Pro Met Ser Thr
    450                 455                 460

Lys Lys Ala Tyr Phe Gly Ser Ala Val Leu Asn Asn Phe Leu Tyr Val
465                 470                 475                 480

Phe Gly Gly Asn Asn Tyr Asp Tyr Lys Ala Leu Phe Glu Thr Glu Val
                485                 490                 495

Tyr Asp Arg Leu Arg Asp Thr Trp Phe Val Ser Ser Asn Leu Asn Ile
            500                 505                 510

Pro Arg Arg Asn Asn Cys Gly Val Thr Ser Asn Gly Arg Ile Tyr Cys
        515                 520                 525

Ile Gly Gly Tyr Asp Gly Ser Cys Ile Ile Pro Asn Val Glu Ala Tyr
    530                 535                 540

Asp His Arg Met Lys Ala Trp Val Glu Ile Ala Pro Leu Asn Thr Pro
545                 550                 555                 560

Arg Ser Ser Ser Met Cys Val Ala Phe Glu Asn Lys Ile Tyr Val Ile
                565                 570                 575

Gly Gly Thr Asn Gly Glu Arg Leu Asn Ser Ile Glu Val Tyr Asp Glu
            580                 585                 590

Lys Met Asn Lys Trp Glu Gln Phe Pro Tyr Ala Leu Leu Glu Ala Arg
        595                 600                 605

Ser Ser Gly Ala Ala Phe Asn Tyr Leu Asn Gln Ile Tyr Val Val Gly
    610                 615                 620

Gly Ile Asp Asn Glu His Asn Ile Leu Asp Ser Val Glu Gln Tyr Gln
625                 630                 635                 640

Pro Phe Asn Lys Arg Trp Gln Phe Leu Asn Gly Val Pro Glu Lys Lys
                645                 650                 655

Met Asn Phe Gly Ala Ala Thr Leu Ser Asp Ser Tyr Ile Ile Thr Gly
            660                 665                 670

Gly Glu Asn Gly Asp Val Leu Asn Ser Cys His Phe Phe Ser Pro Asp
        675                 680                 685

Thr Asn Glu Trp Gln Ile Gly Pro Ser Leu Leu Val Pro Arg Phe Gly
    690                 695                 700
```

His Ser Val Leu Ile Ala Asn Ile
705             710

<210> SEQ ID NO 6
<211> LENGTH: 708
<212> TYPE: PRT
<213> ORGANISM: Plasmodium berghei

<400> SEQUENCE: 6

Met Glu Asp Asp Lys Ile Lys Ser Asn Ser Ile Ser Asn Phe Ser Val
1               5                   10                  15

Thr Tyr Glu Arg Glu Ser Gly Ser Asn Ser Asn Ser Glu Glu Arg Asp
            20                  25                  30

Met Ser Ser Asp Glu Asn Glu Ser Asn Leu Tyr Met Asn Leu Thr Gly
        35                  40                  45

Asp Lys Asn Glu Lys Ile Glu Asp Asn Ser Ser Phe Val Asn Ile Lys
    50                  55                  60

Asp Ser Leu Leu Glu Ser Ile Asp Leu Ser Val Leu Asp Ser Asn Phe
65                  70                  75                  80

Asp Ser Lys Asn Asp Phe Leu Pro Asn Asn Phe Ser Lys Asn Leu Asn
                85                  90                  95

Asn Ile Thr Lys Asp Asn Ile Asn Asn Lys Tyr Leu Asn Lys Tyr Leu
            100                 105                 110

Asn Lys Asn Asp Ser Ala Phe Met Ala Met Asn Lys Asp Leu Asn Val
        115                 120                 125

Ser Asn Asn Asn Leu Asn Gly Asn Asn Ile Val Gly Ala Pro Thr Asn
    130                 135                 140

Lys Lys Glu Ile Phe Met Asp Ser Gly Ala Ser Ser Ile Asn Met Asn
145                 150                 155                 160

Glu Asp Asn Ser Thr Met His Asn Ile Arg Ile Tyr Lys Asn Thr Asn
                165                 170                 175

Asn Ile Asn Asp Thr Tyr Glu Lys Lys Ile Ile Glu Thr Glu Leu Ser
            180                 185                 190

Asp Ser Ser Asp Phe Glu Asn Met Val Gly Asp Leu Arg Ile Thr Phe
        195                 200                 205

Ile Asn Trp Leu Lys Lys Thr Gln Met Asn Phe Ile Arg Glu Lys Asp
    210                 215                 220

Lys Leu Phe Lys Asp Lys Lys Glu Leu Glu Met Glu Arg Ile Arg Leu
225                 230                 235                 240

Tyr Lys Glu Ile Glu Asn Arg Lys Ala Ile Glu Glu Gln Lys Leu Gln
                245                 250                 255

Asp Glu Arg Lys Lys Leu Asp Ile Asp Ile Ser Asn Gly Tyr Lys Gln
            260                 265                 270

Ile Lys Lys Glu Lys Glu Glu His Arg Lys Arg Phe Asp Asp Glu Arg
        275                 280                 285

Leu Arg Phe Leu Gln Glu Ile Asp Lys Ile Lys Leu Val Leu Tyr Leu
    290                 295                 300

Glu Lys Glu Lys Tyr Phe Gln Glu Tyr Lys Asn Phe Glu Asn Asp Lys
305                 310                 315                 320

Lys Lys Ile Val Asp Ala Asn Ile Ala Thr Glu Thr Met Ile Asp Ile
                325                 330                 335

Asn Val Gly Gly Ala Leu Phe Glu Thr Ser Arg His Thr Leu Thr Gln
            340                 345                 350

Gln Lys Asp Ser Phe Ile Glu Lys Leu Leu Ser Gly Arg Tyr His Ile
        355                 360                 365

Thr Arg Asp Lys Gln Gly Arg Ile Phe Leu Asp Arg Asp Ser Glu Leu
            370                 375                 380

Phe Arg Ile Ile Leu Asn Phe Leu Arg Asn Pro Leu Thr Ile Pro Ile
385                 390                 395                 400

Pro Lys Asp Leu Gly Glu Ser Glu Ala Leu Leu Lys Glu Ala Glu Phe
                405                 410                 415

Tyr Gly Ile Lys Phe Leu Pro Phe Pro Leu Val Phe Ser Ile Gly Gly
                420                 425                 430

Phe Asp Gly Val Glu Tyr Leu Asn Ser Met Glu Leu Leu Asp Ile Ser
            435                 440                 445

Gln Gln Cys Trp Arg Met Cys Thr Pro Met Ser Thr Lys Lys Ala Tyr
450                 455                 460

Phe Gly Ser Ala Val Leu Asn Asn Phe Leu Tyr Val Phe Gly Gly Asn
465                 470                 475                 480

Asn Tyr Asp Tyr Lys Ala Leu Phe Glu Thr Glu Val Tyr Asp Arg Leu
                485                 490                 495

Arg Asp Thr Trp Phe Leu Ser Ser Asn Leu Asn Ile Pro Arg Arg Asn
                500                 505                 510

Asn Cys Gly Ile Thr Ser Asn Gly Arg Ile Tyr Cys Ile Gly Gly Tyr
            515                 520                 525

Asp Gly Ser Ser Ile Ile Pro Asn Val Glu Ala Tyr Asp His Arg Met
            530                 535                 540

Lys Ala Trp Ile Glu Val Ala Pro Leu Asn Thr Pro Arg Ser Ser Ala
545                 550                 555                 560

Met Cys Val Ala Phe Asp Asn Lys Ile Tyr Val Val Gly Gly Ala Asn
                565                 570                 575

Gly Glu Arg Leu Asn Ser Ile Glu Val Tyr Asp Glu Lys Met Asn Lys
                580                 585                 590

Trp Glu Asn Phe Pro Tyr Ala Leu Leu Glu Ala Arg Ser Ser Gly Ala
            595                 600                 605

Ala Phe Asn Tyr Leu Asn Gln Ile Tyr Val Val Gly Gly Ile Asp Asn
            610                 615                 620

Glu His Asn Ile Leu Glu Ser Val Glu Gln Tyr Gln Pro Phe Asn Lys
625                 630                 635                 640

Arg Trp Gln Phe Leu Asn Gly Ile Pro Glu Lys Lys Met Asn Phe Gly
                645                 650                 655

Ala Thr Thr Leu Ser Asp Ser Tyr Ile Ile Thr Gly Gly Glu Asn Gly
            660                 665                 670

Asp Val Leu Asn Ser Cys His Phe Ser Pro Asp Thr Asn Glu Trp
            675                 680                 685

Gln Ile Gly Pro Pro Leu Leu Val Pro Arg Phe Gly His Ser Val Leu
            690                 695                 700

Val Ala Asn Ile
705

<210> SEQ ID NO 7
<211> LENGTH: 708
<212> TYPE: PRT
<213> ORGANISM: Plasmodium yoelii

<400> SEQUENCE: 7

Met Glu Asp Asp Lys Ile Lys Ser Asn Ser Ile Ser Asn Phe Ser Val
1               5                   10                  15

Thr Tyr Glu Arg Glu Ser Gly Ser Asn Ser Asn Ser Glu Glu Arg Asp

```
                    20                  25                  30
Met Ser Ser Asp Glu Asn Glu Ser Asn Leu Phe Met Asn Leu Thr Gly
                35                  40                  45
Asp Lys Asn Glu Lys Ile Glu Asp Asn Ser Ser Phe Val Asn Met Lys
 50                  55                  60
Asp Ser Leu Leu Glu Ser Ile Asp Leu Ser Val Leu Asp Ser Asn Phe
 65                  70                  75                  80
Asp Ser Lys Asn Asp Phe Leu Pro Asn Asn Phe Ser Lys Asn Leu Asn
                 85                  90                  95
Asn Ile Thr Lys Asp Asn Ile Ser Asn Lys Tyr Leu Asn Lys Tyr Leu
                100                 105                 110
Asn Lys Asn Asp Ser Ala Phe Met Thr Met Ser Lys Asp Leu Asn Val
                115                 120                 125
Ser Asn Asn Asn Leu Asn Gly Asn Asn Ile Val Gly Ala Pro Thr Asn
                130                 135                 140
Lys Lys Glu Ile Phe Met Asp Ser Gly Ala Ser Ser Ile Asn Met Asn
145                 150                 155                 160
Glu Asp Asn Ser Thr Met His Asn Ile Arg Ile Tyr Lys Asn Thr Asn
                165                 170                 175
Asn Ile Asn Asp Thr Tyr Glu Lys Lys Ile Ile Glu Thr Glu Leu Ser
                180                 185                 190
Asp Ser Ser Asp Phe Glu Asn Met Val Gly Asp Leu Arg Ile Thr Phe
                195                 200                 205
Ile Asn Trp Leu Lys Lys Thr Gln Met Asn Phe Ile Arg Glu Lys Asp
                210                 215                 220
Lys Leu Phe Lys Asp Lys Lys Glu Leu Glu Met Glu Arg Ile Arg Leu
225                 230                 235                 240
Tyr Lys Glu Ile Glu Asn Arg Lys Ala Ile Glu Glu Gln Lys Leu Gln
                245                 250                 255
Asp Glu Arg Lys Lys Leu Asp Ile Asp Ile Ser Asn Gly Tyr Lys Gln
                260                 265                 270
Ile Lys Lys Glu Lys Glu Glu His Arg Lys Arg Phe Asp Asp Glu Arg
                275                 280                 285
Leu Arg Phe Leu Gln Glu Ile Asp Lys Ile Lys Leu Val Leu Tyr Leu
                290                 295                 300
Glu Lys Glu Lys Tyr Phe Gln Gly Tyr Lys Asn Phe Glu Asn Asp Lys
305                 310                 315                 320
Lys Lys Ile Val Asp Ala Asn Ile Ala Thr Glu Thr Met Ile Asp Ile
                325                 330                 335
Asn Val Gly Gly Ala Leu Phe Glu Thr Ser Arg His Thr Leu Thr Gln
                340                 345                 350
Gln Lys Asp Ser Phe Ile Glu Lys Leu Leu Ser Gly Arg Tyr His Ile
                355                 360                 365
Thr Arg Asp Lys Gln Gly Arg Ile Phe Leu Asp Arg Asp Ser Glu Leu
                370                 375                 380
Phe Arg Ile Ile Leu Asn Phe Leu Arg Asn Pro Leu Thr Ile Pro Ile
385                 390                 395                 400
Pro Lys Asp Leu Gly Glu Ser Glu Ala Leu Leu Lys Glu Ala Glu Phe
                405                 410                 415
Tyr Gly Ile Lys Phe Leu Pro Phe Pro Leu Val Phe Ser Ile Gly Gly
                420                 425                 430
Phe Asp Gly Val Glu Tyr Leu Asn Ser Met Glu Leu Leu Asp Ile Ser
                435                 440                 445
```

```
Gln Gln Cys Trp Arg Met Cys Thr Pro Met Ser Thr Lys Lys Ala Tyr
    450                 455                 460

Phe Gly Ser Ala Val Leu Asn Asn Phe Leu Tyr Val Phe Gly Gly Asn
465                 470                 475                 480

Asn Tyr Asp Tyr Lys Ala Leu Phe Glu Thr Glu Val Tyr Asp Arg Leu
                485                 490                 495

Arg Asp Thr Trp Phe Leu Ser Ser Asn Leu Asn Ile Pro Arg Arg Asn
            500                 505                 510

Asn Cys Gly Ile Thr Ser Asn Gly Arg Ile Tyr Cys Ile Gly Gly Tyr
        515                 520                 525

Asp Gly Ser Ser Ile Ile Pro Asn Val Glu Ala Tyr Asp His Arg Met
    530                 535                 540

Lys Ala Trp Ile Glu Val Ala Pro Leu Asn Thr Pro Arg Ser Ser Ala
545                 550                 555                 560

Met Cys Val Ala Phe Asp Asn Lys Ile Tyr Val Val Gly Gly Ala Asn
                565                 570                 575

Gly Glu Arg Leu Asn Ser Ile Glu Val Tyr Asp Glu Lys Met Asn Lys
            580                 585                 590

Trp Glu Asn Phe Pro Tyr Ala Leu Leu Glu Ala Arg Ser Ser Gly Ala
        595                 600                 605

Ala Phe Asn Tyr Leu Asn Gln Ile Tyr Val Val Gly Gly Ile Asp Asn
    610                 615                 620

Glu His Asn Ile Leu Glu Ser Val Glu Gln Tyr Gln Pro Phe Asn Lys
625                 630                 635                 640

Arg Trp Gln Phe Leu Asn Gly Ile Pro Glu Lys Lys Met Asn Phe Gly
                645                 650                 655

Ala Thr Thr Leu Ser Asp Ser Tyr Ile Ile Thr Gly Gly Glu Asn Gly
            660                 665                 670

Asp Val Leu Asn Ser Cys His Phe Phe Ser Pro Asp Thr Asn Glu Trp
        675                 680                 685

Gln Ile Gly Pro Ser Leu Leu Val Pro Arg Phe Gly His Ser Val Leu
    690                 695                 700

Val Ala Asn Ile
705

<210> SEQ ID NO 8
<211> LENGTH: 708
<212> TYPE: PRT
<213> ORGANISM: Plasmodium chabaudi

<400> SEQUENCE: 8

Met Glu Asp Asp Lys Ile Lys Ser Asn Ser Ile Ser Asn Phe Ser Val
1               5                   10                  15

Thr Tyr Glu Arg Glu Ser Gly Ser Asn Ser Asn Ser Glu Glu Arg Asp
                20                  25                  30

Ile Ser Ser Asp Glu Asn Glu Ser Asn Leu Phe Met Asn Leu Thr Gly
            35                  40                  45

Asp Lys Asn Glu Lys Ile Glu Asp Asn Ser Ser Phe Val Asn Met Lys
        50                  55                  60

Asp Ser Leu Leu Glu Ser Ile Asp Leu Ser Val Leu Asp Ser Asn Phe
65                  70                  75                  80

Asp Ser Lys Asn Asp Phe Leu Pro Asn Asn Phe Ser Lys Asn Leu Asn
                85                  90                  95

Asn Leu Thr Lys Asp Thr Ile Gly Asn Lys Tyr Leu Ser Lys Tyr Leu
```

-continued

```
                100                 105                 110
Asn Lys Asn Asp Pro Ala Phe Met Ala Met Ala Lys Asp Leu Asn Val
            115                 120                 125

Ser Asn Asn Asn Ile Asn Gly Asn Asn Ile Val Gly Ala Pro Ala Asn
130                 135                 140

Lys Lys Glu Met Phe Met Asp Ser Gly Ala Ser Ser Ile Asn Met Asn
145                 150                 155                 160

Asp Asp Asn Thr Thr Met His Asn Val Arg Lys Tyr Lys Ser Thr Asn
                165                 170                 175

Asn Val Asn Asp Thr Tyr Glu Lys Lys Ile Glu Thr Glu Leu Ser
            180                 185                 190

Asp Ser Ser Asp Phe Glu Asn Met Val Gly Asp Leu Arg Ile Thr Phe
            195                 200                 205

Ile Asn Trp Leu Lys Lys Thr Gln Met Asn Phe Ile Arg Glu Lys Glu
        210                 215                 220

Lys Leu Phe Lys Asp Lys Lys Glu Leu Glu Met Glu Arg Ile Arg Leu
225                 230                 235                 240

Tyr Lys Glu Ile Glu Asn Arg Lys Asn Ile Glu Glu Gln Lys Leu Gln
                245                 250                 255

Asp Glu Arg Lys Lys Leu Asp Ile Asp Ile Ser Asn Gly Tyr Lys Gln
            260                 265                 270

Ile Lys Lys Glu Lys Glu Glu His Arg Lys Arg Phe Asp Asp Glu Arg
        275                 280                 285

Leu Arg Phe Leu Gln Glu Ile Asp Lys Ile Lys Leu Val Leu Tyr Leu
        290                 295                 300

Glu Lys Glu Lys Tyr Phe Gln Glu Tyr Lys Asn Phe Glu Asn Asp Lys
305                 310                 315                 320

Lys Lys Ile Val Asp Ala Asn Ile Ala Thr Glu Thr Met Ile Asp Ile
            325                 330                 335

Asn Val Gly Gly Ala Leu Phe Glu Thr Ser Arg His Thr Leu Thr Gln
            340                 345                 350

Gln Lys Asp Ser Phe Ile Glu Gln Leu Leu Ser Gly Arg Tyr His Ile
        355                 360                 365

Thr Arg Asp Lys Gln Gly Arg Ile Phe Leu Asp Arg Asp Ser Glu Leu
        370                 375                 380

Phe Arg Ile Ile Leu Asn Phe Leu Arg Asn Pro Leu Thr Ile Pro Ile
385                 390                 395                 400

Pro Lys Asp Leu Gly Glu Ser Glu Ala Leu Leu Lys Glu Ala Glu Tyr
                405                 410                 415

Tyr Gly Ile Lys Phe Leu Pro Phe Pro Leu Val Phe Cys Ile Gly Gly
            420                 425                 430

Phe Asp Gly Val Glu Tyr Leu Asn Ser Met Glu Leu Leu Asp Ile Ser
            435                 440                 445

Gln Gln Cys Trp Arg Met Cys Thr Pro Met Ser Thr Lys Lys Ala Tyr
        450                 455                 460

Phe Gly Ser Ala Val Leu Asn Asn Phe Leu Tyr Val Phe Gly Gly Asn
465                 470                 475                 480

Asn Tyr Asp Tyr Lys Ala Leu Phe Glu Thr Glu Val Tyr Asp Arg Leu
                485                 490                 495

Arg Asp Thr Trp Phe Leu Ser Ser Asn Leu Asn Ile Pro Arg Arg Asn
            500                 505                 510

Asn Cys Gly Ile Thr Ser Asn Gly Arg Ile Tyr Cys Ile Gly Gly Tyr
        515                 520                 525
```

Asp Gly Ser Ser Ile Ile Pro Asn Val Glu Ala Tyr Asp His Arg Met
            530                 535                 540

Lys Ala Trp Ile Glu Val Ala Pro Leu Asn Thr Pro Arg Ser Ser Ala
545                 550                 555                 560

Met Cys Val Ala Phe Asp Asn Lys Ile Tyr Val Ile Gly Gly Ala Asn
                565                 570                 575

Gly Glu Arg Leu Asn Ser Ile Glu Val Tyr Asp Glu Lys Met Asn Lys
            580                 585                 590

Trp Glu Lys Phe Pro Tyr Ala Leu Leu Glu Ala Arg Ser Ser Gly Ala
            595                 600                 605

Ala Phe Asn Tyr Leu Asn Gln Ile Tyr Val Val Gly Gly Ile Asp Asn
            610                 615                 620

Glu His Asn Ile Leu Glu Ser Val Glu Gln Tyr Gln Pro Phe Asn Lys
625                 630                 635                 640

Arg Trp Gln Phe Leu Asn Gly Ile Pro Glu Lys Lys Met Asn Phe Gly
                645                 650                 655

Ala Thr Thr Leu Ser Asp Ser Tyr Ile Ile Thr Gly Gly Glu Asn Gly
            660                 665                 670

Asp Val Leu Asn Ser Cys His Phe Phe Ser Pro Asp Thr Asn Glu Trp
            675                 680                 685

Gln Ile Gly Pro Ser Leu Leu Val Pro Arg Phe Gly His Ser Val Leu
            690                 695                 700

Ile Ala Asn Ile
705

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
cggagtgacc aaatctggga                                              20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gggaatctgg tggtaacagc                                              20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
cgccagcatt gttgactaat                                              20

<210> SEQ ID NO 12
<211> LENGTH: 20
<212> TYPE: DNA
<213> ORGANISM: Artificial Sequence
<220> FEATURE:

<223> OTHER INFORMATION: Primer

<400> SEQUENCE: 12
gcggaagtag tagcgagaat                                          20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
gccaagctgc cattcatttg                                          20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
gccttgttga aagaagcaga                                          20

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
aggtggattt gatggtgtag aat                                      23

<210> SEQ ID NO 16
<211> LENGTH: 25
<212> TYPE: DNA
<213> ORGANISM: Artificial Sequence
<220> FEATURE:
<223> OTHER INFORMATION: Primer

<400> SEQUENCE: 16
catacacctc agtttcaaat aaagc                                    25

<210> SEQ ID NO 17
<211> LENGTH: 26
<212> TYPE: DNA
<213> ORGANISM: Artificial Sequence
<220> FEATURE:
<223> OTHER INFORMATION: Primer

<400> SEQUENCE: 17
aatttcttat acgttttggg tggtaa                                   26

<210> SEQ ID NO 18
<211> LENGTH: 23
<212> TYPE: DNA
<213> ORGANISM: Artificial Sequence
<220> FEATURE:
<223> OTHER INFORMATION: Primer

<400> SEQUENCE: 18
ctctacccat gctttcatac gat                                      23

```
<210> SEQ ID NO 19
<211> LENGTH: 27
<212> TYPE: DNA
<213> ORGANISM: Artificial Sequence
<220> FEATURE:
<223> OTHER INFORMATION: Primer

<400> SEQUENCE: 19
ggatatgatg gctcttctat tataccg                                    27

<210> SEQ ID NO 20
<211> LENGTH: 27
<212> TYPE: DNA
<213> ORGANISM: Artificial Sequence
<220> FEATURE:
<223> OTHER INFORMATION: Primer

<400> SEQUENCE: 20
acttcaatag aatttaatct ctcacca                                    27

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
atgtcattgg tggaactaat ggt                                        23

<210> SEQ ID NO 22
<211> LENGTH: 24
<212> TYPE: DNA
<213> ORGANISM: Artificial Sequence
<220> FEATURE:
<223> OTHER INFORMATION: Primer

<400> SEQUENCE: 22
ttaaatggtt gatattgttc aacg                                       24

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
ttcaggagca gcttttaatt acc                                        23

<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
ctggtgaaaa gaaatgacat gaa                                        23

<210> SEQ ID NO 25
<211> LENGTH: 23
<212> TYPE: DNA
<213> ORGANISM: Artificial Sequence
<220> FEATURE:
<223> OTHER INFORMATION: Primer
```

<400> SEQUENCE: 25
ccttgttgaa agaagcagaa ttt        23

<210> SEQ ID NO 26
<211> LENGTH: 25
<212> TYPE: DNA
<213> ORGANISM: Artificial Sequence
<220> FEATURE:
<223> OTHER INFORMATION: Primer

<400> SEQUENCE: 26
attcaataca gcacttccaa aataa        25

<210> SEQ ID NO 27
<211> LENGTH: 23
<212> TYPE: DNA
<213> ORGANISM: Artificial Sequence
<220> FEATURE:
<223> OTHER INFORMATION: Primer

<400> SEQUENCE: 27
aggtggattt gatggtgtag aat        23

<210> SEQ ID NO 28
<211> LENGTH: 25
<212> TYPE: DNA
<213> ORGANISM: Artificial Sequence
<220> FEATURE:
<223> OTHER INFORMATION: Primer

<400> SEQUENCE: 28
catacacctc agtttcaaat aaagc        25

<210> SEQ ID NO 29
<211> LENGTH: 26
<212> TYPE: DNA
<213> ORGANISM: Artificial Sequence
<220> FEATURE:
<223> OTHER INFORMATION: Primer

<400> SEQUENCE: 29
aatttcttat acgtttttgg tggtaa        26

<210> SEQ ID NO 30
<211> LENGTH: 23
<212> TYPE: DNA
<213> ORGANISM: Artificial Sequence
<220> FEATURE:
<223> OTHER INFORMATION: Primer

<400> SEQUENCE: 30
ctctacccat gctttcatac gat        23

<210> SEQ ID NO 31
<211> LENGTH: 27
<212> TYPE: DNA
<213> ORGANISM: Artificial Sequence
<220> FEATURE:
<223> OTHER INFORMATION: Primer

<400> SEQUENCE: 31
ggatatgatg gctcttctat tataccg        27

<210> SEQ ID NO 32
<211> LENGTH: 27

```
<212> TYPE: DNA
<213> ORGANISM: Artificial Sequence
<220> FEATURE:
<223> OTHER INFORMATION: Primer

<400> SEQUENCE: 32
acttcaatag aatttaatct ctcacca                                              27

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33
atgtcattgg tggaactaat ggt                                                  23

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
ttaaatggtt gatattgttc aacg                                                 24

<210> SEQ ID NO 35
<211> LENGTH: 23
<212> TYPE: DNA
<213> ORGANISM: Artificial Sequence
<220> FEATURE:
<223> OTHER INFORMATION: Primer

<400> SEQUENCE: 35
ttcaggagca gcttttaatt acc                                                  23

<210> SEQ ID NO 36
<211> LENGTH: 23
<212> TYPE: DNA
<213> ORGANISM: Artificial Sequence
<220> FEATURE:
<223> OTHER INFORMATION: Primer

<400> SEQUENCE: 36
ctggtgaaaa gaaatgacat gaa                                                  23

<210> SEQ ID NO 37
<211> LENGTH: 24
<212> TYPE: DNA
<213> ORGANISM: Artificial Sequence
<220> FEATURE:
<223> OTHER INFORMATION: Primer

<400> SEQUENCE: 37
ccttgttgaa agaagcagaa tttt                                                 24

<210> SEQ ID NO 38
<211> LENGTH: 25
<212> TYPE: DNA
<213> ORGANISM: Artificial Sequence
<220> FEATURE:
<223> OTHER INFORMATION: Primer

<400> SEQUENCE: 38
```
attcaataca gcagttccaa aataa                                          25

<210> SEQ ID NO 39
<211> LENGTH: 26
<212> TYPE: DNA
<213> ORGANISM: Artificial Sequence
<220> FEATURE:
<223> OTHER INFORMATION: Primer

<400> SEQUENCE: 39
ttgagcttct ttttcccaat aatggc                                         26

<210> SEQ ID NO 40
<211> LENGTH: 26
<212> TYPE: DNA
<213> ORGANISM: Artificial Sequence
<220> FEATURE:
<223> OTHER INFORMATION: Primer

<400> SEQUENCE: 40
gtgaaaagga taataaattc tatgcc                                         26

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
agcaagaacg ttttgtgtaa a                                              21

<210> SEQ ID NO 42
<211> LENGTH: 28
<212> TYPE: DNA
<213> ORGANISM: Artificial Sequence
<220> FEATURE:
<223> OTHER INFORMATION: Primer

<400> SEQUENCE: 42
taatatgtaa agtgattatg tatatcgc                                       28

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
agaagagcca tcatatcccc c                                              21

<210> SEQ ID NO 44
<211> LENGTH: 25
<212> TYPE: DNA
<213> ORGANISM: Artificial Sequence
<220> FEATURE:
<223> OTHER INFORMATION: Primer

<400> SEQUENCE: 44
atatgagtaa aatgtcaggt tttgg                                          25

<210> SEQ ID NO 45
<211> LENGTH: 21
<212> TYPE: DNA
<213> ORGANISM: Artificial Sequence

```
<220> FEATURE:
<223> OTHER INFORMATION: Primer

<400> SEQUENCE: 45
aaatagttgg gcgtagctca g                                              21

<210> SEQ ID NO 46
<211> LENGTH: 26
<212> TYPE: DNA
<213> ORGANISM: Artificial Sequence
<220> FEATURE:
<223> OTHER INFORMATION: Primer

<400> SEQUENCE: 46
tgatatatgt ttgtaggagc tgtgag                                         26

<210> SEQ ID NO 47
<211> LENGTH: 25
<212> TYPE: DNA
<213> ORGANISM: Artificial Sequence
<220> FEATURE:
<223> OTHER INFORMATION: Primer

<400> SEQUENCE: 47
tatctaccat atattctgat tctcc                                          25

<210> SEQ ID NO 48
<211> LENGTH: 24
<212> TYPE: DNA
<213> ORGANISM: Artificial Sequence
<220> FEATURE:
<223> OTHER INFORMATION: Primer

<400> SEQUENCE: 48
gaattcttta atggttttga agat                                           24

<210> SEQ ID NO 49
<211> LENGTH: 28
<212> TYPE: DNA
<213> ORGANISM: Artificial Sequence
<220> FEATURE:
<223> OTHER INFORMATION: Primer

<400> SEQUENCE: 49
atgctagaga agttaaagag aagaagcg                                       28

<210> SEQ ID NO 50
<211> LENGTH: 23
<212> TYPE: DNA
<213> ORGANISM: Artificial Sequence
<220> FEATURE:
<223> OTHER INFORMATION: Primer

<400> SEQUENCE: 50
agtggaagac atcatgtaac cag                                            23

<210> SEQ ID NO 51
<211> LENGTH: 21
<212> TYPE: DNA
<213> ORGANISM: Artificial Sequence
<220> FEATURE:
<223> OTHER INFORMATION: Primer

<400> SEQUENCE: 51
tgcttgttgt gattcatggg g                                              21
```

<210> SEQ ID NO 52
<211> LENGTH: 25
<212> TYPE: DNA
<213> ORGANISM: Artificial Sequence
<220> FEATURE:
<223> OTHER INFORMATION: Primer

<400> SEQUENCE: 52
tatcacaatt aagtgtatca caacg                                    25

<210> SEQ ID NO 53
<211> LENGTH: 17
<212> TYPE: DNA
<213> ORGANISM: Artificial Sequence
<220> FEATURE:
<223> OTHER INFORMATION: Probe

<400> SEQUENCE: 53
tttgtatagg tggattt                                             17

<210> SEQ ID NO 54
<211> LENGTH: 16
<212> TYPE: DNA
<213> ORGANISM: Artificial Sequence
<220> FEATURE:
<223> OTHER INFORMATION: Probe

<400> SEQUENCE: 54
ccattcccat tagtat                                              16

<210> SEQ ID NO 55
<211> LENGTH: 16
<212> TYPE: DNA
<213> ORGANISM: Artificial Sequence
<220> FEATURE:
<223> OTHER INFORMATION: Probe

<400> SEQUENCE: 55
ccattcccat tagtaa                                              16

<210> SEQ ID NO 56
<211> LENGTH: 19
<212> TYPE: DNA
<213> ORGANISM: Artificial Sequence
<220> FEATURE:
<223> OTHER INFORMATION: Probe

<400> SEQUENCE: 56
tggatttgat ggtgtagaa                                           19

<210> SEQ ID NO 57
<211> LENGTH: 19
<212> TYPE: DNA
<213> ORGANISM: Artificial Sequence
<220> FEATURE:
<223> OTHER INFORMATION: Probe

<400> SEQUENCE: 57
cattagtatt ttgtatagg                                           19

<210> SEQ ID NO 58
<211> LENGTH: 19
<212> TYPE: DNA
<213> ORGANISM: Artificial Sequence
<220> FEATURE:
<223> OTHER INFORMATION: Probe

```
<400> SEQUENCE: 58
cattagtatt ttgtatagc                                               19

<210> SEQ ID NO 59
<211> LENGTH: 32
<212> TYPE: DNA
<213> ORGANISM: Artificial Sequence
<220> FEATURE:
<223> OTHER INFORMATION: Probe

<400> SEQUENCE: 59
attcgatgga attattagat attagtcaac aa                                32

<210> SEQ ID NO 60
<211> LENGTH: 28
<212> TYPE: DNA
<213> ORGANISM: Artificial Sequence
<220> FEATURE:
<223> OTHER INFORMATION: Probe

<400> SEQUENCE: 60
gstggatttg atggtgtaga atatttaa                                     28

<210> SEQ ID NO 61
<211> LENGTH: 28
<212> TYPE: DNA
<213> ORGANISM: Artificial Sequence
<220> FEATURE:
<223> OTHER INFORMATION: Probe

<400> SEQUENCE: 61
gstggatttg atggtgtaga atatttat                                     28

<210> SEQ ID NO 62
<211> LENGTH: 17
<212> TYPE: DNA
<213> ORGANISM: Artificial Sequence
<220> FEATURE:
<223> OTHER INFORMATION: Probe

<400> SEQUENCE: 62
ctggcgtatg tgtacac                                                 17

<210> SEQ ID NO 63
<211> LENGTH: 16
<212> TYPE: DNA
<213> ORGANISM: Artificial Sequence
<220> FEATURE:
<223> OTHER INFORMATION: Probe

<400> SEQUENCE: 63
atattagtca acaatg                                                  16

<210> SEQ ID NO 64
<211> LENGTH: 16
<212> TYPE: DNA
<213> ORGANISM: Artificial Sequence
<220> FEATURE:
<223> OTHER INFORMATION: Probe

<400> SEQUENCE: 64
atattagtca acaata                                                  16

<210> SEQ ID NO 65
```

```
<211> LENGTH: 18
<212> TYPE: DNA
<213> ORGANISM: Artificial Sequence
<220> FEATURE:
<223> OTHER INFORMATION: Probe

<400> SEQUENCE: 65
cgtatgtgta cacctatg                                                 18

<210> SEQ ID NO 66
<211> LENGTH: 18
<212> TYPE: DNA
<213> ORGANISM: Artificial Sequence
<220> FEATURE:
<223> OTHER INFORMATION: Probe

<400> SEQUENCE: 66
attagtcaac aatgctgg                                                 18

<210> SEQ ID NO 67
<211> LENGTH: 18
<212> TYPE: DNA
<213> ORGANISM: Artificial Sequence
<220> FEATURE:
<223> OTHER INFORMATION: Probe

<400> SEQUENCE: 67
attagtcaac aatgctga                                                 18

<210> SEQ ID NO 68
<211> LENGTH: 19
<212> TYPE: DNA
<213> ORGANISM: Artificial Sequence
<220> FEATURE:
<223> OTHER INFORMATION: Probe

<400> SEQUENCE: 68
ttattttgga agtgctgta                                                19

<210> SEQ ID NO 69
<211> LENGTH: 18
<212> TYPE: DNA
<213> ORGANISM: Artificial Sequence
<220> FEATURE:
<223> OTHER INFORMATION: Probe

<400> SEQUENCE: 69
tatgtctacc aaaaaagc                                                 18

<210> SEQ ID NO 70
<211> LENGTH: 18
<212> TYPE: DNA
<213> ORGANISM: Artificial Sequence
<220> FEATURE:
<223> OTHER INFORMATION: Probe

<400> SEQUENCE: 70
tatgtctacc aaaaaagt                                                 18

<210> SEQ ID NO 71
<211> LENGTH: 27
<212> TYPE: DNA
<213> ORGANISM: Artificial Sequence
<220> FEATURE:
<223> OTHER INFORMATION: Probe

<400> SEQUENCE: 71
```

```
acgttttgg tggtaataac tatgatt                                    27

<210> SEQ ID NO 72
<211> LENGTH: 29
<212> TYPE: DNA
<213> ORGANISM: Artificial Sequence
<220> FEATURE:
<223> OTHER INFORMATION: Probe

<400> SEQUENCE: 72
tggaagtgct gtattgaata atttcttat                                 29

<210> SEQ ID NO 73
<211> LENGTH: 29
<212> TYPE: DNA
<213> ORGANISM: Artificial Sequence
<220> FEATURE:
<223> OTHER INFORMATION: Probe

<400> SEQUENCE: 73
tggaagtgct gtattgaata atttcttac                                 29

<210> SEQ ID NO 74
<211> LENGTH: 20
<212> TYPE: DNA
<213> ORGANISM: Artificial Sequence
<220> FEATURE:
<223> OTHER INFORMATION: Probe

<400> SEQUENCE: 74
gtaatttaaa tatacctaga                                           20

<210> SEQ ID NO 75
<211> LENGTH: 19
<212> TYPE: DNA
<213> ORGANISM: Artificial Sequence
<220> FEATURE:
<223> OTHER INFORMATION: Probe

<400> SEQUENCE: 75
gatgtatggt atgtttcaa                                            19

<210> SEQ ID NO 76
<211> LENGTH: 19
<212> TYPE: DNA
<213> ORGANISM: Artificial Sequence
<220> FEATURE:
<223> OTHER INFORMATION: Probe

<400> SEQUENCE: 76
gatgtatggt atgtttcat                                            19

<210> SEQ ID NO 77
<211> LENGTH: 18
<212> TYPE: DNA
<213> ORGANISM: Artificial Sequence
<220> FEATURE:
<223> OTHER INFORMATION: Probe

<400> SEQUENCE: 77
tacgtcaaat ggtagaat                                             18

<210> SEQ ID NO 78
<211> LENGTH: 19
<212> TYPE: DNA
```

```
<213> ORGANISM: Artificial Sequence
<220> FEATURE:
<223> OTHER INFORMATION: Probe

<400> SEQUENCE: 78
gaagaaataa ttgtggtgt                                              19

<210> SEQ ID NO 79
<211> LENGTH: 19
<212> TYPE: DNA
<213> ORGANISM: Artificial Sequence
<220> FEATURE:
<223> OTHER INFORMATION: Probe

<400> SEQUENCE: 79
gaagaaataa ttgtggtgc                                              19

<210> SEQ ID NO 80
<211> LENGTH: 26
<212> TYPE: DNA
<213> ORGANISM: Artificial Sequence
<220> FEATURE:
<223> OTHER INFORMATION: Probe

<400> SEQUENCE: 80
aatttattgt aytgggggat atgatg                                      26

<210> SEQ ID NO 81
<211> LENGTH: 23
<212> TYPE: DNA
<213> ORGANISM: Artificial Sequence
<220> FEATURE:
<223> OTHER INFORMATION: Probe

<400> SEQUENCE: 81
tgtggtgtta cgtcaawtgg tag                                         23

<210> SEQ ID NO 82
<211> LENGTH: 23
<212> TYPE: DNA
<213> ORGANISM: Artificial Sequence
<220> FEATURE:
<223> OTHER INFORMATION: Probe

<400> SEQUENCE: 82
tgtggtgtta cgtcaawtgg tac                                         23

<210> SEQ ID NO 83
<211> LENGTH: 19
<212> TYPE: DNA
<213> ORGANISM: Artificial Sequence
<220> FEATURE:
<223> OTHER INFORMATION: Probe

<400> SEQUENCE: 83
tgggggatat gatggctct                                              19

<210> SEQ ID NO 84
<211> LENGTH: 30
<212> TYPE: DNA
<213> ORGANISM: Artificial Sequence
<220> FEATURE:
<223> OTHER INFORMATION: Probe

<400> SEQUENCE: 84
tgttacgtca awtggtasaa tttattgtat                                  30
```

```
<210> SEQ ID NO 85
<211> LENGTH: 30
<212> TYPE: DNA
<213> ORGANISM: Artificial Sequence
<220> FEATURE:
<223> OTHER INFORMATION: Probe

<400> SEQUENCE: 85
tgttacgtca awtggtasaa tttattgtac                                           30

<210> SEQ ID NO 86
<211> LENGTH: 17
<212> TYPE: DNA
<213> ORGANISM: Artificial Sequence
<220> FEATURE:
<223> OTHER INFORMATION: Probe

<400> SEQUENCE: 86
ctcttctatt ataccga                                                         17

<210> SEQ ID NO 87
<211> LENGTH: 17
<212> TYPE: DNA
<213> ORGANISM: Artificial Sequence
<220> FEATURE:
<223> OTHER INFORMATION: Probe

<400> SEQUENCE: 87
attgggggat atgatgg                                                         17

<210> SEQ ID NO 88
<211> LENGTH: 17
<212> TYPE: DNA
<213> ORGANISM: Artificial Sequence
<220> FEATURE:
<223> OTHER INFORMATION: Probe

<400> SEQUENCE: 88
attgggggat atgatga                                                         17

<210> SEQ ID NO 89
<211> LENGTH: 28
<212> TYPE: DNA
<213> ORGANISM: Artificial Sequence
<220> FEATURE:
<223> OTHER INFORMATION: Probe

<400> SEQUENCE: 89
gaatgtagaa gcatatgatc atcrtatg                                             28

<210> SEQ ID NO 90
<211> LENGTH: 27
<212> TYPE: DNA
<213> ORGANISM: Artificial Sequence
<220> FEATURE:
<223> OTHER INFORMATION: Probe

<400> SEQUENCE: 90
gggatatgat ggctcttcta ttatacc                                              27

<210> SEQ ID NO 91
<211> LENGTH: 27
<212> TYPE: DNA
<213> ORGANISM: Artificial Sequence
<220> FEATURE:
```

<223> OTHER INFORMATION: Probe

<400> SEQUENCE: 91
gggatatgat ggctcttcta ttatact                                                27

<210> SEQ ID NO 92
<211> LENGTH: 18
<212> TYPE: DNA
<213> ORGANISM: Artificial Sequence
<220> FEATURE:
<223> OTHER INFORMATION: Probe

<400> SEQUENCE: 92
agaagcatat gatcatcg                                                          18

<210> SEQ ID NO 93
<211> LENGTH: 19
<212> TYPE: DNA
<213> ORGANISM: Artificial Sequence
<220> FEATURE:
<223> OTHER INFORMATION: Probe

<400> SEQUENCE: 93
cttctattat accgaatgt                                                         19

<210> SEQ ID NO 94
<211> LENGTH: 19
<212> TYPE: DNA
<213> ORGANISM: Artificial Sequence
<220> FEATURE:
<223> OTHER INFORMATION: Probe

<400> SEQUENCE: 94
cttctattat accgaatgc                                                         19

<210> SEQ ID NO 95
<211> LENGTH: 18
<212> TYPE: DNA
<213> ORGANISM: Artificial Sequence
<220> FEATURE:
<223> OTHER INFORMATION: Probe

<400> SEQUENCE: 95
catatgatca tcgtatga                                                          18

<210> SEQ ID NO 96
<211> LENGTH: 18
<212> TYPE: DNA
<213> ORGANISM: Artificial Sequence
<220> FEATURE:
<223> OTHER INFORMATION: Probe

<400> SEQUENCE: 96
ttataccgaa tgtagaag                                                          18

<210> SEQ ID NO 97
<211> LENGTH: 18
<212> TYPE: DNA
<213> ORGANISM: Artificial Sequence
<220> FEATURE:
<223> OTHER INFORMATION: Probe

<400> SEQUENCE: 97
ttataccgaa tgtagaat                                                          18

```
<210> SEQ ID NO 98
<211> LENGTH: 18
<212> TYPE: DNA
<213> ORGANISM: Artificial Sequence
<220> FEATURE:
<223> OTHER INFORMATION: Probe

<400> SEQUENCE: 98
tatgaaagca tgggtaga                                                 18

<210> SEQ ID NO 99
<211> LENGTH: 17
<212> TYPE: DNA
<213> ORGANISM: Artificial Sequence
<220> FEATURE:
<223> OTHER INFORMATION: Probe

<400> SEQUENCE: 99
gaagcatatg atcatcg                                                  17

<210> SEQ ID NO 100
<211> LENGTH: 17
<212> TYPE: DNA
<213> ORGANISM: Artificial Sequence
<220> FEATURE:
<223> OTHER INFORMATION: Probe

<400> SEQUENCE: 100
gaagcatatg atcatca                                                  17

<210> SEQ ID NO 101
<211> LENGTH: 17
<212> TYPE: DNA
<213> ORGANISM: Artificial Sequence
<220> FEATURE:
<223> OTHER INFORMATION: Probe

<400> SEQUENCE: 101
agcatgggta gaggtgg                                                  17

<210> SEQ ID NO 102
<211> LENGTH: 19
<212> TYPE: DNA
<213> ORGANISM: Artificial Sequence
<220> FEATURE:
<223> OTHER INFORMATION: Probe

<400> SEQUENCE: 102
catatgatca tcgtatgaa                                                19

<210> SEQ ID NO 103
<211> LENGTH: 19
<212> TYPE: DNA
<213> ORGANISM: Artificial Sequence
<220> FEATURE:
<223> OTHER INFORMATION: Probe

<400> SEQUENCE: 103
catatgatca tcgtatgag                                                19

<210> SEQ ID NO 104
<211> LENGTH: 23
<212> TYPE: DNA
<213> ORGANISM: Artificial Sequence
<220> FEATURE:
<223> OTHER INFORMATION: Probe
```

```
<400> SEQUENCE: 104
ggcacctttg aatacccyta gat                                          23

<210> SEQ ID NO 105
<211> LENGTH: 23
<212> TYPE: DNA
<213> ORGANISM: Artificial Sequence
<220> FEATURE:
<223> OTHER INFORMATION: Probe

<400> SEQUENCE: 105
crtatgaaag catgggtaga ggt                                          23

<210> SEQ ID NO 106
<211> LENGTH: 23
<212> TYPE: DNA
<213> ORGANISM: Artificial Sequence
<220> FEATURE:
<223> OTHER INFORMATION: Probe

<400> SEQUENCE: 106
crtatgaaag catgggtaga ggg                                          23

<210> SEQ ID NO 107
<211> LENGTH: 18
<212> TYPE: DNA
<213> ORGANISM: Artificial Sequence
<220> FEATURE:
<223> OTHER INFORMATION: Probe

<400> SEQUENCE: 107
tagatcatca gctatgtg                                                18

<210> SEQ ID NO 108
<211> LENGTH: 17
<212> TYPE: DNA
<213> ORGANISM: Artificial Sequence
<220> FEATURE:
<223> OTHER INFORMATION: Probe

<400> SEQUENCE: 108
gcacctttga atacccc                                                 17

<210> SEQ ID NO 109
<211> LENGTH: 17
<212> TYPE: DNA
<213> ORGANISM: Artificial Sequence
<220> FEATURE:
<223> OTHER INFORMATION: Probe

<400> SEQUENCE: 109
gcacctttga ataccct                                                 17

<210> SEQ ID NO 110
<211> LENGTH: 17
<212> TYPE: DNA
<213> ORGANISM: Artificial Sequence
<220> FEATURE:
<223> OTHER INFORMATION: Probe

<400> SEQUENCE: 110
ctatgtgtgt tgctttt                                                 17

<210> SEQ ID NO 111
<211> LENGTH: 17
```

```
<212> TYPE: DNA
<213> ORGANISM: Artificial Sequence
<220> FEATURE:
<223> OTHER INFORMATION: Probe

<400> SEQUENCE: 111
gacccctaga tcatcag                                                17

<210> SEQ ID NO 112
<211> LENGTH: 17
<212> TYPE: DNA
<213> ORGANISM: Artificial Sequence
<220> FEATURE:
<223> OTHER INFORMATION: Probe

<400> SEQUENCE: 112
gacccctaga tcatcat                                                17

<210> SEQ ID NO 113
<211> LENGTH: 28
<212> TYPE: DNA
<213> ORGANISM: Artificial Sequence
<220> FEATURE:
<223> OTHER INFORMATION: Probe

<400> SEQUENCE: 113
tgttgctttt gwtaataaaa tttatgtc                                    28

<210> SEQ ID NO 114
<211> LENGTH: 26
<212> TYPE: DNA
<213> ORGANISM: Artificial Sequence
<220> FEATURE:
<223> OTHER INFORMATION: Probe

<400> SEQUENCE: 114
aatacccyta gatcatcagc tatgtg                                      26

<210> SEQ ID NO 115
<211> LENGTH: 26
<212> TYPE: DNA
<213> ORGANISM: Artificial Sequence
<220> FEATURE:
<223> OTHER INFORMATION: Probe

<400> SEQUENCE: 115
aatacccyta gatcatcagc tatgta                                      26

<210> SEQ ID NO 116
<211> LENGTH: 23
<212> TYPE: DNA
<213> ORGANISM: Artificial Sequence
<220> FEATURE:
<223> OTHER INFORMATION: Probe

<400> SEQUENCE: 116
tgataataaa atttatgtca ttg                                         23

<210> SEQ ID NO 117
<211> LENGTH: 16
<212> TYPE: DNA
<213> ORGANISM: Artificial Sequence
<220> FEATURE:
<223> OTHER INFORMATION: Probe

<400> SEQUENCE: 117
```

```
ctatgtgtgt tgcttt                                                    16

<210> SEQ ID NO 118
<211> LENGTH: 16
<212> TYPE: DNA
<213> ORGANISM: Artificial Sequence
<220> FEATURE:
<223> OTHER INFORMATION: Probe

<400> SEQUENCE: 118
ctatgtgtgt tgcttc                                                    16

<210> SEQ ID NO 119
<211> LENGTH: 16
<212> TYPE: DNA
<213> ORGANISM: Artificial Sequence
<220> FEATURE:
<223> OTHER INFORMATION: Probe

<400> SEQUENCE: 119
ctatgtgtgt tgctta                                                    16

<210> SEQ ID NO 120
<211> LENGTH: 24
<212> TYPE: DNA
<213> ORGANISM: Artificial Sequence
<220> FEATURE:
<223> OTHER INFORMATION: Probe

<400> SEQUENCE: 120
htgataataa aatttatgtc attg                                           24

<210> SEQ ID NO 121
<211> LENGTH: 15
<212> TYPE: DNA
<213> ORGANISM: Artificial Sequence
<220> FEATURE:
<223> OTHER INFORMATION: Probe

<400> SEQUENCE: 121
ctatgtgtgt tgctt                                                     15

<210> SEQ ID NO 122
<211> LENGTH: 15
<212> TYPE: DNA
<213> ORGANISM: Artificial Sequence
<220> FEATURE:
<223> OTHER INFORMATION: Probe

<400> SEQUENCE: 122
ctatgtgtgt tgctc                                                     15

<210> SEQ ID NO 123
<211> LENGTH: 21
<212> TYPE: DNA
<213> ORGANISM: Artificial Sequence
<220> FEATURE:
<223> OTHER INFORMATION: Probe

<400> SEQUENCE: 123
taataaaatt tatgtcattg g                                              21

<210> SEQ ID NO 124
<211> LENGTH: 17
<212> TYPE: DNA
<213> ORGANISM: Artificial Sequence
```

```
<220> FEATURE:
<223> OTHER INFORMATION: Probe

<400> SEQUENCE: 124
atgtgtgttg cttttga                                                      17

<210> SEQ ID NO 125
<211> LENGTH: 17
<212> TYPE: DNA
<213> ORGANISM: Artificial Sequence
<220> FEATURE:
<223> OTHER INFORMATION: Probe

<400> SEQUENCE: 125
atgtgtgttg cttttgt                                                      17

<210> SEQ ID NO 126
<211> LENGTH: 19
<212> TYPE: DNA
<213> ORGANISM: Artificial Sequence
<220> FEATURE:
<223> OTHER INFORMATION: Probe

<400> SEQUENCE: 126
tcattggtgg aactaatgg                                                    19

<210> SEQ ID NO 127
<211> LENGTH: 22
<212> TYPE: DNA
<213> ORGANISM: Artificial Sequence
<220> FEATURE:
<223> OTHER INFORMATION: Probe

<400> SEQUENCE: 127
gcttttgata ataaaattta tg                                                22

<210> SEQ ID NO 128
<211> LENGTH: 22
<212> TYPE: DNA
<213> ORGANISM: Artificial Sequence
<220> FEATURE:
<223> OTHER INFORMATION: Probe

<400> SEQUENCE: 128
gcttttgata ataaaattta ta                                                22

<210> SEQ ID NO 129
<211> LENGTH: 18
<212> TYPE: DNA
<213> ORGANISM: Artificial Sequence
<220> FEATURE:
<223> OTHER INFORMATION: Probe

<400> SEQUENCE: 129
aatttccata tgccttat                                                     18

<210> SEQ ID NO 130
<211> LENGTH: 19
<212> TYPE: DNA
<213> ORGANISM: Artificial Sequence
<220> FEATURE:
<223> OTHER INFORMATION: Probe

<400> SEQUENCE: 130
aaaatgaata aatgggaac                                                    19
```

```
<210> SEQ ID NO 131
<211> LENGTH: 19
<212> TYPE: DNA
<213> ORGANISM: Artificial Sequence
<220> FEATURE:
<223> OTHER INFORMATION: Probe

<400> SEQUENCE: 131
aaaatgaata aatgggaag                                                  19

<210> SEQ ID NO 132
<211> LENGTH: 20
<212> TYPE: DNA
<213> ORGANISM: Artificial Sequence
<220> FEATURE:
<223> OTHER INFORMATION: Probe

<400> SEQUENCE: 132
taatgaacat aacatattag                                                 20

<210> SEQ ID NO 133
<211> LENGTH: 17
<212> TYPE: DNA
<213> ORGANISM: Artificial Sequence
<220> FEATURE:
<223> OTHER INFORMATION: Probe

<400> SEQUENCE: 133
gttgttggag gtattga                                                    17

<210> SEQ ID NO 134
<211> LENGTH: 17
<212> TYPE: DNA
<213> ORGANISM: Artificial Sequence
<220> FEATURE:
<223> OTHER INFORMATION: Probe

<400> SEQUENCE: 134
gttgttggag gtattgg                                                    17
```

MOLECULAR MARKER OF PLASMODIUM FALCIPARUM ARTEMISININ RESISTANCE

SEQUENCE LISTING

The sequence listing submitted herewith as an ASCII text file is named Listing.txt, was created on Dec. 16, 2020, is 68,819 byes in size, and is hereby incorporated herein by reference.

SEQUENCE LISTING

The sequence listing submitted herewith as an ASCII text file is named Listing.txt, was created on Dec. 16, 2020, is 68,819 byes in size, and is hereby incorporated herein by reference.

BACKGROUND OF THE INVENTION

The emergence of *Plasmodium falciparum* resistance to artemisinin derivatives (ART) in Cambodia threatens the world's malaria control and elimination efforts[1,2] The risk of ART-resistant parasites spreading from Western Cambodia to the Greater Mekong Subregion and to Africa, as happened previously with chloroquine- and sulfadoxine/pyrimethamine-resistant parasites[3-5], is extremely worrisome. Clinical ART resistance is defined as a reduced parasite clearance rate[1,6-10], expressed as an increased parasite clearance half-life[11,12], or a persistence of microscopically-detectable parasites on the third day of artemisinin-based combination therapy (ACT)[2]. The half-life parameter correlates strongly with results from the in vitro Ring-stage Survival Assay ($RSA^{0-3h}$) and the ex vivo $RSA^{13}$, which measure the survival rate of young ring-stage parasites to a pharmacologically-relevant exposure (700 nM for 6 h) to dihydroartemisinin (DHA)—the major metabolite of all ARTs. However, the present lack of a molecular marker hampers focused containment of ART-resistant parasites in areas where they have been documented and hinders rapid detection of these parasites elsewhere, where ACTs remain the most affordable, effective antimalarials. To detect and monitor the spread of ART resistance, a molecular marker for widespread use is needed.

Recent genome-wide analyses of *P. falciparum* isolates have provided evidence of recent positive selection in geographic areas of ART resistance[9, 14-16]. While parasite heritability of the clinical phenotype is above 50%, no reliable molecular marker has yet been identified. One possible explanation is that the parasite clearance half-life is not only determined by the intrinsic susceptibility of a parasite isolate to ART, but also by its developmental stage at the time of ART treatment and host-related parameters such as pharmacokinetics and immunity[17]. This issue was recently highlighted in patients presenting discordant data between parasite clearance half-life in vivo and $RSA^{0-3h}$ survival rate in vitro[13]. Moreover, genome-wide association studies (GWAS) are confounded by uncertainties about parasite population structure. Recent evidence for several highly-differentiated subpopulations of ART-resistant parasites in Western Cambodia[15] suggests that distinct emergence events might be occurring. An alternative strategy to discover a molecular marker is to analyze mutations acquired specifically by laboratory-adapted parasite clones selected to survive high doses of ART in vitro, and use this information to guide analysis of polymorphism in clinical parasite isolates from areas where ART resistance is well documented at both temporal and geographical levels. Here we used this strategy to explore the molecular signatures of clinical ART resistance in Cambodia, where this phenotype was first reported[1, 8].

Artemisinin-based combination therapies (ACTs) are a key facet of global malaria control efforts. Nkhoma et al., JID 208:346-349 (2013). However, the emergence of artemisinin-resistant malaria has threatened these efforts. Id. There are currently no reliable in vitro tests for measuring ART resistance. Id. Therefore, ART sensitivity has been measured in patients from the decline of parasitemia following ART treatment. Id. This approach is expensive, labor-intensive, and time-consuming. Id.

The current lack of a molecular marker hampers containment efforts in the foci where resistance has been documented and hinders rapid detection of ART-resistance in other endemic areas where ART remains the most affordable and efficient antimalarial drug. To monitor ART-resistance at a large scale, a molecular marker associated with ART-resistance is urgently needed. The current invention fulfills this need in the art.

SUMMARY OF THE INVENTION

The invention encompasses methods, compositions, and kits for detecting and genotyping *Plasmodium*. In one embodiment, the method comprises providing a sample containing a *Plasmodium*; and detecting the presence of a mutated K-13 propeller nucleic acid or protein in the sample. Preferably, the *Plasmodium* is *Plasmodium falciparum*.

In one embodiment, the presence of a mutated K-13 propeller nucleic acid in the sample is detected by sequencing. In one embodiment, the presence of a mutated K-13 propeller nucleic acid in the sample is detected by PCR.

The invention encompasses methods, compositions and kits for the detection of a *Plasmodium* infection in an infected patient. In one embodiment, the method comprises providing a blood sample from a patient and detecting the presence or absence of a wild-type or mutated K-13 propeller nucleic acid or protein in the blood sample. The method can comprise determining whether the *Plasmodium* has a wild-type or mutant K-13 propeller nucleic acid or protein sequence.

Preferably, the *Plasmodium* is *Plasmodium falciparum*.

In one embodiment, the presence of a mutated K-13 propeller nucleic acid in the sample is detected by sequencing. In one embodiment, the presence or absence of a wild-type or mutated K-13 propeller nucleic acid in the sample is detected by PCR.

In one embodiment, the kit for detecting a *Plasmodium* infection comprises primers for the amplification of a K-13 propeller nucleic acid and reagents for the detection of the amplified product.

In one embodiment, the kit contains a probe for detecting a mutant K-13 propeller nucleic acid. Preferably, the probe is labeled with a fluorescent or enzymatic label.

In various embodiments, the kit detects a mutant K-13 propeller nucleic acid encoding a Y493H, R539T, I543T, and C580Y allele.

In an embodiment the kit detects a mutant K-13 propeller nucleic acid encoding a Y493H, R539T, I543T or C580Y allele.

In various embodiments, the kit comprises at least one of the following primers:
5'-cggagtgaccaaatctggga-3' (SEQ ID NO:9);
5'-gggaatctggtggtaacagc-3' (SEQ ID NO:10);
5'-cgccagcattgttgactaat-3' (SEQ ID NO:11); and
5'-gcggaagtagtagcgagaat-3' (SEQ ID NO:12);

or the kit comprises at least one of the following primers:
5'-cggagtgaccaaatctggga-3' (SEQ ID NO:9);
5'-gggaatctggtggtaacagc-3' (SEQ ID NO:10);
5'-cgccagcattgttgactaat-3' (SEQ ID NO:11);
5'-gcggaagtagtagcgagaat-3' (SEQ ID NO:12);
5'-gccaagctgccattcatttg-3' (SEQ ID NO:13); and
5'-gccttgttgaaagaagcaga-3' (SEQ ID NO:14).

In various embodiments, the kit detects a mutant K13 propeller nucleic acid encoding a F446I, N458Y, C469Y, Y493H, K503N, R539T, I543T, P553L, P574L, A578S, C580Y, and D584V allele.

In various embodiments, the kit detects a mutant K13 propeller nucleic acid encoding a F446I, G449A, N458Y, C469Y, W470stop, A481V, Y493H, K503N, S522C, V534A, R539T, I543T, G548D, P553L, V555A, A557S, R561H, K563R, V568G, P574L, A578S, C580Y, F583L, D584V, V589I, Q613E, and D641G allele.

In various embodiments, the kit comprises at least one of the following pairs of primers:
Pair PCR1
5' aggtggatttgatggtgtagaat 3' (forward) (SEQ ID NO:15)
5' catacacctcagtttcaaataaagc 3' (reverse) (SEQ ID NO:16)
Pair PCR2
5' aatttcttatacgtttttggtggtaa 3' (forward) (SEQ ID NO:17)
5' ctctacccatgctttcatacgat 3' (reverse) (SEQ ID NO:18)
Pair PCR3
5' ggatatgatggctcttctattataccg 3' (forward) (SEQ ID NO:19)
5' acttcaatagaatttaatctctcacca 3' (reverse) (SEQ ID NO:20)
Pair PCR4
5' atgtcattggtggaactaatggt 3' (forward) (SEQ ID NO:21)
5' ttaaatggttgatattgttcaacg 3' (reverse) (SEQ ID NO:22)
Pair PCR5
5' ttcaggagcagcttttaattacc 3' (forward) (SEQ ID NO:23)
5' ctggtgaaaagaaatgacatgaa 3' (reverse) (SEQ ID NO:24)
Pair PCR6
5' ccttgttgaaagaagcagaattt 3' (forward) (SEQ ID NO:25)
5' attcaatacagcacttccaaaataa 3' (reverse) (SEQ ID NO:26)

In various embodiments, the kit comprises at least one probe hybridizing with one of the following SNP:
F446I ttt/att
G449A ggt/gct
N458Y aat/tat
C469Y tgc/tac
W470stop tgg/tga
A481V gct/gtt
Y493H tac/cac
K503N aag/aat
S522C agt/tgt
V534A gtt/gct
R539T aga/aca
I543T att/act
G548D ggc/gac
P553L ccg/ctg
V555A gta/gca
A557S gca/tca
R561H cgt/cat
K563R aaa/aga
V568G gtg/ggg
P574L cct/ctt
A578S gct/tct
C580Y tgt/tat
F583L ttt/tta/g
D584V gat/gtt
V589I gtc/atc
Q613E caa/gaa
D641G gat/ggt.

The invention encompasses a method for detecting in a biological sample containing *Plasmodium* the presence of a wild-type K13 propeller nucleic acid or a mutant K13 propeller nucleic acid comprising:
providing a biological sample containing DNA of *Plasmodium*;
optionally extracting DNA from the biological sample;
contacting the DNA of *Plasmodium* with at least one pair of primers which hybridize specifically with the K13 propeller nucleic acid at a distance ranging from 100 to 300 bp and performing a PCR reaction in the presence of intercalating dye;
subjecting amplification products to a melting step;
determining the presence of a mutant allele or a wild type allele by analyzing the melting profile of the amplification products.

In some embodiments, the method comprises detecting a mutant K13 propeller nucleic acid encoding a F446I, G449A, N458Y, C469Y, W470stop, A481V, Y493H, K503N, S522C, V534A, R539T, I543T, G548D, P553L, V555A, A557S, R561H, K563R, V568G, P574L, A578S, C580Y, F583L, D584V, V589I, Q613E, and D641G allele.

The invention encompasses a method for detecting in a biological sample containing *Plasmodium* the presence of a mutant K13 propeller nucleic acid comprising amplifying the mutant K13 propeller nucleic acid by PCR reaction, and contacting the amplified nucleic acid with a probe specific for a mutant K13 propeller nucleic acid.

In some embodiments, the probe is bound to a fluorescent bead or biotin.

In some embodiments, the method comprises binding the probe to the mutant K13 propeller domain nucleic acid and detecting the bound K13 propeller domain nucleic acid with a second probe that binds to the bound K13 propeller domain nucleic acid.

In some embodiments, the presence of a mutated K13 propeller nucleic acid or protein indicates that the patient is infected with a *Plasmodium* resistant to artemisinin derivatives.

In some embodiments, the method comprises administering to said patient infected with a *Plasmodium* resistant to artemisinin derivatives a treatment based on artemisinin derivatives longer than the routine protocol, and/or another anti-malarial drug, preferably quinine, chloroquine or mefloquine.

In some embodiments, the method comprises administering to said patient infected with a *Plasmodium* resistant to artemisinin derivatives a treatment based on a new antimalarial drug, and repeating steps a) and b) after administering said treatment, wherein the absence of a mutated K13 propeller nucleic acid or protein indicates that the patient is no longer infected with a *Plasmodium* resistant to artemisinin derivatives and said treatment is efficient on a *Plasmodium* resistant to artemisinin derivatives.

Figure 2:
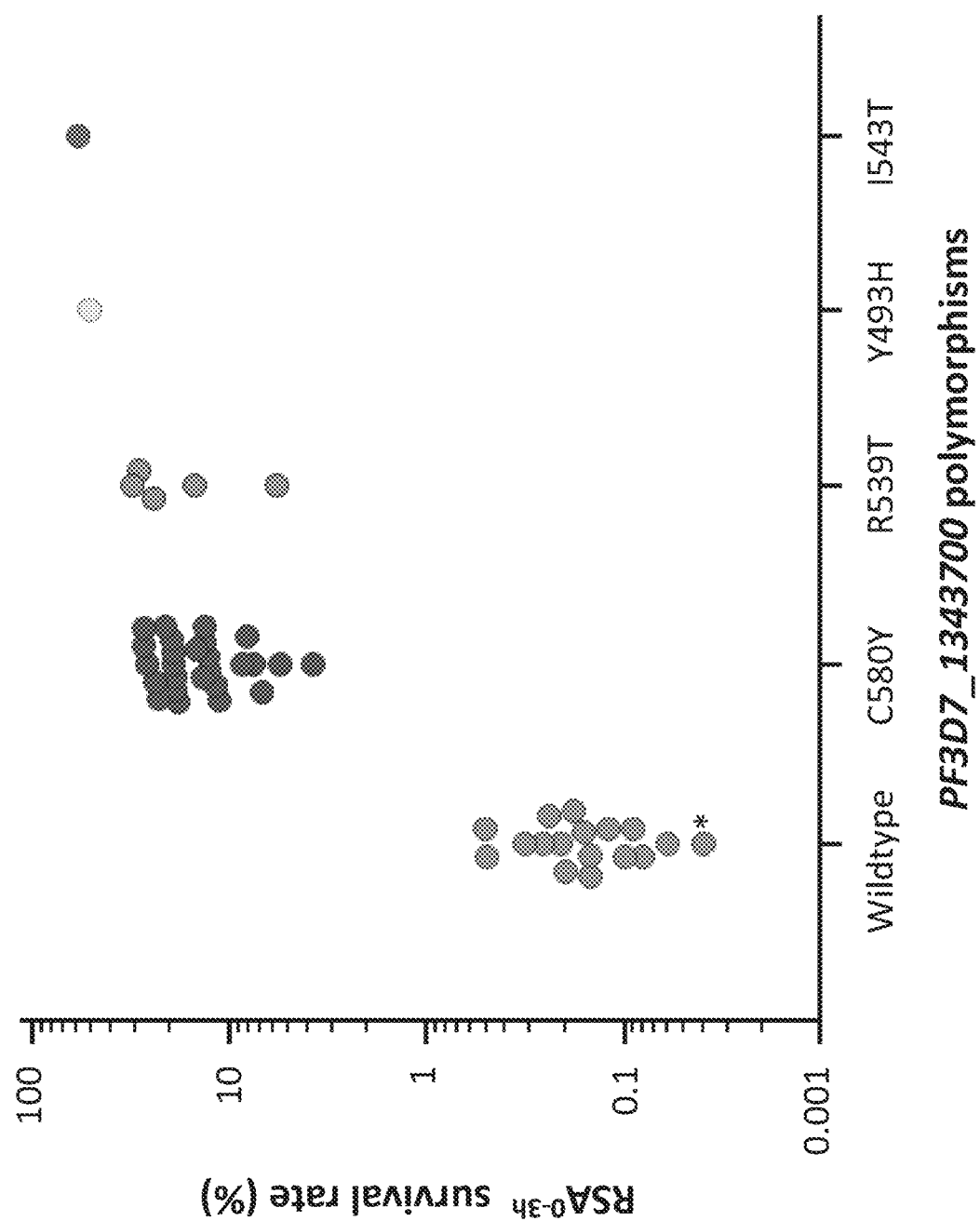

FIG. 2—Survival rates of Cambodian parasite isolates in the RSA$^{0-3h}$, stratified by K13-propeller allele. Genotypes were obtained by mining whole-genome sequence data (n=21) or sequencing PCR products (n=28). Mutant parasites have significantly higher RSA$^{0-3h}$ survival rates than wildtype parasites: wildtype (n=17, median 0.16%, IQR 0.09-0.24, range 0.04-0.51); C580Y (n=26, median 14.1%, IQR 11.3-19.6, range 3.8-27.3, P<10$^{-6}$ for wildtype vs. C580Y, Mann-Whitney U test); R539T (n=5, median 24.2%, IQR 12.6-29.5, range 5.8-31.3, P<10$^{-3}$ for wildtype vs. R539T); Y493H (51.4%); and I543T (58.0%). The RSA$^{0-3h}$ survival rate (0.04%) of control 3D7 parasites is indicated by an asterisk.

Figure 3:
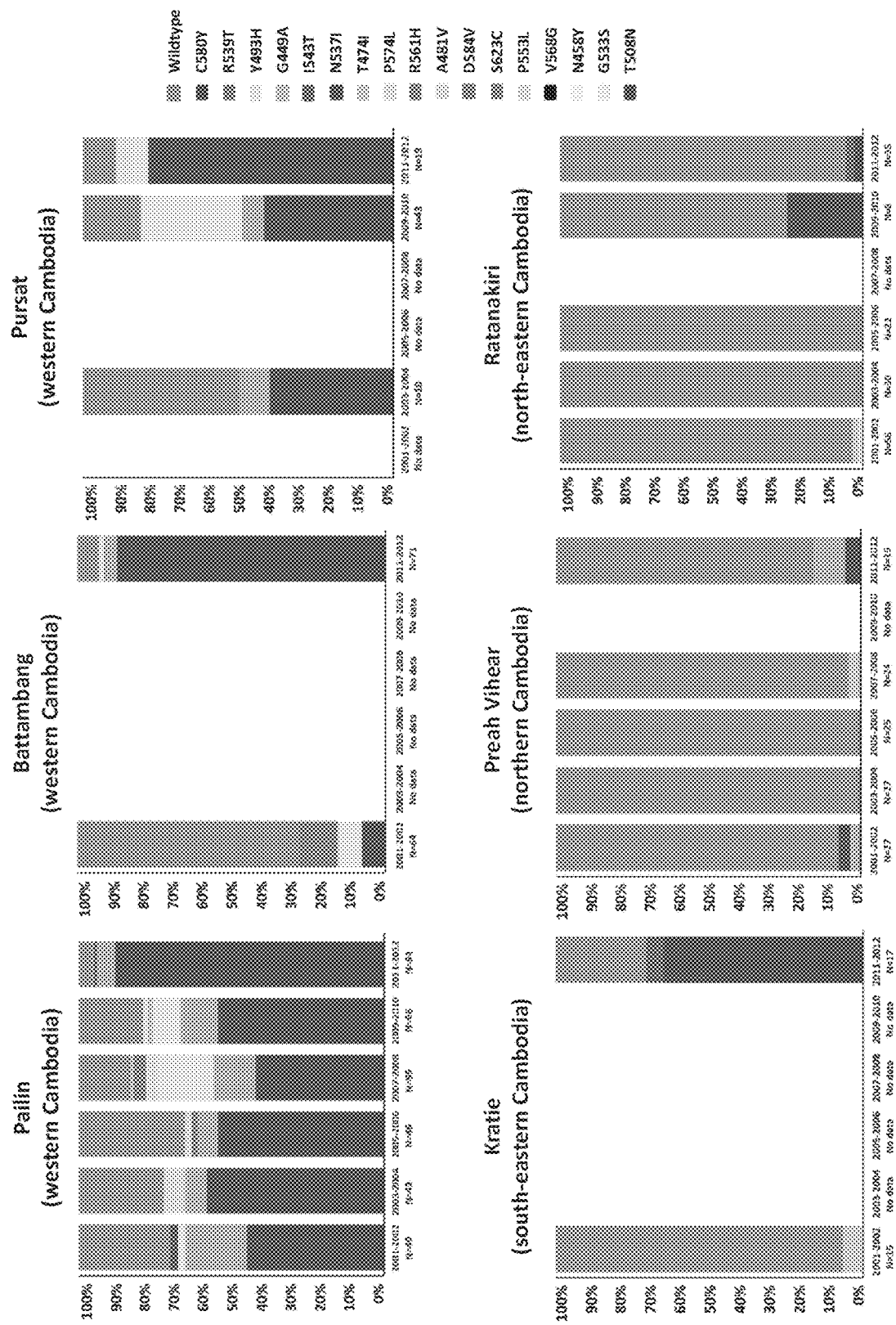

FIG. 3—Frequency of K13-propeller alleles in 886 parasite isolates in six Cambodian provinces in 2001-2012. Genotypes were obtained by sequencing PCR products from archived blood samples. All mutant alleles carry a single non-synonymous SNP (color-coded, same color-codes as in FIG. 2 for wildtype, C580Y, R539T, Y493H and I543T). Significant reductions (Fisher's exact test) in wildtype allele frequencies were observed in Pailin, Battambang, Pursat and Kratie over time (see Examples).

Figure 4A:
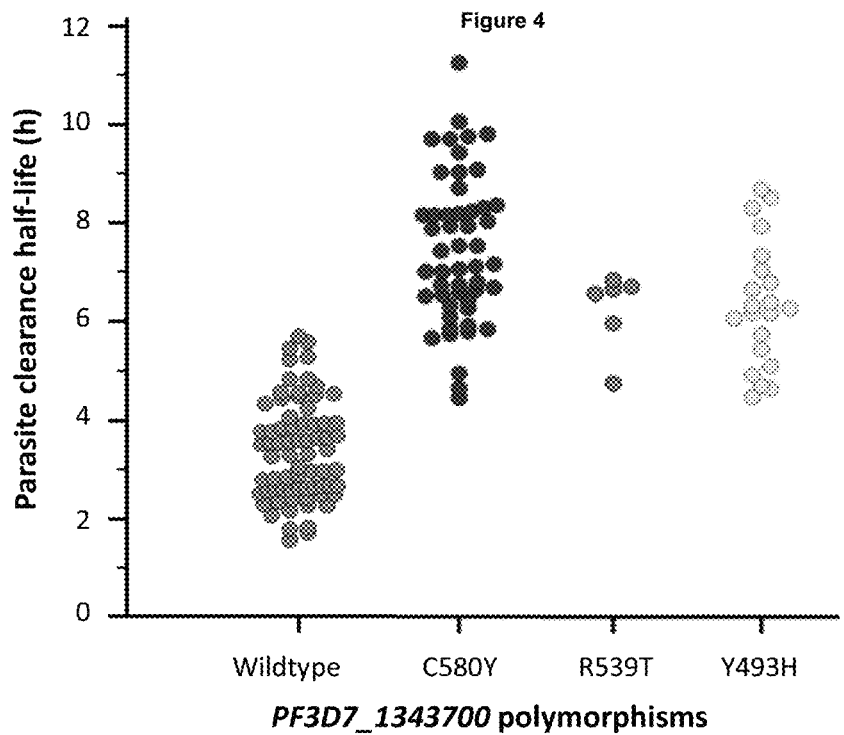
Figure 4B:
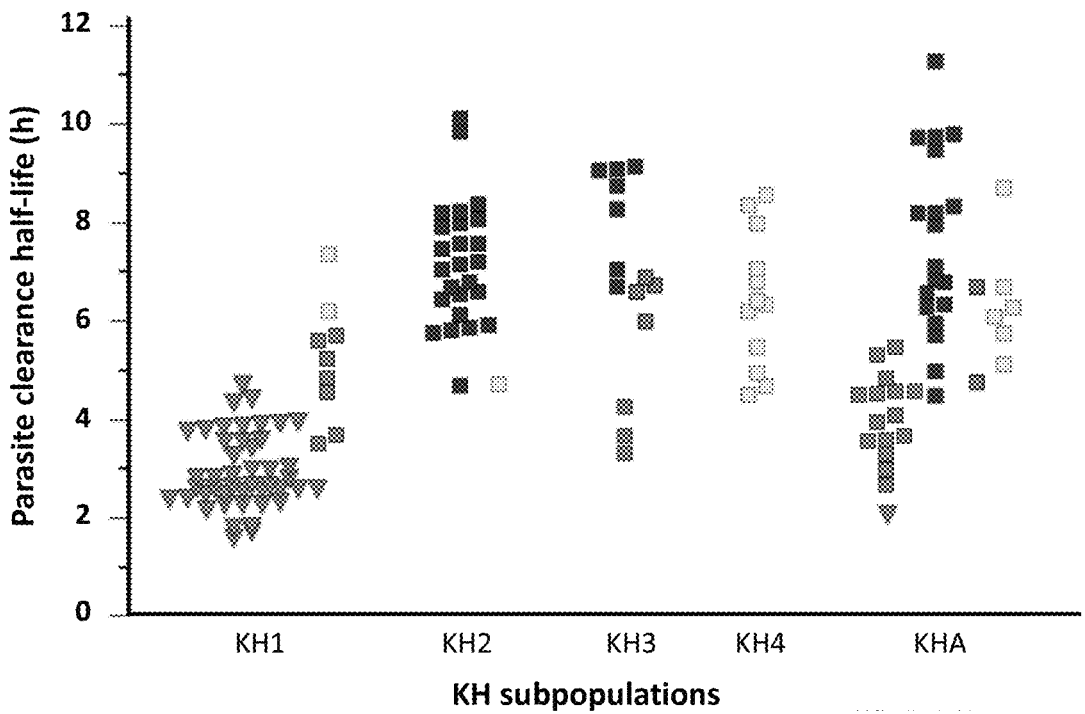

FIGS. 4A to 4B—A, Correlation of parasite clearance half-lives and K13-propeller alleles for parasite isolates in Pursat and Ratanakiri in 2009-2010. Wildtype parasites have shorter half-lives (median 3.30 h, IQR 2.59-3.95, n=72) than C580Y (7.19 h, 6.47-8.31, n=51, P<10$^{-6}$, Mann-Whitney U test), R539T (6.64 h, 6.00-6.72, n=6, P<10$^{-6}$) or Y493H (6.28 h, 5.37-7.14, n=21, P<10$^{-6}$) parasites. The half-life of C580Y parasites is significantly longer than that of Y493H parasites (P=0.007). B, Correlation of parasite clearance half-lives, KH subpopulations[15] and K13-propeller alleles for the same 150 parasite isolates. Half-lives are shown for Pursat (squares) and Ratanakiri (triangles) parasites, stratified by KH group and K13-propeller allele (color-coded as in panel A). Median half-lives stratified by K13-propeller allele are: [KH1: wildtype (2.88) and Y493H (6.77); KH2: C580Y (7.13) and Y493H (4.71); KH3: wildtype (3.65), C580Y (8.73) and R539T (6.65); KH4: Y493H (6.37); and KHA: wildtype (4.01), C580Y (7.09), Y493H (6.18) and R539T (5.73)].

Figures 5A, 5B:
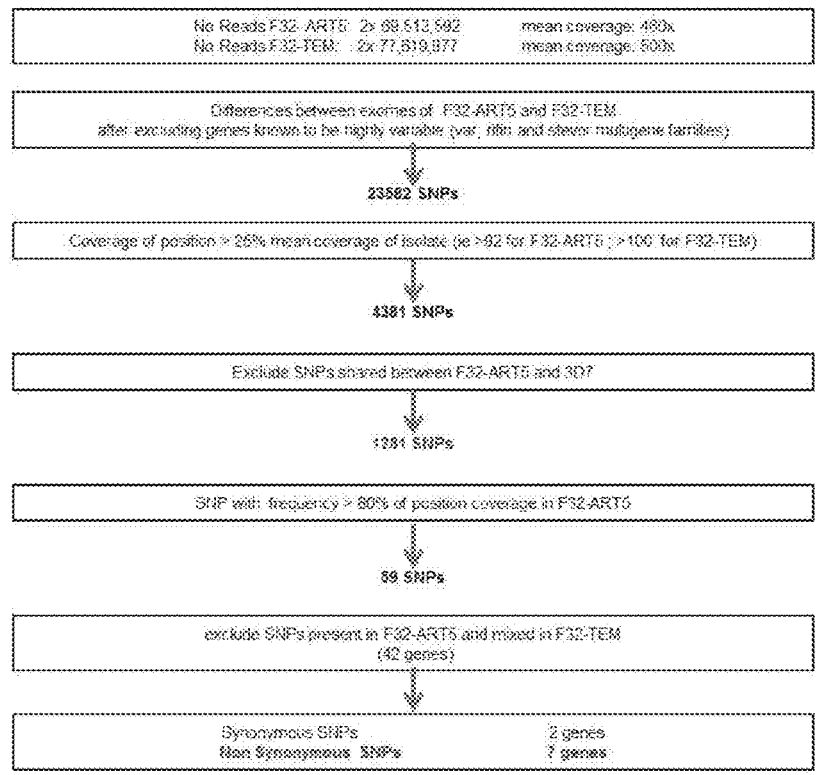

FIGS. 5A to 5B—SNP-calling algorithm of the whole-genome sequence comparison of F32-ART5 and F32-TEM (a), and sequence and coverage of SNPs in 7 candidate genes differing in F32-TEM and F-32 ART5 (b).

Figure 6:
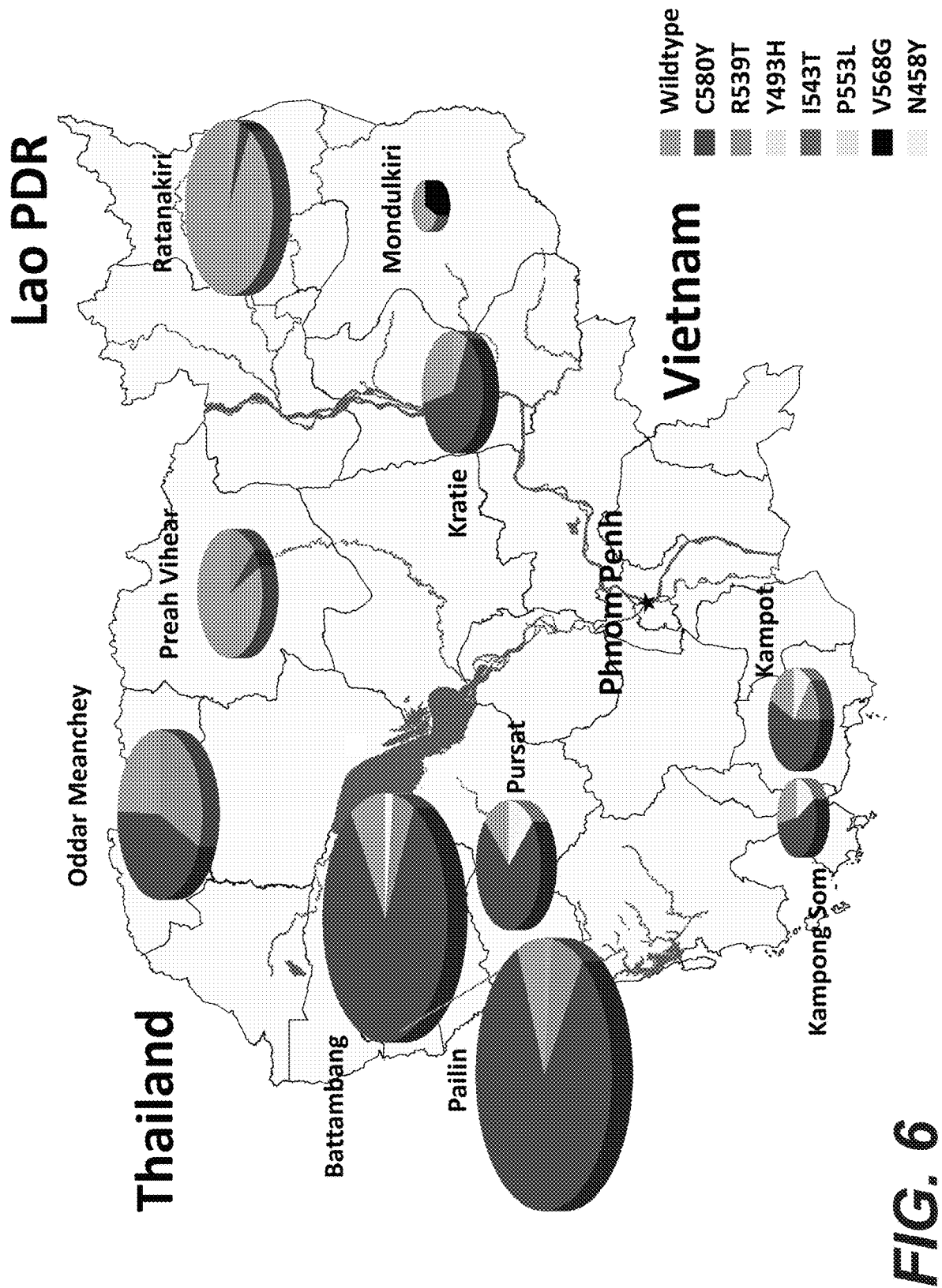

FIG. 6—Geographic distribution of K13-propeller alleles in Cambodia in 2011-2012.

Pie charts show K13-propeller allele frequencies among 300 parasite isolates in ten Cambodian provinces. Pie sizes are proportional to the number of isolates and the different alleles are color-coded as in FIG. 3. The frequencies (95% CI) of mutant K13-propeller alleles are: Pailin (95%, 88-99, n=84), Battambang (93%, 87-99, n=71), Pursat (89%, 67-99, n=19), Kampot (83%, 52-98, n=12), Kampong Som (71%, 29-96, n=7), Oddar Meanchey (76%, 58-89, n=33), Preah Vihear (16%, 3-40, n=19), Kratie (71%, 44-90, n=17), Mondulkiri (67%, 9-99, n=3) and Ratanakiri (6%, 1-19, n=35).

Figure 7:
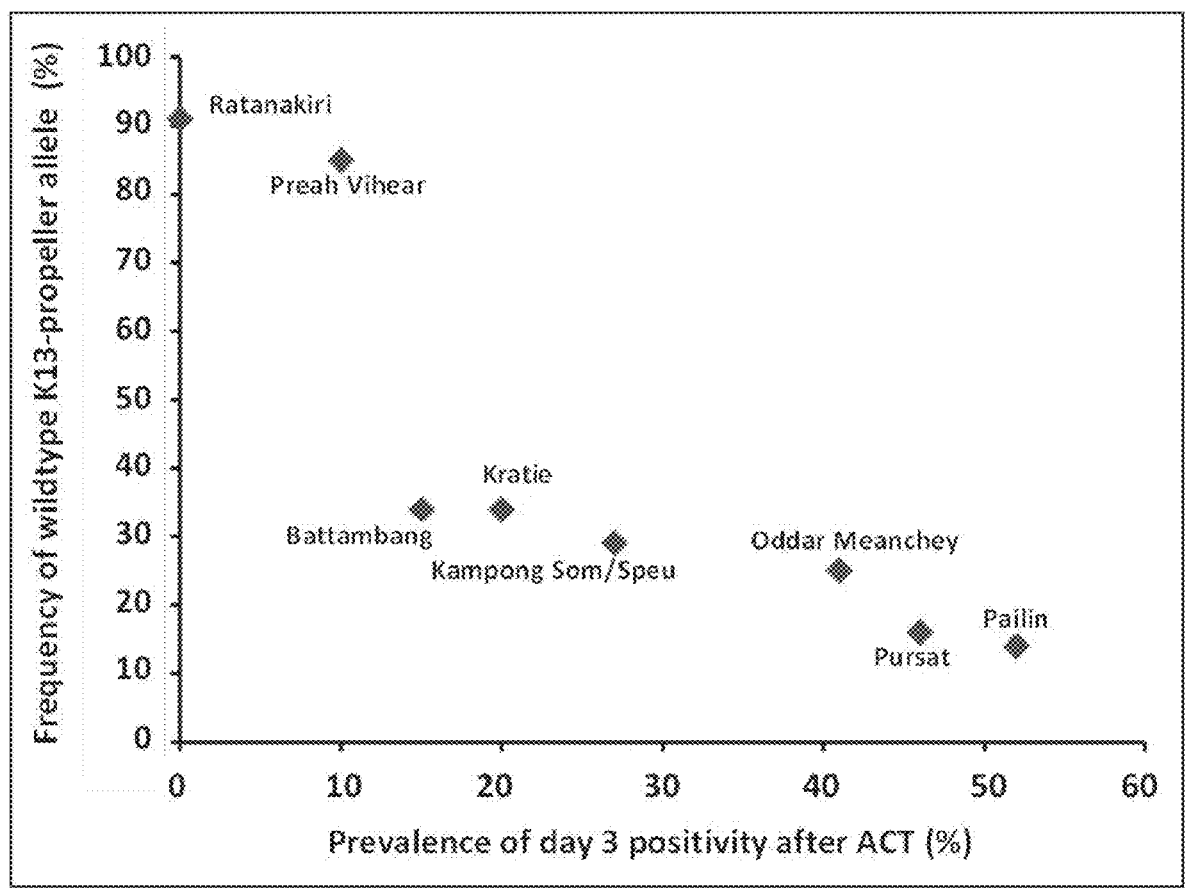

FIG. 7—Correlation between the frequency of wildtype K13-propeller alleles and the prevalence of day 3 positivity after ACT treatment in eight Cambodian provinces.

The frequency of day 3 positivity is plotted against the frequency of wildtype K13-propeller alleles. Data are derived from patients treated with an ACT for P. falciparum malaria in 2010-2012 in eight Cambodian provinces (FIG. 4): Pailin (n=86, 2011 WHO therapeutic efficacy study, artesunate-mefloquine); Pursat (n=32, 2012 WHO therapeutic efficacy study, dihydroartemisinin-piperaquine); Oddar Meanchey (n=32, 2010 NAMRU-2 therapeutic efficacy study, artesunate-mefloquine); Kampong Som/Speu (n=7, 2012 WHO therapeutic efficacy study, dihydroartemisinin-piperaquine); Battambang (n=18, 2012 WHO therapeutic efficacy study, dihydroartemisinin-piperaquine); Kratie (n=15, 2011 WHO therapeutic efficacy study, dihydroartemisinin-piperaquine); Preah Vihear (n=19, 2011 WHO therapeutic efficacy study, dihydroartemisinin-piperaquine); Ratanakiri (n=32, 2010 WHO therapeutic efficacy study, dihydroartemisinin-piperaquine). Spearman's coefficient of rank correlation (8 sites): r=−0.99, 95% CI −0.99 to −0.96, P<0.0001.

Figure 8A:
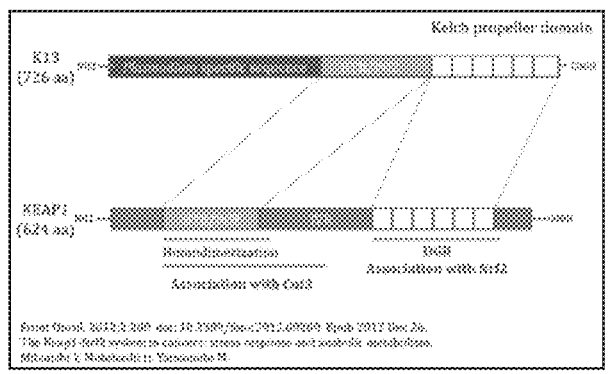
Figure 8B:
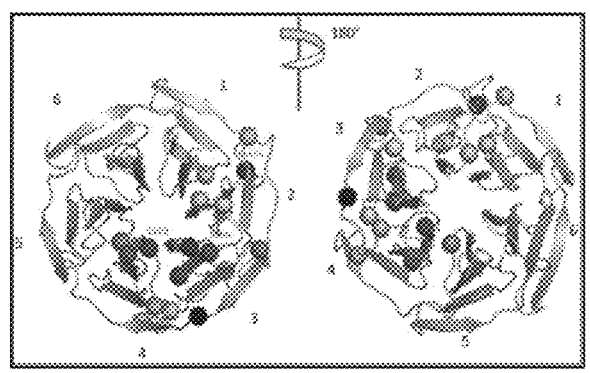

FIGS. 8A and 8B—Schematic representation of homology between P. falciparum K13 and human KEAP1 proteins (A) and structural 3D-model of the K13-propeller domain (B).

A. Schematic representation of the predicted PF3D7_1343700 protein and homology to human Keap1. Similar to Keap1, PF3D7_1343700 contains a BTB/POZ domain and a C-terminal 6-blade propeller, which assembles kelch motifs consisting of four anti-parallel beta sheets. B. Structural 3D-model of the K13-propeller domain showing the six kelch blades numbered 1 to 6 from N- to C-terminus.

The level of amino-acid identity between the K13-propeller and kelch domains of proteins with solved 3D-structures, including human Keap1[46,47], enabled us to model the 3D-structure of the K13-propeller and to map the mutations selected under ART pressure (Table 4). The accuracy of the K13-propeller 3D-model was confirmed by Modeller-specific model/fold criteria of reliability (see Examples). We predict that the K13-propeller folds into a six-bladed β-propeller structure[48] closed by the interaction between a C-terminal beta-sheet and the N-terminal blade[46,45]. The first domain has three beta sheets, the 4$^{th}$ one being contributed by an extra C-terminal beta sheet called β'1 in FIG. 9.

The human Keap1 kelch propeller scaffold is destabilized by a variety of mutations affecting intra- or inter-blade interactions in human lung cancer[46] and hypertension[47]. The positions of the various mutations are indicated by a sphere. The M476 residue mutated in F32-ART5 is indicated in dark grey. Like the mutations observed in human Keap1[46,47], many K13-propeller mutations are predicted to alter the structure of the propeller or modify surface charges, and as a consequence alter the biological function of the protein. Importantly, the two major mutations C580Y and R539T observed in Cambodia are both non-conservative and located in organized secondary structures: a p-sheet of blade 4 where it is predicted to alter the integrity of this scaffold and at the surface of blade 3, respectively.

The kelch propeller domain of Keap1 is involved in protein-protein interactions like most kelch containing modules[43]. Keap1 is a negative regulator of the inducible Nrf2-dependent cytoprotective response, sequestering Nrf2 in the cytoplasm under steady state. Upon oxidative stress, the Nrf2/Keap1 complex is disrupted, Nrf2 translocates to the nucleus, where it induces transcription of cytoprotective ARE-dependent genes[49,50]. We speculate that similar functions may be devoted to PF3D7_1343700 in P. falciparum, such that mutations of the K13-propeller impair its interactions with an unknown protein partner, resulting in a deregulated anti-oxidant/cytoprotective response. The P. falciparum anti-oxidant response is maximal during the late trophozoite stage, when hemoglobin digestion and metabolism are highest[51]. Its regulation is still poorly understood and no Nrf2 ortholog could be identified in the *Plasmodium* genome.

Figure 9A:
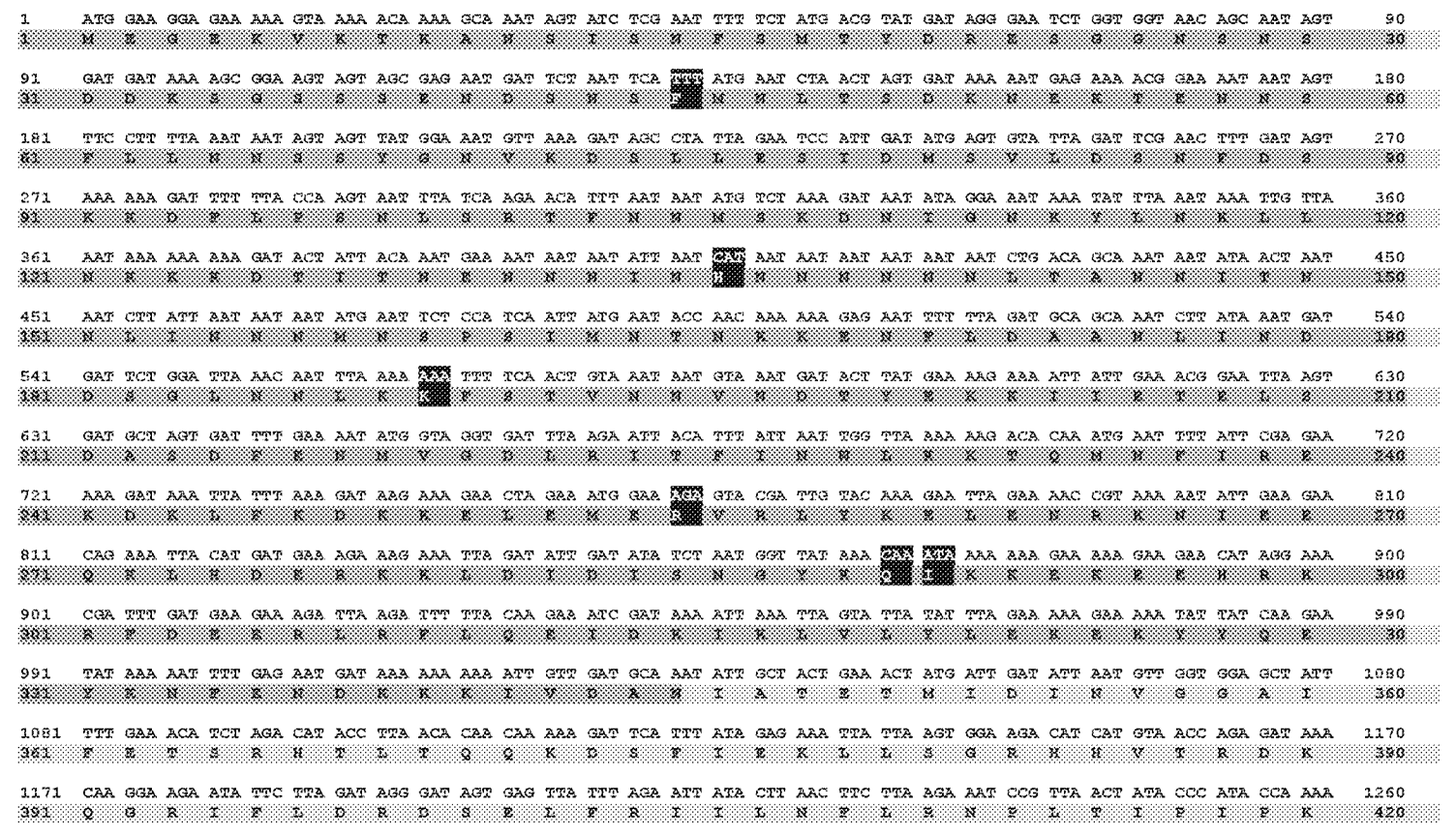
Figure 9B:
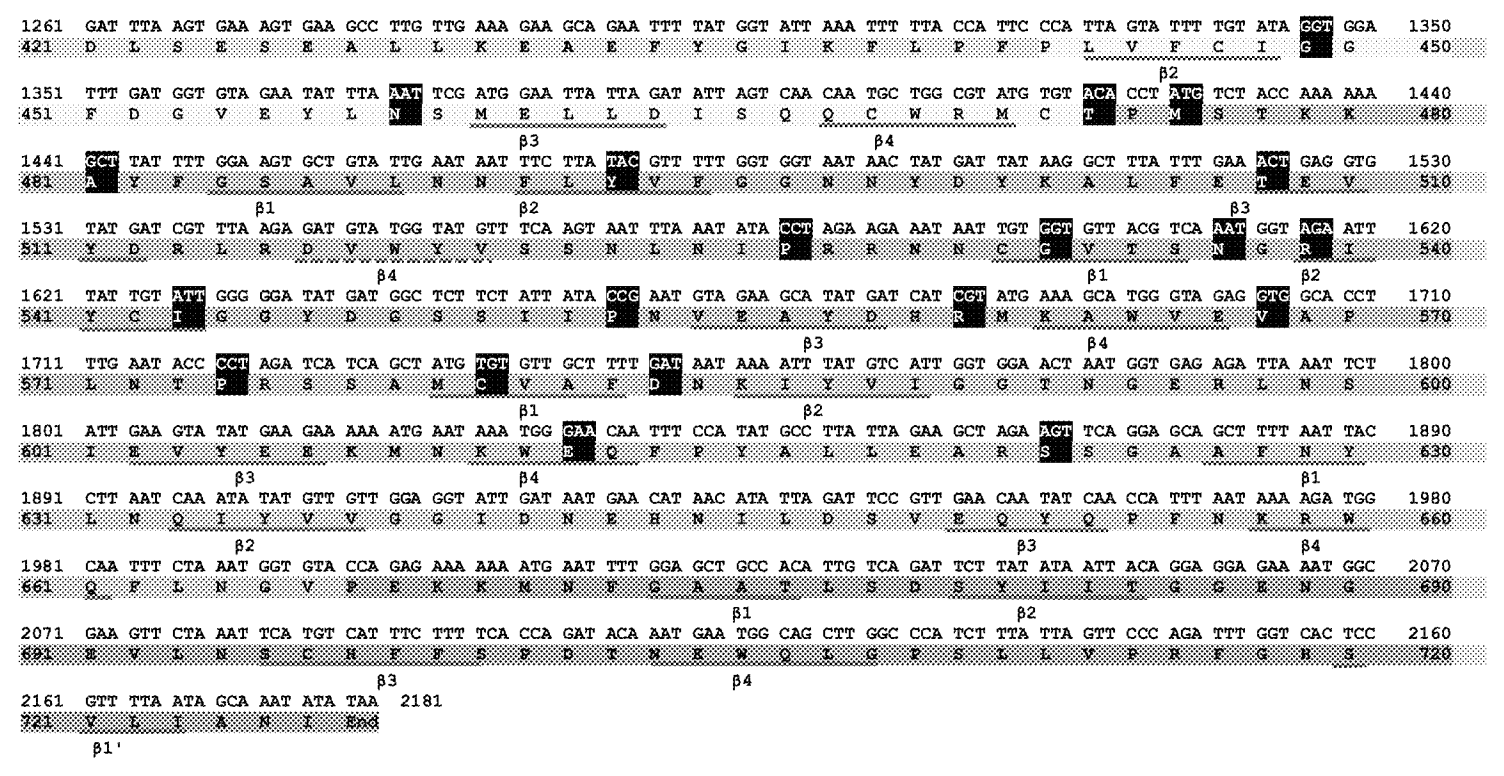

FIGS. 9A and 9B—PF3D7_1343700 reference nucleic acid (SEQ ID NO:1) and amino acid (SEQ ID NO:2) coding sequences (3D7-type) and mutant positions.

FIG. 9A color code: dark grey, *Plasmodium*-specific (1-225) and Apicomplexa-specific (225-345) positions; light grey, BTB/POZ domain. In FIG. 9B the positions of the polymorphic codons reported in PlasmoDB version 9.3 (http://www.plasmodb.org/plasmo/) and those observed in the present study are boxed in black. Note that most reported polymorphisms are located in the N-terminal domain apart from E621 D observed in one isolate from The Gambia (ref. 44). Six individual kelch domains are localized from residue 443 to 473, 474 to 526, 527 to 573, 574 to 614, 615 to 666, and 667 to 726, respectively.

FIGS. 10A to 10C—ClustalW-Alignment of the protein sequence of PF3D7_1343700 orthologs from seven *Plasmodium* species.

Codes:
F-XP_001350158 *P. falciparum* (PF3D7_1343700) (SEQ ID NO:2)
V-XP_001614215 *P. vivax* Sal1 (SEQ ID NO:3)
C-XP_004223579 *P. cynomolgi* (SEQ ID NO:4)
K-XP_002259918 *P. knowlesi* (SEQ ID NO:5)
B-XP_674094 *P. berghei* (SEQ ID NO:6)
Y-XP_730901 *P. yoelii* (SEQ ID NO:7)
PCHAS_136130 *P. chabaudi* (SEQ ID NO:8)
Polymorphic *P. falciparum* residues are shaded in grey.

Figure 11:
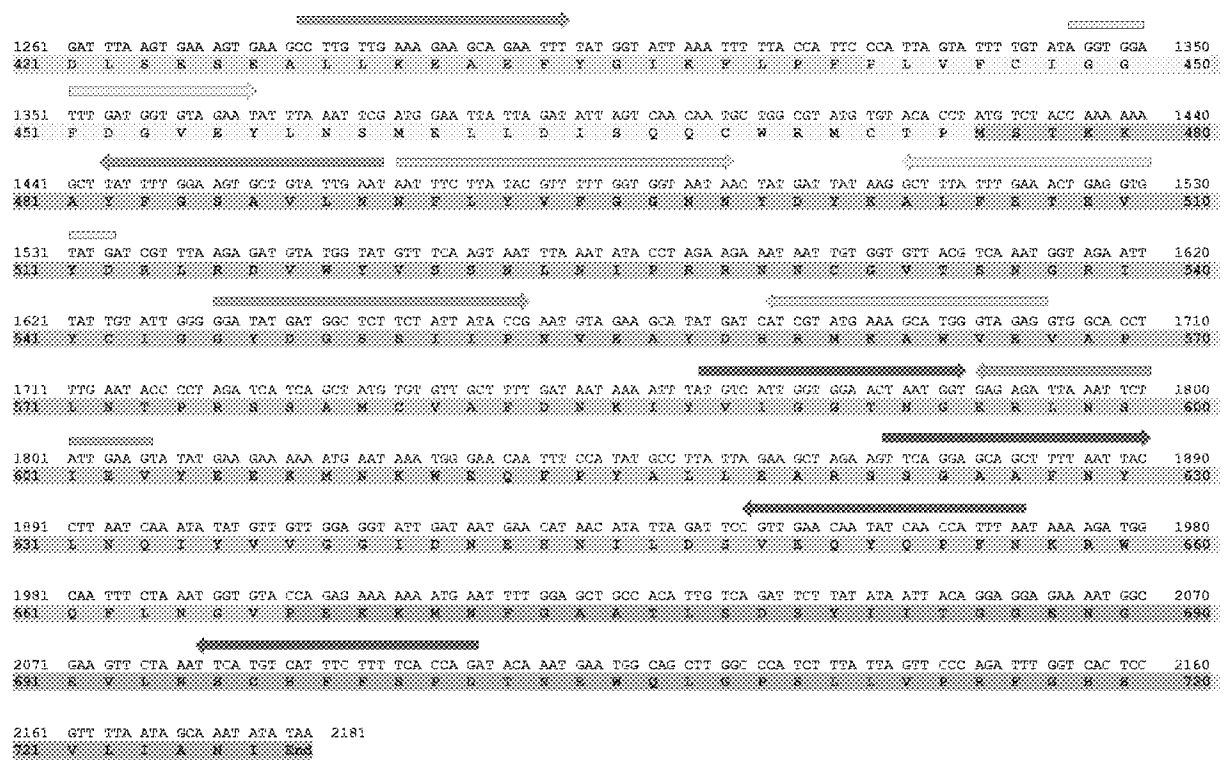

FIG. 11—Real time PCR-HRM: detection of mutated K13 propeller alleles versus wild type K13 propeller allele. Nucleic acid sequence is nt 1261-2181 of SEQ ID NO:1. Amino acid sequence is aa 421-726 of SEQ ID NO:2.

Six pairs of primers designed on the sequence of the propeller domain of K13 gene to amplify all the domain and are designated by arrows.

FIGS. 12A and 12B—A) Detection of mutated K13 propeller alleles versus wild type K13 propeller allele by real time PCR-HRM (nt 1279-2127 of SEQ ID NO:1).

B) Sequence of the six primer pairs, their localization on the nucleic acid sequence of the K13 propeller domain and size of amplification products. (SEQ ID NOs:27-38).

Figure 13:
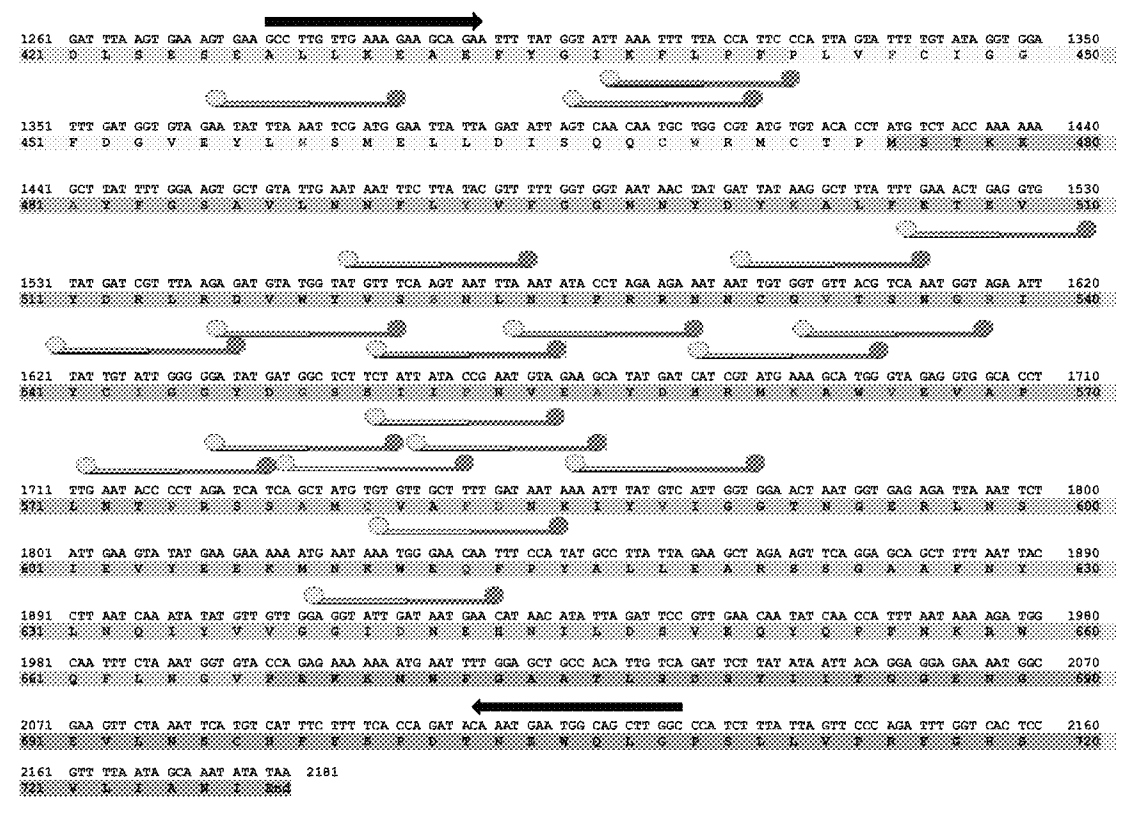

FIG. 13—Detection of 20 of the mutated K13 propeller alleles by PCR reaction and probe hybridization by a Luminex® multiplex assay (Multiplex Ligase Detection Reaction-fluorescent microsphere assay). Nucleic acid sequence is nt 1261-2181 of SEQ ID NO:1. Amino acid sequence is aa 421-726 of SEQ ID NO:2.

Black arrows show primers for PCR reaction,
Primer F 5' gccttgttgaaagaagcaga 3' (SEQ ID NO:14)
Primer R 5'-gccaagctgccattcatttg-3' (SEQ ID NO:13)

Specific probes (light grey and dark grey) are designed in order to detect Single Nucleotide Polymorphisms (SNP) in the K13 propeller domain. Light grey probes are allele-specific and are bound to fluorescent beads. For each light grey position, there are two probes, one with the mutated nucleotide at 3' extremity and one with the wild-type nucleotide at 3' extremity. Dark grey probes are designed in conserved sequence regions and are bound to biotin.

List of SNPs:
F446I ttt/att
G449A ggt/gct
N458Y aat/tat
C469Y tgc/tac
W470stop tgg/tga
A481V gct/gtt
Y493H tac/cac
K503N aag/aat
S522C agt/tgt
V534A gtt/gct
R539T aga/aca
I543T att/act
G548D ggc/gac
P553L ccg/ctg
V555A gta/gca
A557S gca/tca
R561H cgt/cat
K563R aaa/aga
V568G gtg/ggg
P574L cct/ctt
A578S gct/tct
C580Y tgt/tat
F583L ttt/tta/g
D584V gat/gtt
V589I gtc/atc
Q613E caa/gaa
D641G gat/ggt

| Non synonymous SNP | wild type codon versus mutant codon | nucleotide at 3' extremity of allele-specific probe |
|---|---|---|
| F446I | ttt/att | 1336 |
| G449A | ggt/gct | 1346 |
| N458Y | aat/tat | 1372 |
| C469Y | tgc/tac | 1406 |
| W470stop | tgg/tga | 1410 |
| A481V | gct/gtt | 1442 |
| Y493H | tac/cac | 1477 |
| K503N | aag/aat | 1509 |
| S522C | agt/tgt | 1564 |
| V534A | gtt/gct | 1601 |
| R539T | aga/aca | 1616 |
| I543T | att/act | 1628 |
| G548D | ggc/gac | 1643 |
| P553L | ccg/ctg | 1658 |
| V555A | gta/gca | 1664 |
| A557S | gca/tca | 1669 |
| R561H | cgt/cat | 1682 |
| K563R | aaa/aga | 1688 |
| V568G | gtg/ggg | 1703 |
| P574L | cct/ctt | 1721 |
| A578S | gct/tct | 1732 |
| C580Y | tgt/tat | 1739 |
| F583L | ttt/tta/g | 1749 |
| D584V | gat/gtt | 1751 |
| V589I | gtc/atc | 1765 |
| Q613E | caa/gaa | 1837 |
| D641G | gat/ggt | 1922 |

FIG. 14 presents Table 1—Sequence of the primers used to amplify the genes containing non-synonymous single-nucleotide polymorphisms in F32-ART5. Forward primers (SEQ ID NOs 39-45) and reverse primers (SEQ ID NOs 46-52) are shown.

FIG. 15 presents Table 2—Description of the eight non-synonymous, single-nucleotide polymorphisms acquired in the F32-ART5 compared to the F32-TEM lineage during an effective 5-year discontinuous exposure to increasing concentrations of artemisinin.

3D7-type sequence; the same codon sequence is also observed in the parental F32-Tanzania line.

*Artemisinin (ART) dose used for selection during the corresponding drug-pressure cycle.

[a] Genes found in the chromosomal location of top-ranked signatures of selection in Takala-Harrison et al.[16].

FIGS. 16A to 16B present Table 3—Reported characteristics of the genes mutated in F32-ART5 parasites.

FIG. 17 presents Table 4—Geographic origin and year of collection of archived blood samples studied for K13-propeller polymorphism.

FIG. 18 presents Table 5—Polymorphisms observed in the K13-propeller in Cambodian *P. falciparum* isolates collected in 2001-2012 and in The Gambia (ref. 42).

\* observed in F32-ART5, not observed in Cambodia

\*\* reported in The Gambia (ref. 42), not observed in Cambodia

FIG. 19 presents Table 6—Association between polymorphisms observed in the K13-propeller and KH subpopulations (ref. 15) observed in 150 *P. falciparum* isolates collected in 2009-2010 in Pursat (n=103) and Ratanakiri (n=47) provinces, Cambodia.

FIG. 20 presents Table 7—List of the most frequent mutations identified in K13 propeller domain in Asia and Africa.

Figure 22B:
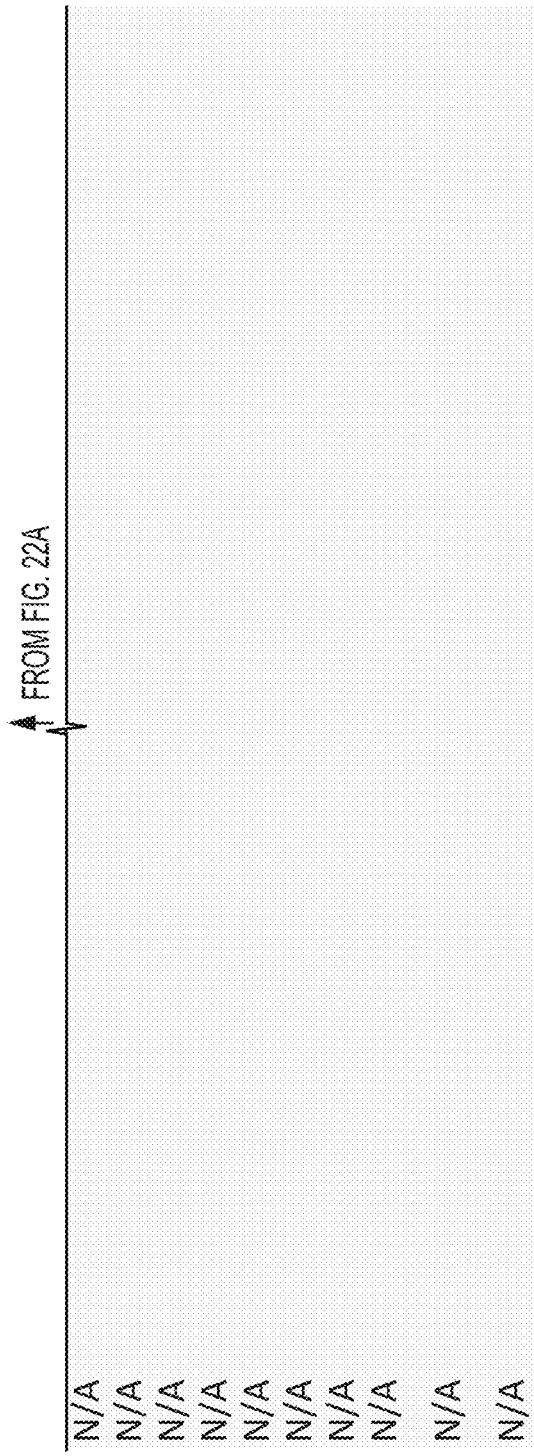

FIGS. 21A and 21B present Table 8A, FIGS. 22A and 22B present Table 8B, and FIGS. 23A and 23B present Table 8C. FIGS. 21A, 21B, 22A, 22B, 23A, and 23B together show Fifty clinical *P. falciparum* isolates from Cambodia (collected in 2010 and 2011) that were adapted to in vitro culture as described by Witkowski et al.[45] RSA and polymorphisms are indicated.

DETAILED DESCRIPTION OF THE INVENTION

*Plasmodium falciparum* resistance to artemisinin derivatives in Southeast Asia threatens malaria control and elimination activities worldwide. To monitor the spread of artemisinin-resistance, a molecular marker is urgently needed. Here, using whole-genome sequencing of an artemisinin-resistant parasite line from Africa and clinical parasite isolates from Cambodia, we associate mutations in the PF3D7_1343700 kelch propeller domain ('K13-propeller') with artemisinin resistance in vitro and in vivo. Mutant K13-propeller alleles cluster in Cambodian provinces where resistance is prevalent, and the increasing frequency of a dominant mutant K13-propeller allele correlates with the recent spread of resistance in Western Cambodia. Strong correlations between the presence of a mutant allele, in vitro parasite survival rates, and in vivo parasite clearance rates indicate that K13-propeller mutations are important determinants of artemisinin resistance. K13-propeller polymorphism constitutes a useful molecular marker for large-scale surveillance efforts to contain artemisinin resistance in the Greater Mekong Subregion and prevent its global spread.

Identification of a Candidate Molecular Marker for ART Resistance

The ART-resistant F32-ART5 parasite line was selected by culturing the ART-sensitive F32-Tanzania clone under a dose-escalating, 125-cycle regimen of artemisinin for 5 years[18]. Whole-genome sequences were obtained for both F32-ART5 and F32-TEM (its sibling clone cultured without artemisinin) at 460× and 500× average nucleotide coverage, respectively. Compared to F32-TEM, no deleted genes were identified in F32-ART5. The exomes of F32-ART5 and F32-TEM were compared after excluding (i) genes from highly-variable, multi-gene families (var, rifin and stevor), (ii) positions with coverage lower than 25% of the mean coverage of the parasite line, (iii) single-nucleotide polymorphisms (SNPs) found to be mixed in F32-ART5, given that acquired ART-resistance mutation(s) could be expected to be fixed in the sample after 5 years of continuous pressure, (iv) SNPs shared between F32-ART5 and the ART-sensitive 3D7 parasite strain and (v) synonymous SNPs (FIG. 5).

Figure 1:
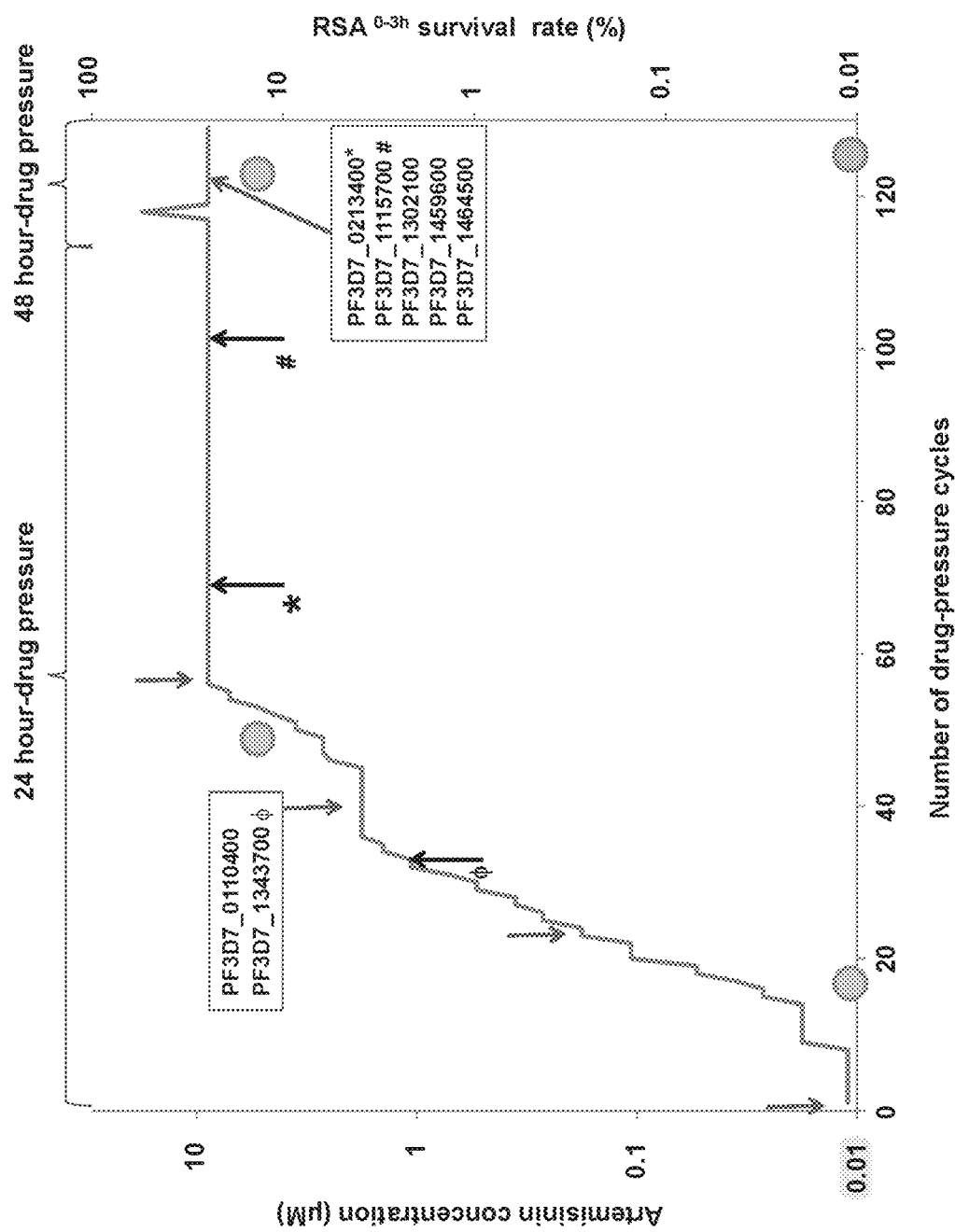
FIG. 1—Temporal acquisition of mutations in F32-ART5. F32-Tanzania parasites exposed to increasing artemisinin concentrations for 120 consecutive cycles[18] were analysed by whole-genome sequencing at five time-points (grey arrows). Loci mutated after a given number of drug-pressure cycles are shown (boxes). The earliest time-points where three mutations were detected by PCR (black arrows) are indicated by ø for PF3D7_1343700, * for PF3D7_0213400 and # for PF3D7_1115700. Circles indicate RSA$^{0-3h}$ survival rates for F32-ART5 and F32-TEM parasites, respectively.

This analysis identified eight mutations in seven genes that were subsequently confirmed by Sanger sequencing of PCR products (Table 1). Each gene harbors one mutant codon in F32-ART5 compared to F32-TEM, F32-Tanzania or 3D7 (Table 2). Information on the expression of the genes and the biological function of the proteins are listed in Table 3. Only one of these genes, cysteine protease falcipain 2a (PF3D7_1115700), has previously been associated with in vitro responses to ART[19]. To determine when each mutation arose in the F32-ART5 lineage, we analyzed the whole-genome sequences of parasites at various drug-pressure cycles (FIG. 1). This analysis showed that the PF3D7_0110400 D56V and PF3D7_1343700 M476I mutations were acquired first, during the steep increase of ART resistance, and remained stable thereafter. Importantly, the appearance of these two mutations is associated with an increase in the ring-stage survival assay ($RSA^{0-3h}$) survival rate, from less than 0.01% to 12.8%. Subsequent PCR analysis of the PF3D7_1343700 locus detected the M476I mutation after 30 drug-pressure cycles, consistent with the sharp increase in $RSA^{0-3h}$ survival rate observed thereafter. The other SNPs appeared stepwise at a later stage of selection: PF3D7_0213400 (68 cycles); PF3D7_1115700 (98 cycles); PF3D7_1302100, PF3D7_1459600 and PF3D7_1464500 (120 cycles) (Table 2). These data suggest that the PF3D7_1343700 M476I mutation increased the resistance of F32-Tanzania to DHA in the $RSA^{0-3h}$.

To explore whether these mutations are associated with ART resistance in Cambodia, we investigated sequence polymorphism in all seven genes by mining whole-genome or Sanger sequences for 49 culture-adapted parasite isolates collected in 2010-2011 (see Examples). We chose these isolates based on their differential $RSA^{0-3h}$ survival rates (Table 8) and their sequences were compared to those of control parasites lines 3D7, 89F5[20] and K1992 (see Examples). Three genes (PF3D7_0110400, PF3D7_0213400 and PF3D7_1302100) encode a wildtype sequence for all parasite isolates. The other four genes show intra-population diversity, with previously reported or novel SNPs (Table 8). PF3D7_1115700 has 11 SNPs that are not associated with $RSA^{0-3h}$ survival rates (P=0.06, Kruskal-Wallis test). PF3D7_1459600 has 6 SNPs that are not associated with survival rates (P=0.65). PF3D7_1464500 has 12 SNPs previously reported in older isolates from Southeast Asia, including the ART-susceptible Dd2 line[21], probably reflecting a geographic signature. These SNPs also show no significant association with survival rates (P=0.42). Therefore, these six genes were not studied further.

In contrast, PF3D7_1343700 polymorphism shows a significant association with $RSA^{0-3h}$ survival rates (FIG. 2). Indeed, $RSA^{0-3h}$ survival rates differ substantially between parasite isolates with wildtype (median 0.17%, range 0.06-0.51%, n=16) or mutant (18.8%, 3.8-58%, n=33) K13-propeller alleles (P<$10^{-4}$, Mann-Whitney U test) (Table 8). Four mutant alleles are observed, each harboring a single non-synonymous SNP within a kelch repeat of the C-terminal K13-propeller domain, namely Y493H, R539T, I543T and C580Y located within repeats #2, #3, #3 and #4, respectively. Both the K1992 and the ART-susceptible 89F5 lines carry a wildtype K13-propeller. There are no associations between polymorphisms in the K-13 propeller and those in the other candidate genes (Table 8). Based on these observations and the acquisition of M476I in kelch repeat #2 by F32-ART5, we investigated whether K13-propeller polymorphism is a molecular signature of ART resistance in Cambodia.

Emergence and Spread of Mutant K13-Propeller Alleles in Cambodia

Over the last decade, the prevalence of ART resistance has steadily increased in the western provinces of Cambodia, but not elsewhere in the country[2]. To test whether the spatiotemporal distribution of K13-propeller mutations correlates with that of ART resistance, we sequenced the K13-propeller of archived parasite isolates from Cambodian patients with malaria in 2001-2012 (Table 4). Data from six provinces were compared (n=886): Pailin, Battambang and Pursat in the west where ART-resistance is established[1, 6, 5, 22], Kratie in the southeast where ART-resistance has increased in recent years[2], and Preah Vihear in the north and Ratanakiri in the northeast where there was virtually no evidence of ART resistance during this time period[2]. This analysis reveals overall 17 mutant alleles, including three high-frequency (≥5%) alleles (C580Y, R539T and Y493H). The frequency of wildtype sequence decreased significantly over time in all three western provinces, but not in Preah Vihear or Ratanakiri. The frequency of the C580Y allele increased significantly from 2001-2002 to 2011-2012 in Pailin and Battambang, indicating its rapid invasion of the population and near fixation in these areas (FIG. 3).

To further investigate the geographic diversity of K13-propeller polymorphism in Cambodia, we extended our sequence analysis to include data from four additional provinces (n=55, Kampong Som, Kampot, Mondulkiri and Oddar Meanchey) in 2011-2012 (Table 4). Although a large number of mutations are observed (FIG. 9 and Table 5), the C580Y allele accounts for 85% (189/222) of all mutant alleles observed in 2011-2012 (FIG. 6). This mapping outlines the elevated frequency (74%, 222/300) of parasites harboring a single non-synonymous mutation in the K13-propeller and the geographic disparity of their distribution. Importantly, the frequency distribution of mutant alleles over the various provinces matches that of day 3 positivity in patients treated for malaria with an ACT (Spearman's r=0.99, 95% CI 0.96-0.99, P<0.0001)—considered a suggestive sign of clinical ART resistance (FIG. 7).

Relationships Between K13-Propeller Polymorphisms, ART-Resistant Subpopulations and Clinical ART Resistance To confirm that K13-propeller polymorphism is a molecular marker of clinical ART resistance, we first identified 163 patients from Pursat and Ratanakiri in whom we measured parasite clearance half-lives (range 1.58-11.53 h)[6] in 2009-2010 and for which parasites were previously assigned to a KH subpopulation (KH1, KH2, KH3, KH4 or KHA) based on ancestry analysis of whole-genome sequence data[15]. Thirteen patients with mixed genotypes (a wild-type and one or more mutant K13-propeller alleles) were excluded. Of the remaining 150 patients, 72 carried parasites with a wild-type allele and the others carried parasites with only a single non-synonymous SNP in the K13-propeller: C580Y (n=51), R539T (n=6) and Y493H (n=21) (Table 6). The parasite clearance half-life in patients with wildtype parasites is significantly shorter (median 3.30 h, IQR 2.59-3.95) than those with C580Y (7.19 h, 6.47-8.31, $P<10^{-6}$, Mann-Whitney U test), R539T (6.64 h, 6.00-6.72, $P<10^{-4}$) or Y493H (6.28 h, 5.37-7.14, $P<10^{-6}$) parasites (FIG. 4A). Also, the parasite clearance half-life in patients carrying C580Y parasites is significantly longer than those with Y493H parasites (P=0.007, Mann-Whitney U test). These data indicate that C580Y, R539T and Y493H identify slow-clearing parasites in malaria patients treated with ART.

Since KH2, KH3, KH4 and KHA parasites have longer half-lives than KH1 parasites[15], we hypothesized that allelic variation in the K13-propeller accounts for these differences. Among 150 parasites, 55, 26, 14, 12 and 43 are classified as KH1, KH2, KH3, KH4 and KHA, respectively. Three K13-propeller alleles strongly associate with KH groups: 96% (53/55) of KH1, 96% (25/26) of KH2 and 100% (12/12) of KH4 parasites carry the wildtype, C580Y and Y493H alleles, respectively (Table 6). While KH3 parasites (n=14) carry the wildtype, C580Y and R539T alleles, R539T is not observed in KH1, KH2 or KH4 parasites. As expected, KHA parasites have a mixed allele composition. Importantly, K13-propeller mutations more accurately identify slow-clearing parasites than KH group (FIG. 4B), demonstrating that the association of K13-propeller polymorphism with clinical ART resistance in Cambodia is partially independent of the genetic background of KH subpopulations. Within the KH1 group (n=55), the parasite clearance half-life in patients with wildtype parasites is significantly shorter (n=53, median 2.88 h, IQR 2.52-3.79) than those with Y493H parasites (n=2, median 6.77 h, P=0.02, Mann-Whitney U test). Within the KH3 subpopulation (n=14), the half-life in patients with wildtype parasites is shorter (n=3, median 3.65 h) than those with C580Y (n=7, median 8.73 h, IQR 7.35-9.06, P=0.02) or R539T (n=4, 6.65 h, 6.29-6.80, P=0.03) parasites.

The F32-ART5 lineage acquired a K13-propeller mutation as it developed ART-resistance, as indicated by its ability to survive a pharmacologically-relevant exposure to DHA in the RSA$^{0-3h}$. Genes putatively associated with ART resistance (Pfcrt[23, 24] PftCtp[25, 26], Pfmdr1[8, 27, 28], Pfmrp1[27-29] and ABC transporters[30]) or encoding putative targets of ART (PfATPase6[31, 32] and Pfubcth—the ortholog of P. chabaudi ubp1[33, 34]) were not mutated during the 5-year selection of F32-ART5, and Pfmdr1 amplification was not observed[35-40]. In addition, all candidate ART-resistance genes recently identified using population genetics approaches[14, 40, 41] remained unaltered in the F32-ART5 lineage, except for PF3D7_1343700 and PF3D7_1459600 located in the linkage-disequilibrium windows identified by Takala-Harrison et al.[16]. These findings led us to identify another 17 single K13-propeller mutations in naturally-circulating parasites in Cambodia. Several of these mutations associate strongly with the spatiotemporal distribution of ART resistance in Cambodia, increased parasite survival rates in response to DHA in vitro, and long parasite clearance half-lives in response to ART treatment in vivo. None of the six other genes mutated in F32-ART5 associate with RSA$^{0-3h}$ survival rates in parasite isolates from Cambodia.

K13-propeller polymorphism fulfills the definition of a molecular marker of ART resistance for several reasons: (i) there has been a progressive loss of wildtype parasites in Western Cambodia during the decade of emerging ART resistance in this region; (ii) mutant parasites cluster in Cambodian provinces where ART resistance is well established and are less prevalent where ART resistance is uncommon; (iii) PF3D7_1343700 is located 5.9 kb upstream of the 35-kb locus identified by Cheeseman et al.[14] as being under recent positive selection, and within the region of top-ranked signatures of selection outlined by Takala-Harrison et al.[16]; (iv) multiple mutations, all non-synonymous, are present in the K13-propeller, reflecting positive selection rather than a hitchhiking effect or genetic drift; (v) mutations occur in a domain that is highly conserved in P. falciparum, with only one non-synonymous SNP being documented in a single parasite isolate from Africa[42]; (vi) all polymorphisms we observe in Cambodia are novel and all but one (V568G)

occur at positions strictly conserved between *Plasmodium* species (FIG. 9 and FIG. 10), suggesting strong structural and functional constraints on the protein; (vii) the three most-prevalent K13-propeller mutations correlate strongly with RSA$^{0-3h}$ survival rates in vitro and parasite clearance half-lives in vivo at the level of individual parasite isolates and malaria patients, respectively, and (viii) the frequency of mutant alleles correlates strongly with the prevalence of day 3 positivity after ACT treatment at the level of human populations in Cambodia.

Based on homology with other kelch propeller domains, we anticipate that the observed K13-propeller mutations destabilize the domain scaffold and alter its function. The C-terminal portion of PF3D7_1343700 encodes six kelch motifs, which are found in a large number of proteins with diverse cellular functions[43, 44]. Given that the toxicity of ART derivatives principally depends on their pro-oxidant activity, the reported role of some kelch-containing proteins in regulating cytoprotective and protein degradation responses to external stress is particularly intriguing. The K13-propeller shows homology with human KLHL12 and KLHL2 involved in ubiquitin-based protein degradation and KEAP1 involved in cell adaptation to oxidative stress (FIG. 8). Obviously, future work is needed to delineate the normal function of K13 and the impact of various mutations. Allele exchange studies in mutant and wildtype parasites may help to define the contribution of K13-propeller polymorphisms on different genetic backgrounds to the RSA$^{0-3h}$ survival rate. Indeed, it is particularly worrying that as few as two mutations, i.e. the K13-propeller M476I and PF3D7_0110400 D56V, were sufficient to confer ART resistance to F32-Tanzania, which has a typical African genetic background. Since Cambodian parasites with mutant K13-propellers display a wide range of RSA$^{0-3h}$ survival rates (3.8%-58%) and parasite clearance half-lives (4.5-11.5 h), further studies are required to identify additional genetic determinants of ART resistance, which may reside in the strongly-selected regions recently identified[16, 14]. In this context, analyzing the RSA$^{0-3h}$ survival rates as a quantitative trait among parasites harboring the same K13-propeller mutation could help to identify additional genetic loci involved in ART resistance.

In summary, K13-propeller polymorphism is a useful molecular marker for tracking the emergence and spread of ART-resistant *P. falciparum*.

Methods of Genotyping a *Plasmodium*

The invention encompasses methods for genotyping a *plasmodium*, particularly *Plasmodium falciparum*. The method, performed in vitro, comprises the step of detecting the presence or absence of a wild-type or mutated K-13 propeller nucleic acid or protein, in a biological sample. Said sample has been previously obtained from a patient and is in particular a blood sample. In a preferred embodiment, the method comprises providing a biological sample containing a *plasmodium* and detecting the presence or absence of a wild-type or mutated K-13 propeller nucleic acid or protein in the sample. The wild-type or mutated K-13 propeller nucleic acid or protein is detected by routine techniques in the art. For example, the techniques described in the Examples, or elsewhere herein, can be used.

The biological sample is advantageously a blood sample.

The wild-type or mutated K-13 propeller nucleic acid can be detected by numerous techniques known in the art, such as sequencing, hybridization, or amplification assays.

Within the context of this invention, a "wild-type *P. falciparum* K-13 propeller nucleic acid" means a nucleic acid having the sequence of SEQ ID NO:1 or a variant nucleic acid sequence that encodes the amino acid sequence of SEQ ID NO:2. Within the context of this invention, a "wild-type *P. falciparum* K-13 propeller protein" means a protein having the amino acid sequence of SEQ ID NO:2. Other wild-type *plasmodium* K-13 propeller proteins are shown in FIG. 10.

Within the context of this invention, a "mutant *P. falciparum* K-13 propeller nucleic acid" is synonymous with a "mutated *P. falciparum* K-13 propeller nucleic acid" and means a nucleic acid sequence having one or more difference from the nucleic acid sequence of SEQ ID NO:1 that results in a difference of at least one amino acid from the amino acid sequence of SEQ ID NO:2. Preferably a mutant *P. falciparum* K13-propeller nucleic acid according to the invention harbors a single non-synonymous Single Nucleotide Polymorphism (SNP) within a kelch repeat of the carboxy-terminal K13-propeller domain. More preferably the single non-synonymous SNP is one of the following SNPs:

F446I ttt/att
G449A ggt/gct
N458Y aat/tat
C469Y tgc/tac
W470stop tgg/tga
A481V gct/gtt
Y493H tac/cac
K503N aag/aat
S522C agt/tgt
V534A gtt/gct
R539T aga/aca
I543T att/act
G548D ggc/gac
P553L ccg/ctg
V555A gta/gca
A557S gca/tca
R561H cgt/cat
K563R aaa/aga
V568G gtg/ggg
P574L cct/ctt
A578S gct/tct
C580Y tgt/tat
F583L ttt/tta/g
D584V gat/gtt
V589I gtc/atc
Q613E caa/gaaD641G gat/ggt Within the context of this invention, a "mutant *P. falciparum* K-13 propeller protein" is synonymous with a "mutated *P. falciparum* K-13 propeller protein" and means an amino acid sequence having one or more difference from the amino acid sequence of SEQ ID NO:2. The one or more difference from the amino acid sequence of SEQ ID NO:2 is one or more mutant amino acid within a kelch repeat of the carboxy-terminal K13-propeller domain of the *P. falciparum* K-13 propeller protein.

Preferred mutant *P. falciparum* K-13 propeller proteins have one or more of the mutations shown in FIG. 9 or 13.

More preferred mutant *P. falciparum* K-13 propeller proteins have a single mutation chosen among the mutations shown in FIG. 9 or 13.

These mutations are also defined in accordance with the list of SNPs provided above.

In various embodiments, the method comprises detecting the presence or absence of a wild-type or mutated K-13 propeller protein in the biological sample. This can be performed by using specific antibodies that discriminate between wild-type and mutant K-13 propeller proteins. These antibodies can be contacted with patient samples and the presence or absence of a wild-type or mutated K-13 propeller proteins can be determined by detecting the presence or absence of an immunological reaction. Preferably, the method comprises an ELISA assay.

In a preferred embodiment, the method comprises providing a sample containing a *plasmodium* and detecting the presence of a mutated K-13 propeller nucleic acid or protein in the sample. Preferably, the presence of a mutated K-13 propeller nucleic acid in the sample is detected by sequencing or by PCR.

Preferably, the *plasmodium* is selected from *Plasmodium falciparum*, *Plasmodium vivax*, *Plasmodium ovale curtisi*, *Plasmodium ovale wallikeri*, *Plasmodium malariae*, *Plasmodium knowlesi*, *Plasmodium brasilianum*, *Plasmodium cynomolgi*, *Plasmodium cynomolgi bastianellii*, *Plasmodium inui*, *Plasmodium rhodiani*, *Plasmodium schweitzi*, *Plasmodium semiovale*, *Plasmodium simium*, *Plasmodium berghei*, *Plasmodium yoelii*, and *Plasmodium chabaudi*.

The invention encompasses methods for genotyping a *Plasmodium*. Preferably, the method discriminates between artemisinin-susceptible *Plasmodium* (with a wild-type K13 allele) from artemisinin-resistant *Plasmodium* (with a mutant K13 allele).

The invention encompasses in vitro methods for detecting at least one mutation in the K13 propeller domain nucleic acid sequence. The invention encompasses methods for detecting in a biological sample containing *Plasmodium* the presence of a mutant K13 propeller nucleic acid comprising contacting K13 propeller nucleic acid with a probe specific for a mutant K13 propeller and detecting the binding of the probe to the K13 propeller nucleic acid. Binding of the probe with the K13 propeller nucleic acid can be detected by routine techniques in the art. For example, any of the techniques described herein can be used. Exemplary mutants and probes are depicted in Example 15 and FIG. 13. Preferably, probes are at least 15, 20, 25, or 30 bp in size. Most preferably, they are 15-20, 15-25, 15-30, 20-25, or 25-30 nt in size.

In some embodiments, the probe is bound to a fluorescent bead. In some embodiments, the method comprises binding the probe to the mutant K13 propeller domain nucleic acid and detecting the bound K13 propeller domain nucleic acid with a probe that binds to the bound K13 propeller domain nucleic acid. In some embodiments, the K13 propeller nucleic acid is amplified prior to detection.

In one embodiment, the nucleic acids of a *plasmodium* are subjected to an amplification of the K13 propeller domain nucleic acid sequence. In various embodiments, 1, 2, 3, 4, 5, 6, 7, 8, 9, 10, or more fragments of the K13 propeller domain nucleic acid sequence are amplified. The amplified fragments can be from at least 50, 75, 100, 125, 150, 175, or 200 nt in size to at least 75, 100, 125, 150, 175, 200, 250, or 300 nt in size. Primers for this amplification can be any of the primers set forth herein.

Preferably, the amplification method is PCR, most preferably real-time PCR, PCR-HRM (High-Resolution DNA Melting) (see Andriantsoanirina et al. Journal of Microbiological Methods, 78: 165 (2009)), or PCR coupled to ligase detection reaction based on fluorescent microsphere (Luminex® microspheres). This last method permits to perform a multiplex assay to detect several mutated K13 propeller alleles at the same time.

Other preferred amplification methods include the ligase chain reaction (LCR) (e.g., Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), and nucleic acid based sequence amplification (NABSA) (U.S. Pat. Nos. 5,130,238, 5,409,818, 5,554,517, and 6,063,603). Other amplification methods that may be used are described in U.S. Pat. Nos. 5,242,794, 5,494,810, 4,988,617 and 6,582,938. The above references regarding amplification of nucleic acids are specifically incorporated by reference with respect to the disclosure therein of the specific reaction conditions used for amplification in each of the amplification methods.

In one embodiment, the method comprises providing *Plasmodium* nucleic acid, PCR amplifying at least one fragment of the K13 propeller domain nucleic acid sequence in the *Plasmodium* nucleic acid, and detecting at least one mutation in the K13 propeller domain nucleic acid sequence. The invention encompasses methods for detecting in a biological sample containing *Plasmodium* the presence of a mutant K13 propeller nucleic acid comprising amplifying the mutant K13 propeller nucleic acid by PCR reaction, and contacting the amplified nucleic acid with a probe specific for a mutant K13 propeller. Exemplary mutants and probes are depicted in Example 15 and FIG. 13. Preferably, probes are at least 15, 20, 25, or 30 bp in size.

In one embodiment, the mutation is detected by High-Resolution DNA Melting. In various embodiments, 1, 2, 3, 4, 5, 6, 7, 8, 9, 10, or more fragments of the K13 propeller domain nucleic acid sequence are amplified and assessed by High-Resolution DNA Melting for the presence of mutations. Most preferably, 6 fragments of the K13 propeller domain nucleic acid sequence are amplified and assessed by High-Resolution DNA Melting for the presence of mutations.

In one embodiment, the method comprises providing a biological sample containing DNA of *Plasmodium*; optionally extracting DNA from the biological sample; contacting the DNA of *Plasmodium* with at least one pair of primers which hybridize specifically with the K13 propeller nucleic acid, preferably at a distance ranging from 100 to 300 bp, and performing a PCR reaction, preferably in the presence of intercalating dye. Preferably, the amplification products are subjected to a melting step and a melting profile of the amplification products is generated. The melting step can allow the determination of the presence of a mutant allele or a wild type allele by analyzing the melting profile of the amplification products.

In one embodiment, the mutation is detected by specific probes that are designed in order to detect Single Nucleotide Polymorphisms (SNP) in the K13 propeller domain. In one embodiment, allele-specific probes are bound to a solid substrate, preferably beads, most preferably fluorescent beads. The probes can be specific for a mutation in the K13 propeller domain or for the wild-type K13 propeller domain. The probes can bind to (i.e., capture) the mutant or wild-type K13 propeller domain nucleic acid. The bound (i.e., captured) K13 propeller domain nucleic acid can then be detected with a probe that binds to the bound (i.e., captured) K13 propeller domain nucleic acid. Preferably, the assay is based on fluorescent microspheres (Luminex® microspheres). Exemplary mutants and probes are depicted in Example 15 and FIG. 13. Preferably, probes are at least 15, 20, 25, or 30 bp in size. Preferably, the probe spans one of the mutations listed in Example 15 and FIG. 13.

In various embodiments, at least one fragment of the K13 propeller domain nucleic acid sequence is amplified using at least a primer having a nucleotide sequence selected from SEQ ID NOs 15-26. Preferably, one or more primer sets used for amplification are selected from the following primer pairs:

Pair PCR1:
5' AGGTGGATTTGATGGTGTAGAAT 3' (forward) (SEQ ID NO:15)
5' CATACACCTCAGTTTCAAATAAAGC 3' (reverse) (SEQ ID NO:16)

Pair PCR2:
5' AATTTCTTATACGTTTTTGGTGGTAA 3' (forward) (SEQ ID NO:17)
5' CTCTACCCATGCTTTCATACGAT 3' (reverse) (SEQ ID NO:18)

Pair PCR3
5' GGATATGATGGCTCTTCTATTATACCG 3' (forward) (SEQ ID NO:19)
5' ACTTCAATAGAATTTAATCTCTCACCA 3' (reverse) (SEQ ID NO:20)

Pair PCR4
5' ATGTCATTGGTGGAACTAATGGT 3' (forward) (SEQ ID NO:21)
5' TTAAATGGTTGATATTGTTCAACG 3' (reverse) (SEQ ID NO:22)

Pair PCR5
5' TTCAGGAGCAGCTTTTAATTACC 3' (forward) (SEQ ID NO:23)
5' CTGGTGAAAAGAAATGACATGAA 3' (reverse) (SEQ ID NO:24)

Pair PCR6
5' CCTTGTTGAAAGAAGCAGAATTT 3' (forward) (SEQ ID NO:25)
5' ATTCAATACAGCACTTCCAAAATAA 3' (reverse) (SEQ ID NO:26).

In various embodiments, 1, 2, 3, 4, 5, 6, 7, 8, 9, 10, or more fragments of the K13 propeller domain nucleic acid sequence are amplified and assessed for the presence of mutations. Most preferably, 6 fragments of the K13 propeller domain nucleic acid sequence are amplified and assessed by High-Resolution DNA Melting for the presence of mutations. Preferably, the mutation detected is selected from the following mutations (from/to):

F446I ttt/att
G449A ggt/gct
N458Y aat/tat
C469Y tgc/tac
W470stop tgg/tga
A481V gct/gtt
Y493H tac/cac
K503N aag/aat
S522C agt/tgt
V534A gtt/gct
R539T aga/aca
I543T att/act
G548D ggc/gac
P553L ccg/ctg
V555A gta/gca
A557S gca/tca
R561H cgt/cat
K563R aaa/aga
V568G gtg/ggg
P574L cct/ctt
A578S gct/tct
C580Y tgt/tat
F583L ttt/tta/g
D584V gat/gtt
V589I gtc/atc
Q613E caa/gaa
D641G gat/ggt.

Most preferably, the mutation detected is 1, 2, 3, 4, 5, 6, 7, 8, 9, 10, 11, 12, 13, 14, or all of the following mutations:
F446I ttt/att
G449A ggt/gct
N458Y aat/tat
A481V gct/gtt
Y493H tac/cac
K503N aag/aat
R539T aga/aca
I543T att/act
P553L ccg/ctg
A557S gca/tca
R561H cgt/cat
V568G gtg/ggg
P574L cct/ctt
A578S gct/tct
C580Y tgt/tat Methods of Monitoring ART-Resistance The invention encompasses methods for monitoring ART-resistance of a *Plasmodium*. In a preferred embodiment, the method comprises growing a *Plasmodium*, contacting the *Plasmodium* with an artemisinin, and detecting a mutation in a K-13 propeller nucleic acid or protein. Preferably, the *Plasmodium* is grown in vitro, preferably as in van Schalkwyk et al. Malaria Journal 2013, 12:320, which is hereby incorporated by reference.

In one embodiment, the method comprises growing a *Plasmodium*, contacting the *Plasmodium* with an artemisinin, and sequencing a K-13 propeller nucleic acid or protein at multiple time points.

In one embodiment, the method comprising providing multiple samples of *Plasmodium*, from a single or multiple geographic areas, and detecting a mutation in a K-13 propeller nucleic acid or protein.

Methods of Detecting a *Plasmodium* Infection

The invention encompasses methods for the detection of a *Plasmodium* infection and diagnosis of the infection in an infected patient. Patients can be diagnosed by providing a cell sample from a patient. In a preferred embodiment, the method comprises providing a cell sample from a patient and detecting the presence or absence of a wild-type or mutated K-13 propeller nucleic acid or protein in the cell sample.

The wild-type or mutated K-13 propeller nucleic acid or protein is detected by routine techniques in the art. For example, the any of the techniques described herein can be used.

The cell sample can be any cell sample obtained from patient that contains *Plasmodium*. Preferably, the cell sample is generated by drawing blood. The cell sample is preferably a blood sample. The blood sample can be further processed to culture the *Plasmodium* in the sample in vitro. For example, the techniques described in van Schalkwyk et al. Malaria Journal 2013, 12:320 can be used.

In one embodiment, the method comprises providing a blood sample from patient; optionally culture the *Plasmodium* in the sample in vitro, and detecting the presence or absence of a wild-type or mutated K-13 propeller nucleic acid or protein in the cell sample.

In one embodiment, the method comprises providing a blood sample from a patient and detecting the presence or absence of a wild-type or mutated K-13 propeller nucleic acid or protein in the sample. Preferably, the presence of a mutated K-13 propeller nucleic acid in the sample is detected by sequencing or by PCR.

Preferably, nucleic acid sequencing is used to detect the presence or absence of a wild-type or mutated K-13 propeller nucleic acid in the cell sample. Any sequencing method known in the art can be employed. As used herein, the term "sequencing" is used in a broad sense and refers to any technique known by the skilled person including but not limited to Sanger dideoxy termination sequencing, whole-genome sequencing, sequencing by hybridization, pyrosequencing, capillary electrophoresis, cycle sequencing, single-base extension sequencing, solid-phase sequencing, high-throughput sequencing, massively parallel signature sequencing (MPSS), sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD® sequencing, MS-PET sequencing, mass spectrometry, and a combination thereof. In specific embodiments, the method of the invention is adapted to run on ABI PRISM® 377 DNA Sequencer, an ABI PRISM® 310, 3100, 3100-Avant, 3730, or 3730x1 Genetic Analyzer, an ABI PRISM® 3700 DNA Analyzer, or an Applied Biosystems SOLiD™ System (all from Applied Biosystems), a Genome Sequencer 20 System (Roche Applied Science).

Preferably, the K-13 propeller in the *Plasmodium* of the cell sample has one or more of the mutations shown in FIG. 9 or 13 or in Table 7.

In one embodiment, the method comprises detecting any of the nucleic acid sequences encoding any of the mutations shown in FIG. 9 or 13 or in Table 7. These sequences can be specifically detected by numerous techniques known in the art, such as sequencing, hybridization, or amplification assays.

For example, the amplification method can be RCA, MDA, NASBA, TMA, SDA, LCR, b-DNA, PCR (all forms including RT-PCR), RAM, LAMP, ICAN, SPIA, QB-replicase, or Invader. A preferred amplification method is the polymerase chain reaction (PCR) amplification. See, e.g., PCR Technology: Principles and Applications for DNA Amplification (Ed. H. A. Erlich, Freeman Press, NY, N.Y., 1992); PCR Protocols: A Guide to Methods and Applications (Eds. Iinis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159 4,965,188, and 5,333,675. More preferred PCR methods is real-time PCR, PCR-HRM (High-Resolution DNA Melting) (see Andriantsoanirina et al. Journal of Microbiological Methods, 78: 165 (2009)) and PCR coupled to ligase detection reaction based on fluorescent microsphere (Luminex® microspheres). This last method permits to perform a multiplex assay to detect several mutated K13 propeller alleles in a same time.

Other preferred amplification methods include the ligase chain reaction (LCR) (e.g., Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), and nucleic acid based sequence amplification (NABSA) (U.S. Pat. Nos. 5,130,238, 5,409,818, 5,554,517, and 6,063,603). Other amplification methods that may be used are described in U.S. Pat. Nos. 5,242,794, 5,494,810, 4,988,617 and 6,582,938. The above references regarding amplification of nucleic acids are specifically incorporated by reference with respect to the disclosure therein of the specific reaction conditions used for amplification in each of the amplification methods.

In a preferred embodiment, at least one of the following primers is used for amplification:

forward K13-1 5'-cggagtgaccaaatctggga-3' (SEQ ID NO:9);

reverse K13-4 5'-gggaatctggtggtaacagc-3' (SEQ ID NO:10);

forward K13-2 5'-cgccagcattgttgactaat-3' (SEQ ID NO:11);

reverse K13-3 5'-gcggaagtagtagcgagaat-3' (SEQ ID NO:12);

forward 5'-gccaagctgccattcatttg-3' (SEQ ID NO:13); and reverse 5'-gccttgttgaaagaagcaga-3' (SEQ ID NO:14).

The nucleic acid can be RNA or DNA. In one embodiment, RNA is extracted and reverse-transcribed into cDNA. Amplification or sequencing is then performed on the cDNA.

Thus, the method can comprise isolating RNA from a sample from a patient, reverse-transcribing the RNA into cDNA, amplifying or sequencing the cDNA, and determining the presence or absence of a wild-type or mutated K-13 propeller nucleic acid.

In various embodiments, the method comprises detecting the presence or absence of a wild-type or mutated K-13 propeller protein in the cell sample. This can be performed by using specific antibodies that discriminate between wild-type and mutant K-13 propeller proteins. These antibodies can be contacted with patient samples and the presence or absence of a wild-type or mutated K-13 propeller proteins can be determined by detecting the presence or absence of an immunological reaction. Preferably, the method comprises an ELISA assay.

Antibodies can be synthetic, monoclonal, or polyclonal and can be made by techniques well known in the art. Such antibodies specifically bind via the antigen-binding sites of the antibody (as opposed to non-specific binding). K-13 propeller polypeptides, fragments, variants, fusion proteins, etc., can be employed as immunogens in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, Immuno Biology 3:9 (Garland Publishing Inc., 2nd ed. 1996)). Because folded proteins have complex surfaces, the number of epitopes available is quite numerous; however, due to the conformation of the protein and steric hinderances, the number of antibodies that actually bind to the epitopes is less than the number of available epitopes (C. A. Janeway, Jr. and P. Travers, Immuno Biology 2:14 (Garland Publishing Inc., 2nd ed. 1996)). Epitopes can be identified by any of the methods known in the art. Both polyclonal and monoclonal antibodies can be prepared by conventional techniques.

K-13 propeller peptides based on the amino acid sequence of wild-type and mutant K-13 propeller proteins can be utilized to prepare antibodies that specifically bind to wild-type and/or mutant K-13 propeller. The term "antibodies" is meant to include polyclonal antibodies, monoclonal antibodies, fragments thereof, such as F(ab')2 and Fab fragments, single-chain variable fragments (scFvs), single-domain antibody fragments (VHHs or Nanobodies), bivalent antibody fragments (diabodies), as well as any recombinantly and synthetically produced binding partners.

Antibodies are defined to be specifically binding if they bind to wild-type and/or mutant K-13 propeller polypeptide with a Ka of greater than or equal to about 107 M−1. Affinities of binding partners or antibodies can be readily determined using conventional techniques, for example those described by Scatchard et al., Ann. N.Y. Acad. Sci., 51:660 (1949).

Polyclonal antibodies can be readily generated from a variety of sources, for example, horses, cows, goats, sheep, dogs, chickens, rabbits, mice, or rats, using procedures that are well known in the art. In general, purified K-13 propeller or a peptide based on the amino acid sequence of K-13 propeller that is appropriately conjugated is administered to the host animal typically through parenteral injection. The immunogenicity of K-13 propeller can be enhanced through the use of an adjuvant, for example, Freund's complete or incomplete adjuvant. Following booster immunizations, small samples of serum are collected and tested for reactivity to K-13 propeller polypeptide. Examples of various assays useful for such determination include those described in Antibodies: A Laboratory Manual, Harlow and Lane (eds.), Cold Spring Harbor Laboratory Press, 1988; as well as procedures, such as countercurrent immuno-electrophoresis (CIEP), radioimmunoassay, radio-immunoprecipitation, enzyme-linked immunosorbent assays (ELISA), dot blot assays, and sandwich assays. See U.S. Pat. Nos. 4,376,110 and 4,486,530.

Monoclonal antibodies can be readily prepared using well known procedures. See, for example, the procedures described in U.S. Pat. Nos. RE 32,011, 4,902,614, 4,543,439, and 4,411,993; Monoclonal Antibodies, Hybridomas: A New Dimension in Biological Analyses, Plenum Press, Kennett, McKeam, and Bechtol (eds.), 1980.

For example, the host animals, such as mice, can be injected intraperitoneally at least once and preferably at least twice at about 3 week intervals with isolated and purified wild-type or mutant K-13 propeller protein or conjugated K-13 propeller peptide, optionally in the presence of adjuvant. Mouse sera are then assayed by conventional dot blot technique or antibody capture (ABC) to determine which animal is best to fuse. Approximately two to three weeks later, the mice are given an intravenous boost of protein or peptide. Mice are later sacrificed and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG). Fusion is plated out into plates containing media that allows for the selective growth of the fused cells. The fused cells can then be allowed to grow for approximately eight days. Supernatants from resultant hybridomas are collected and added to a plate that is first coated with goat anti-mouse Ig. Following washes, a label, such as a labeled K-13 propeller polypeptide, is added to each well followed by incubation. Positive wells can be subsequently detected. Positive clones can be grown in bulk culture and supernatants are subsequently purified over a Protein A column (Pharmacia).

The monoclonal antibodies of the invention can be produced using alternative techniques, such as those described by Alting-Mees et al., "Monoclonal Antibody Expression Libraries: A Rapid Alternative to Hybridomas", Strategies in Molecular Biology 3:1-9 (1990), which is incorporated herein by reference. Similarly, binding partners can be constructed using recombinant DNA techniques to incorporate the variable regions of a gene that encodes a specific binding antibody. Such a technique is described in Larrick et al., Biotechnology, 7:394 (1989).

Antigen-binding fragments of such antibodies, which can be produced by conventional techniques, are also encompassed by the present invention. Examples of such fragments include, but are not limited to, Fab and F(ab')2 fragments.

Antibody fragments and derivatives produced by genetic engineering techniques are also provided.

The monoclonal antibodies of the present invention include chimeric antibodies, e.g., humanized versions of murine monoclonal antibodies. Such humanized antibodies can be prepared by known techniques, and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment can comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (Nature 332:323, 1988), Liu et al. (PNAS 84:3439, 1987), Larrick et al. (Bio/Technology 7:934, 1989), and Winter and Harris (TIPS 14:139, May, 1993). Procedures to generate antibodies transgenically can be found in GB 2,272,440, U.S. Pat. Nos. 5,569,825 and 5,545,806.

Antibodies produced by genetic engineering methods, such as chimeric and humanized monoclonal antibodies, comprising both human and non-human portions, which can be made using standard recombinant DNA techniques, can be used. Such chimeric and humanized monoclonal antibodies can be produced by genetic engineering using standard DNA techniques known in the art, for example using methods described in Robinson et al. International Publication No. WO 87/02671; Akira, et al. European Patent Application 0184187; Taniguchi, M., European Patent Application 0171496; Morrison et al. European Patent Application 0173494; Neuberger et al. PCT International Publication No. WO 86/01533; Cabilly et al. U.S. Pat. No. 4,816,567; Cabilly et al. European Patent Application 0125023; Better et al., Science 240:1041 1043, 1988; Liu et al., PNAS 84:3439 3443, 1987; Liu et al., J. Immunol. 139:3521 3526, 1987; Sun et al. PNAS 84:214 218, 1987; Nishimura et al., Canc. Res. 47:999 1005, 1987; Wood et al., Nature 314:446 449, 1985; and Shaw et al., J. Natl. Cancer Inst. 80:1553 1559, 1988); Morrison, S. L., Science 229:1202 1207, 1985; Oi et al., BioTechniques 4:214, 1986; Winter U.S. Pat. No. 5,225,539; Jones et al., Nature 321:552 525, 1986; Verhoeyan et al., Science 239:1534, 1988; and Beidler et al., J. Immunol. 141:4053 4060, 1988.

In connection with synthetic and semi-synthetic antibodies, such terms are intended to cover but are not limited to antibody fragments, isotype switched antibodies, humanized antibodies (e.g., mouse-human, human-mouse), hybrids, antibodies having plural specificities, and fully synthetic antibody-like molecules.

For therapeutic applications, "human" monoclonal antibodies having human constant and variable regions are often preferred so as to minimize the immune response of a patient against the antibody. Such antibodies can be generated by immunizing transgenic animals which contain human immunoglobulin genes. See Jakobovits et al. Ann NY Acad Sci 764:525-535 (1995).

Human monoclonal antibodies against K-13 propeller polypeptides can also be prepared by constructing a combinatorial immunoglobulin library, such as a Fab phage display library or a scFv phage display library, using immunoglobulin light chain and heavy chain cDNAs prepared from mRNA derived from lymphocytes of a subject. See, e.g., McCafferty et al. PCT publication WO 92/01047; Marks et al. (1991) J. Mol. Biol. 222:581 597; and Griffths et al. (1993) EMBO J 12:725 734. In addition, a combinatorial library of antibody variable regions can be generated by mutating a known human antibody. For example, a variable region of a human antibody known to bind K-13 propeller, can be mutated, by for example using randomly altered mutagenized oligonucleotides, to generate a library of mutated variable regions which can then be screened to bind to K-13 propeller. Methods of inducing random mutagenesis within the CDR regions of immunoglobin heavy and/or light chains, methods of crossing randomized heavy and light chains to form pairings and screening methods can be found in, for example, Barbas et al. PCT publication WO 96/07754; Barbas et al. (1992) Proc. Nat'l Acad. Sci. USA 89:4457 4461.

An immunoglobulin library can be expressed by a population of display packages, preferably derived from filamentous phage, to form an antibody display library. Examples of methods and reagents particularly amenable for use in generating antibody display library can be found in, for example, Ladner et al. U.S. Pat. No. 5,223,409; Kang et al. PCT publication WO 92/18619; Dower et al. PCT publication WO 91/17271; Winter et al. PCT publication WO 92/20791; Markland et al. PCT publication WO 92/15679; Breitling et al. PCT publication WO 93/01288; McCafferty et al. PCT publication WO 92/01047; Garrard et al. PCT publication WO 92/09690; Ladner et al. PCT publication WO 90/02809; Fuchs et al. (1991) Bio/Technology 9:1370 1372; Hay et al. (1992) Hum Antibod Hybridomas 3:81 85; Huse et al. (1989) Science 246:1275 1281; Griffths et al. (1993) supra; Hawkins et al. (1992) J Mol Biol 226:889 896; Clackson et al. (1991) Nature 352:624 628; Gram et al. (1992) PNAS 89:3576 3580; Garrad et al. (1991) Bio/Technology 9:1373 1377; Hoogenboom et al. (1991) Nuc Acid Res 19:4133 4137; and Barbas et al. (1991) PNAS 88:7978 7982. Once displayed on the surface of a display package (e.g., filamentous phage), the antibody library is screened to identify and isolate packages that express an antibody that binds a K-13 propeller polypeptide. In a preferred embodiment, the primary screening of the library involves panning with an immobilized K-13 propeller polypeptide and display packages expressing antibodies that bind immobilized K-13 propeller polypeptide are selected.

In a preferred embodiment, the method comprises detecting a *plasmodium* infection. The method can further comprise determining whether the *plasmodium* has a wild-type or mutant K-13 propeller nucleic acid or protein sequence.

Methods of Treating a *Plasmodium* Infection

The invention encompasses methods for treating a *plasmodium* infection, In one embodiment, the method comprises determining whether a patient is infected by a *plasmodium* containing a wild-type or mutant K-13 propeller nucleic acid or protein sequence and adjusting the anti-parasitic treatment based on whether patient is infected by a *plasmodium* containing a wild-type or mutant K-13 propeller.

In a preferred embodiment, if the patient is infected by a *plasmodium* containing a wild-type K-13 propeller, the patient is treated with an artemisinin derivative.

In a preferred embodiment, if the patient is infected by a *plasmodium* containing a mutant K-13 propeller, the patient is treated with an anti-parasitic treatment without an artemisinin, preferably with a malarial drug selected among quinine, chloroquine and mefloquine.

In another embodiment, if the patient is infected by a *plasmodium* containing a mutant K-13 propeller, the patient is treated with an artemisinin derivative for a period longer than the routinely-used period.

The invention also concerns artemisinin derivative for use in the treatment of patients infected with *Plasmodium* having a wild-type K-13 propeller, wherein an in vitro step of detecting whether *Plasmodium* contains a wild-type K-13 propeller is performed on a biological sample previously obtained from said patient The invention further relates to artemisinin derivative for use in the treatment of patients infected with *Plasmodium* having a mutated K-13 propeller, wherein an in vitro step of detecting whether *Plasmodium* contains a mutated K-13 propeller is performed on a biological sample previously obtained from said patient and wherein the administration regime and/or the administered doses of artemisinin is(are) extended over time and/or doses are higher with respect to regime, respectively doses applied to infection by *Plasmodium* that contains a wild-type K-13 propeller.

The invention in addition concerns quinine, chloroquinine or mefloquine for use in the treatment of patients infected with *Plasmodium* having a mutated K-13 propeller, wherein an in vitro step of detecting whether *Plasmodium* contains a mutated K-13 propeller is performed on a biological sample previously obtained from said patient.

Accordingly, using said drugs in accordance with the infection's profile first encompasses the step of detecting and genotyping the *Plasmodium* infection as provided in the present invention in accordance with the various embodiments to determine whether *Plasmodium* carries a wild-type K-13 propeller or rather a mutated K-13 propeller.

Kits for Genotyping a *Plasmodium*

The invention encompasses kits for genotyping a *plasmodium* or for detecting a *plasmodium* infection. Preferably, the kit contains primers for the amplification of a K-13 propeller nucleic acid. The kit can contain reagents for the detection of the amplified product. The kit can contain any primer or any combination of primers set forth herein. The kit can contain at least 1, 2, 3, 4, 5, 6, 7, 8, 9, 10, 11, 12, or more of the primers set forth herein. In one embodiment, the kit comprises at least one pair of primers which hybridize specifically with the K13 propeller nucleic acid at a distance ranging from 100 to 300 bp. In a preferred embodiment of the kit, the at least one pair of primers which hybridize specifically with the K13 propeller nucleic acid at a distance ranging from 100 to 300 bp surrounds at least one single-nucleotide polymorphism (SNP).

Preferably, the kit contains a probe for detecting a K-13 propeller nucleic acid, particularly an amplified K-13 propeller nucleic acid. Preferably, the probe is labeled with a fluorescent or enzymatic label.

In one embodiment, the kit specifically detects a mutant K-13 propeller nucleic acid, particularly one encoding a Y493H, R539T, I543T, or C580Y allele. In one embodiment, the kit specifically detects a wild-type K-13 propeller nucleic acid.

In a preferred embodiment, the kit comprises at least one of the following primers:
5'-cggagtgaccaaatctggga-3' (SEQ ID NO:9);
5'-gggaatctggtggtaacagc-3' (SEQ ID NO:10);
5'-cgccagcattgttgactaat-3' (SEQ ID NO:11); and
5'-gcggaagtagtagcgagaat-3' (SEQ ID NO:12).
5'-gccaagctgccattcatttg-3' (SEQ ID NO:13); and
5'-gccttgttgaaagaagcaga-3' (SEQ ID NO:14).

In some embodiments, the kit detects a mutant K13 propeller nucleic acid encoding a F446I, N458Y, C469Y, Y493H, K503N, R539T, I543T, P553L, P574L, A578S, C580Y, and D584V allele.

In some embodiments, the kit detects a mutant K13 propeller nucleic acid encoding a F446I, G449A, N458Y, C469Y, W470stop, A481V, Y493H, K503N, S522C, V534A, R539T, I543T, G548D, P553L, V555A, A557S, R561H, K563R, V568G, P574L, A578S, C580Y, F583L, D584V, V589I, Q613E, and D641G allele.

In some embodiments, the kit comprises at least one of the following pairs of primers:
Pair PCR1
5' AGGTGGATTTGATGGTGTAGAAT 3' (forward) (SEQ ID NO:15)
5' CATACACCTCAGTTTCAAATAAAGC 3' (reverse) (SEQ ID NO:16)
Pair PCR2:
5' AATTTCTTATACGTTTTTGGTGGTAA 3' (forward) (SEQ ID NO:17)
5' CTCTACCCATGCTTTCATACGAT 3' (reverse) (SEQ ID NO:18)
Pair PCR3
5' GGATATGATGGCTCTTCTATTATACCG 3' (forward) (SEQ ID NO:19)
5' ACTTCAATAGAATTTAATCTCTCACCA 3' (reverse) (SEQ ID NO:20)
Pair PCR4
5' ATGTCATTGGTGGAACTAATGGT 3' (forward) (SEQ ID NO:21)
5' TTAAATGGTTGATATTGTTCAACG 3' (reverse) (SEQ ID NO:22)
Pair PCR5
5' TTCAGGAGCAGCTTTTAATTACC 3' (forward) (SEQ ID NO:23)
5' CTGGTGAAAAGAAATGACATGAA 3' (reverse) (SEQ ID NO:24)
Pair PCR6
5' CCTTGTTGAAAGAAGCAGAATTT 3' (forward) (SEQ ID NO:25)
5' ATTCAATACAGCACTTCCAAAATAA 3' (reverse) (SEQ ID NO:26) In some embodiments, the kit comprises at least one probe hybridizing with one of the following SNP:
F446I ttt/att
G449A ggt/gct
N458Y aat/tat
C469Y tgc/tac
W470stop tgg/tga
A481V gct/gtt
Y493H tac/cac
K503N aag/aat
S522C agt/tgt
V534A gtt/gct
R539T aga/aca
I543T att/act
G548D ggc/gac
P553L ccg/ctg
V555A gta/gca
A557S gca/tca
R561H cgt/cat
K563R aaa/aga
V568G gtg/ggg
P574L cct/ctt
A578S gct/tct
C580Y tgt/tat
F583L ttt/tta/g
D584V gat/gtt
V589I gtc/atc
Q613E caa/gaa
D641G gat/ggt.

Methods of Screening New Malarial Drugs

The invention encompasses methods for screening new malarial drugs effective for the treatment of patients infected by an ART-resistant *Plasmodium*. In one embodiment, the method comprises the following steps:
genotyping a *Plasmodium* in a biological sample from a patient infected by *Plasmodium* according to the invention;
measuring the parasite clearance half-life and/or survival rates of the *Plasmodium*, if the *Plasmodium* infecting the patient has a mutant K13-propeller allele;
contacting the new drug to be tested with the biological sample, if the *Plasmodium* infecting the patient has a mutant K13-propeller allele;
- measuring the parasite clearance half-life and/or survival rate of the *Plasmodium* in the $RSA_{0-3h}$ after administration of the drug;

selecting the drug as a malarial drug effective for the treatment of patients infected by an ART-resistant *Plasmodium*, if the parasite clearance half-life and/or the survival rates of the *Plasmodium* is diminished after administration of the drug.

In another embodiment, the method further comprises administrating the drug to be tested to the patient, if the *Plasmodium* infecting the patient has a mutant K13-propeller allele.

REFERENCES

1. Dondorp, A. M. et al. Artemisinin resistance in *Plasmodium falciparum* malaria. N Engl J Med 361, 455-67 (2009).
2. World Health Organization. in WHO publications (ed. Press, W.) (2011-2013).
3. Mita, T. et al. Limited geographical origin and global spread of sulfadoxine-resistant dhps alleles in *Plasmodium falciparum* populations. J Infect Dis 204, 1980-8 (2011).
4. Roper, C. et al. Intercontinental spread of pyrimethamine-resistant malaria. Science 305, 1124 (2004).
5. Wootton, J. C. et al. Genetic diversity and chloroquine selective sweeps in *Plasmodium falciparum*. Nature 418, 320-3 (2002).
6. Amaratunga, C. et al. Artemisinin-resistant *Plasmodium falciparum* in Pursat province, western Cambodia: a parasite clearance rate study. Lancet Infect Dis 12, 851-8 (2012).
7. Kyaw, M. P. et al. Reduced susceptibility of *Plasmodium falciparum* to artesunate in southern Myanmar. PLoS One 8, e57689 (2013).

8. Noedl, H. et al. Evidence of artemisinin-resistant malaria in western Cambodia. N Engl J Med 359, 2619-20 (2008).
9. Phyo, A. P. et al. Emergence of artemisinin-resistant malaria on the western border of Thailand: a longitudinal study. Lancet 379, 1960-6 (2012).
10. Tran, T. H. et al. In vivo susceptibility of *Plasmodium falciparum* to artesunate in Binh Phuoc Province, Vietnam. Malar J 11, 355 (2012).
11. Flegg, J. A., et al. Standardizing the measurement of parasite clearance in *falciparum* malaria: the parasite clearance estimator. Malar J 10, 339 (2011).
12. White, N. J. The parasite clearance curve. Malar J 10, 278 (2011).
13. Witkowski, B. et al. Novel phenotypic assays for the detection of artemisinin-resistant *Plasmodium falciparum* malaria in Cambodia: in-vitro and ex-vivo drug-response studies. Lancet Infect Dis 13 (2013).
14. Cheeseman, I. H. et al. A major genome region underlying artemisinin resistance in malaria. Science 336, 79-82 (2012).
15. Miotto, O. et al. Multiple populations of artemisinin-resistant *Plasmodium falciparum* in Cambodia. Nat Genet 45, 648-55 (2013).
16. Takala-Harrison, S. et al. Genetic loci associated with delayed clearance of *Plasmodium falciparum* following artemisinin treatment in Southeast Asia. Proc Natl Acad Sci USA 110, 240-5 (2012).
17. Lopera-Mesa, T. M. et al. *Plasmodium falciparum* clearance rates in response to artesunate in Malian children with malaria: effect of acquired immunity. J Infect Dis 207, 1655-63 (2013).
18. Witkowski, B. et al. Increased tolerance to artemisinin in *Plasmodium falciparum* is mediated by a quiescence mechanism. Antimicrob Agents Chemother 54, 1872-7 (2010).
19. Klonis, N. et al. Artemisinin activity against *Plasmodium falciparum* requires hemoglobin uptake and digestion. Proc Natl Acad Sci USA 108, 11405-10 (2011).
20. Vigan-Womas, I. et al An in vivo and in vitro model of *Plasmodium falciparum* rosetting and autoagglutination mediated by varO, a group A var gene encoding a frequent serotype. Infect Immun. December; 76(12):5565-80 (2008)
21. Cui, L. et al. Mechanisms of in vitro resistance to dihydroartemisinin in *Plasmodium falciparum*. Mol Microbiol 86, 111-28 (2012).
22. Leang, R. et al. Efficacy of dihydroartemisinin-piperaquine for treatment of uncomplicated *Plasmodium falciparum* and *Plasmodium vivax* in Cambodia, 2008 to 2010. Antimicrob Agents Chemother 57, 818-26 (2012).
23. Sidhu, A. B. et al. Chloroquine resistance in *Plasmodium falciparum* malaria parasites conferred by pfcrt mutations. Science 298, 210-3 (2002).
24. Valderramos, S. G. et al. Identification of a mutant PfCRT-mediated chloroquine tolerance phenotype in *Plasmodium falciparum*. PLoS Pathog 6, e1000887 (2010).
25. Bhisutthibhan, J. et al. The *Plasmodium falciparum* translationally controlled tumor protein homolog and its reaction with the antimalarial drug artemisinin. J Biol Chem 273, 16192-8 (1998).
26. Eichhorn, T. et al. Molecular interaction of artemisinin with translationally controlled tumor protein (TCTP) of *Plasmodium falciparum*. Biochem Pharmacol 85, 38-45 (2013).
27. Sanchez, C. P. et al. Polymorphisms within PfMDR1 alter the substrate specificity for anti-malarial drugs in *Plasmodium falciparum*. Mol Microbiol 70, 786-98 (2008).
28. Veiga, M. I. et al. Novel polymorphisms in *Plasmodium falciparum* ABC transporter genes are associated with major ACT antimalarial drug resistance. PLoS One 6, e20212 (2011).
29. Raj, D. K. et al. Disruption of a *Plasmodium falciparum* multidrug resistance-associated protein (PfMRP) alters its fitness and transport of antimalarial drugs and glutathione. J Biol Chem 284, 7687-96 (2009).
30. Anderson, T. J. et al. Are transporter genes other than the chloroquine resistance locus (pfcrt) and multidrug resistance gene (pfmdr) associated with antimalarial drug resistance? Antimicrob Agents Chemother 49, 2180-8 (2005).
31. Jambou, R. et al. Resistance of *Plasmodium falciparum* field isolates to in-vitro artemether and point mutations of the SERCA-type PfATPase6. Lancet 366, 1960-3 (2005).
32. Krishna, S. et al. Artemisinins and the biological basis for the PfATP6/SERCA hypothesis. Trends Parasitol 26, 517-23 (2010).
33. Hunt, P. et al. Gene encoding a deubiquitinating enzyme is mutated in artesunate- and chloroquine-resistant rodent malaria parasites. Mol Microbiol 65, 27-40 (2007).
34. Hunt, P. et al. Experimental evolution, genetic analysis and genome re-sequencing reveal the mutation conferring artemisinin resistance in an isogenic lineage of malaria parasites. BMC Genomics 11, 499 (2010).
35. Borges, S. et al. Genome-wide scan reveals amplification of mdr1 as a common denominator of resistance to mefloquine, lumefantrine, and artemisinin in *Plasmodium chabaudi* malaria parasites. Antimicrob Agents Chemother 55, 4858-65 (2011).
36. Chavchich, M. et al. Role of pfmdr1 amplification and expression in induction of resistance to artemisinin derivatives in *Plasmodium falciparum*. Antimicrob Agents Chemother 54, 2455-64 (2010).
37. Chen, N. et al. Deamplification of pfmdr1-containing amplicon on chromosome 5 in *Plasmodium falciparum* is associated with reduced resistance to artelinic acid in vitro. Antimicrob Agents Chemother 54, 3395-401 (2010).
38. Picot, S. et al. A systematic review and meta-analysis of evidence for correlation between molecular markers of parasite resistance and treatment outcome in *falciparum* malaria. Malar J 8, 89 (2009).
39. Price, R. N. et al. Mefloquine resistance in *Plasmodium falciparum* and increased pfmdr1 gene copy number. Lancet 364, 438-47 (2004).
40. Sidhu, A. B. et al. Decreasing pfmdr1 copy number in *Plasmodium falciparum* malaria heightens susceptibility to mefloquine, lumefantrine, halofantrine, quinine, and artemisinin. J Infect Dis 194, 528-35 (2006).
41. Yuan, J. et al. Chemical genomic profiling for antimalarial therapies, response signatures, and molecular targets. Science 333, 724-9 (2011).
42. Amambua-Ngwa, A. et al. Population genomic scan for candidate signatures of balancing selection to guide antigen characterization in malaria parasites. PLoS Genet 8, e1002992 (2012).
43. Adams, J. et al. The kelch repeat superfamily of proteins: propellers of cell function. Trends Cell Biol 10, 17-24 (2000).

44. Prag, S. & Adams, J. C. Molecular phylogeny of the kelch-repeat superfamily reveals an expansion of BTB/kelch proteins in animals. BMC Bioinformatics 4, 42 (2003).
45. Witkowski, B. et al. Reduced artemisinin susceptibility of *Plasmodium falciparum* ring stages in western Cambodia. Antimicrob Agents Chemother 57, 914-23 (2013).
46. B. Padmanabhan et al., Structural basis for defects of Keap1 activity provoked by its point mutations in lung cancer. Mol Cell 21, 689 (2006).
47. L. M. Boyden et al., Mutations in kelch-like 3 and cullin 3 cause hypertension and electrolyte abnormalities. Nature 482, 98 (2012).
48. X. Li, D. Zhang, M. Hannink, L. J. Beamer, Crystal structure of the Kelch domain of human Keap1. J Biol Chem 279, 54750 (2004).
49. K. Itoh et al., Keap1 represses nuclear activation of antioxidant responsive elements by Nrf2 through binding to the amino-terminal Neh2 domain. Genes Dev 13, 76 (1999).
50. D. Zhang, M. Hannink, Distinct cysteine residues in Keap1 are required for Keap1-dependent ubiquitination of Nrf2 and for stabilization of Nrf2 by chemopreventive agents and oxidative stress. Mol Cell Biol 23, 8137 (2003).
51. Z. Bozdech, H. Ginsburg, Antioxidant defense in *Plasmodium falciparum*—data mining of the transcriptome. Malar J 3, 23 (2004).
52. N. K. Nesser, D. O. Peterson, D. K. Hawley, RNA polymerase II subunit Rpb9 is important for transcriptional fidelity in vivo. Proc Natl Acad Sci USA 103, 3268 (2006).
53. H. Kettenberger, K. J. Armache, P. Cramer, Architecture of the RNA polymerase II-TFIIS complex and implications for mRNA cleavage. Cell 114, 347 (2003).
54. D. Dorin-Semblat, A. Sicard, C. Doerig, L. Ranford-Cartwright, C. Doerig, Disruption of the PfPK7 gene impairs schizogony and sporogony in the human malaria parasite *Plasmodium falciparum*. Eukaryot Cell 7, 279 (2008).
55. R. Tewari et al., The systematic functional analysis of *Plasmodium* protein kinases identifies essential regulators of mosquito transmission. Cell Host Microbe 8, 377 (2010).
56. P. J. Rosenthal, J. H. McKerrow, M. Aikawa, H. Nagasawa, J. H. Leech, A malarial cysteine proteinase is necessary for hemoglobin degradation by *Plasmodium falciparum*. J Clin Invest 82, 1560 (1988).
57. P. S. Sijwali et al., *Plasmodium falciparum* cysteine protease falcipain-1 is not essential in erythrocytic stage malaria parasites. Proc Natl Acad Sci USA 101, 8721 (2004).
58. P. S. Sijwali, J. Koo, N. Singh, P. J. Rosenthal, Gene disruptions demonstrate independent roles for the four falcipain cysteine proteases of *Plasmodium falciparum*. Mol Biochem Parasitol 150, 96 (2006).
59. N. Klonis et al., Altered temporal response of malaria parasites determines differential sensitivity to artemisinin. Proc Natl Acad Sci USA 110, 5157 (2013).
60. C. A. Lobo, H. Fujioka, M. Aikawa, N. Kumar, Disruption of the Pfg27 locus by homologous recombination leads to loss of the sexual phenotype in *P. falciparum*. Mol Cell 3, 793 (1999).
61. Olivieri et al., The *Plasmodium falciparum* protein Pfg27 is dispensable for gametocyte and gamete production, but contributes to cell integrity during gametocytogenesis. Mol Microbiol 73, 180 (2009).
62. Sharma, I. Sharma, D. Kogkasuriyachai, N. Kumar, Structure of a gametocyte protein essential for sexual development in *Plasmodium falciparum*. Nat Struct Biol 10, 197 (2003).

EXAMPLES

Example 1. Artemisinin- and Mock-Pressured *P. falciparum* F32 Lineages

The ART-resistant F32-ART5 parasite line was selected by culturing the ART-sensitive F32-Tanzania clone under a dose-escalating regimen of artemisinin for 5 years. The F32-TEM line was obtained by culturing F32-Tanzania in parallel without artemisinin exposure. Reference DNA was extracted from *P. falciparum* lines 3D7, 89F5 Palo Alto Uganda and K1992. The Ring-stage Survival Assay ($RSA^{0-}_{3h}$) was performed as described[13]. Whole-genome sequencing was performed on F32-Tanzania, F32-TEM, F32-ART5 (4 time-points), three reference strains (3D7, 89F5 and K1992) and 21 Cambodian parasite isolates, using an Illumina paired-reads sequencing technology. A set of 1091 clinical *P. falciparum* isolates was collected from patients participating in ACT efficacy studies in 2001-2012. The K13-propeller was amplified using nested PCR. Double-strand sequencing of PCR products was performed by Macrogen, Korea. Sequences were analyzed with MEGA 5 software version 5.10 to identify specific SNP combinations. Data were analyzed with Microsoft Excel and MedCalc version 12 (Mariakerke, Belgium). Differences were considered statistically significant when P values were less than 0.05. Ethical clearances for parasite isolate collections were obtained from the Cambodian National Ethics Committee for Health Research, the Institutional Review Board of the Naval Medical Research Center, the Technical Review Group of the WHO Regional Office for the Western Pacific, and the Institutional Review Board of the National Institute of Allergy and Infectious Diseases.

*Mycoplasma*-free F32-Tanzania parasites were maintained in human type O red blood cells (RBCs) (Etablisssement Frangais du Sang) diluted to 2.5% hematocrit in RPMI-1640 medium (Invitrogen, San Diego, Calif.) supplemented with 5% human serum. Parasite cultures were maintained at 37° C. in an atmosphere of 5% $CO_2$. Parasitemia was checked daily and maintained below 10%. For the selection of ART-resistant parasites, asynchronous cultures were adjusted to 5-7% parasitemia and grown in the presence of escalating doses of artemisinin (from 10 nM to 9 µM) for 24 h for the first 3 years of drug pressure[18]. In the subsequent 2 years, each drug-pressure cycle was done for 48 h with doses ranging from 9 µM to 18 µM. After drug exposure, the medium was discarded and replaced by human serum-supplemented (20%) drug-free medium. Parasitemia was monitored daily until it reached 5%. At that time, drug pressure was reapplied. The parasite line obtained after an effective 5 years of discontinuous ART pressure was named F32-ART5. In parallel, the parental F32-Tanzania line was kept as a control in continuous culture for the same time under the same conditions (i.e. RBCs, serum and media) but without artemisinin treatment. The resulting control line was called F32-TEM.

Example 2. Laboratory-Adapted *P. falciparum* Lines

Reference DNA was extracted from the laboratory-adapted *P. falciparum* lines 3D7 (MR4, Manassas, Va.), 89F5 Palo Alto Uganda (a clone from the Palo Alto line, originating from Uganda in 1978, which displayed high susceptibility to artemether treatment in the Saimiri sciureus experimental host [O. Mercereau-Puijalon, H. Contamin, and J. C. Barale, unpublished data] and K1992, an isolate collected in Pailin in 1992 before the mass deployment of ART in that area (provided by the French National Reference Center of Malaria). Parasite DNA was extracted from frozen blood aliquots (200 µl) using the Mini blood kit (Qiagen, Valencia, Calif.) according to the manufacturer's instructions.

Example 3. Culture-Adapted *P. falciparum* Isolates from Cambodia

Fifty clinical *P. falciparum* isolates from Cambodia (collected in 2010 and 2011) were adapted to in vitro culture as described by Witkowski et al.[45]. Their geographic origin is indicated in Table 8. Parasite clearance rates were not determined for these patient isolates, as they were collected during field trials that did not include such measurements. Parasite DNA was extracted from frozen blood aliquots (200 µl) using the Mini blood kit (Qiagen).

Example 4. Ring-Stage Survival Assay

The Ring-stage Survival Assay (RSA$^{0-3h}$) was carried out as described by Witkowski et al[13] using highly synchronous parasite cultures. In brief, 0-3 h post-invasion ring-stage parasites were exposed to 700 nM DHA [dihydroartemisinin, obtained from WWARN (www.wwarn.org/research/tools/qaqc)] or its solvent DMSO for 6 h, washed and then cultivated for the next 66 h without drug. Survival rates were assessed microscopically by counting in Giemsa-stained thin smears the proportion of viable parasites that developed into second-generation rings or trophozoites with normal morphology.

Example 5. Temporal and Geographical Sample Collection

A set of 941 clinical *P. falciparum* isolates was collected from patients participating in therapeutic efficacy studies of ACTs, conducted as part of the routine antimalarial drug efficacy monitoring of Cambodia's National Malaria Control Program from 2001 to 2012, and from studies conducted by NAMRU-2 (Table 4). Venous blood samples (5 ml) collected in EDTA or ACD were transported to Institut Pasteur du Cambodge in Phnom Penh within 48 h of collection at 4° C. and then kept at −20° C. until DNA extraction. Parasite DNA was extracted from frozen blood aliquots (200 µl) using the Mini blood kit (Qiagen).

Example 6. Measurement of Parasite Clearance Half-Life

Patients with uncomplicated or severe *P. falciparum* malaria and initial parasite density ≥10,000/µl were enrolled in Pursat and Ratanakiri provinces in 2009 and 2010 as described[6, 13] Patients were treated with an ART and their parasite density measured every 6 h from thick blood films until parasitemia was undetectable. The parasite clearance half-life in 163 patients was derived from these parasite counts using WWARN's on-line Parasite Clearance Estimator (http://www.wwarn.org/toolkit/data-management/parasite-clearance-estimator). The study is registered at ClinicalTrials.gov (number NCT00341003).

Example 7. Whole-Genome Sequencing of Parasite DNA

Whole-genome sequencing was performed on F32-Tanzania, F32-TEM, the F32-ART5 lineage (4 time-points), three reference strains (3D7, 89F5 and K1992) and 21 parasite isolates from Cambodia, using an Illumina paired-reads sequencing technology. Illumina library preparation and sequencing followed standard protocols developed by the supplier. Briefly, genomic DNA was sheared by nebulization, and sheared fragments were end-repaired and phosphorylated. Blunt-end fragments were A-tailed, and sequencing adapters were ligated to the fragments. Inserts were sized using Agencourt AMPure XP Beads (±500 bp; Beckman Coulter Genomics, Danvers, Mass.) and enriched using 10 cycles of PCR before library quantification and validation. Hybridization of the library to the flow cell and bridge amplification was performed to generate clusters, and paired-end reads of 100 cycles were collected on a HiSeq 2000 instrument (Illumina, San Diego, Calif.). After sequencing was complete, image analysis, base calling and error estimation were performed using Illumina Analysis Pipeline version 1.7.

Raw sequence files were filtered using Fqquality tool, a read-quality filtering software developed by N. Joly (Biology IT Center, Institut Pasteur, Paris), which enables the trimming of the first and last low-quality bases in reads. The trimmed reads from controlled Fastq files were mapped on a reference genome (*P. falciparum* 3D7) with the Burrows-Wheeler Alignment (BWA), generating a BAM file (a binary file of tab-delimited format SAM). Next, we used Samtools to prepare a pileup file, which was formatted using in-house software to implement the data into the Wholegenome Data Manager (WDM) database (Beghain et al, in preparation). WDM software is designed to compare and/or align partial or whole *P. falciparum* genomes.

Example 8. Sequencing Genes Containing Non-Synonymous SNPs in F32-ART5

PCR amplification of selected genes was performed using the primers listed in Table 1. Two µl of DNA was amplified with 1 µM of each primer, 0.2 mM dNTP (Solis Biodyne, Tartu, Estonia), 3 mM MgCl$_2$ and 2 U Taq DNA polymerase (Solis Biodyne), using the following cycling program: 5 min at 94° C., then 40 cycles of 30 sec at 94° C., 90 sec at 60° C., 90 sec at 72° C. and final extension 10 min at 72° C. PCR products were detected by 2% agarose gel electrophoresis and ethidium bromide staining. Double-strand sequencing of PCR products was performed by Beckman Coulter Genomics, France. Sequences were analyzed with MEGA 5 software version 5.10 in order to identify specific SNP combinations.

Example 9. Sequencing the K13-Propeller Domain

The K13-propeller domain was amplified using the following primers: for the primary PCR (K13-1 5'-cggagtgaccaaatctggga-3' (SEQ ID NO:9) and K13-4 5'-gggaatctggtggtaacagc-3' (SEQ ID NO:10)) and the nested PCR (K13-2 5'-gccaagctgccattcatttg-3' (SEQ ID NO:13) and K13-3 5'-gccttgttgaaagaagcaga-3' (SEQ ID NO:14)). One µl of DNA was amplified with 1 µM of each primer, 0.2 mM dNTP (Solis Biodyne), 3 mM MgCl$_2$ and 2 U Taq DNA polymerase (Solis Biodyne), using the following cycling program: 5 min at 94° C., then 40 cycles of 30 sec at 94° C., 90 sec at 60° C., 90 sec at 72° C. and final extension 10 min at 72° C. For the nested PCR, 2 µl of primary PCR products were amplified under the same conditions, except for the $MgCl_2$ concentration (2.5 mM). PCR products were detected using 2% agarose gel electrophoresis and ethidium bromide staining. Double-strand sequencing of PCR products was performed by Macrogen, Korea. Sequences were analyzed with MEGA 5 software version 5.10 to identify specific SNP combinations.

Example 10. Deep-Sequencing of Clinical Parasite Isolates and Population Structure Analysis DNA extraction, Illumina® sequencing and SNP genotyping of clinical parasite isolates obtained from malaria patients in Pursat and Ratanakiri provinces, Cambodia, have been previously described[15]. Population structure analysis of these parasites identified four subpopulations: KH1, KH2, KH3 and KH4. Parasites with <80% ancestry from any of these four groups were deemed admixed (KHA).

Example 11. Temporal Acquisition of Mutations in the F32-ART5 Lineage

The F32-ART5 lineage was explored by whole-genome sequencing using samples collected at time 0 (original F32-Tanzania clonal line), Day 196 (0.2-µM pressure cycle #23), Day 385 (1.8-µM pressure cycle #39), Day 618 (9-µM pressure cycle #56) and Day 2250 (9-µM pressure cycle #120). The F32-TEM sample was collected on Day 2250. Additional samples collected at the time of the $30^{th}$, $33^{rd}$, $34^{th}$ $36^{th}$, $68^{th}$ and $98^{th}$ pressure cycles were studied by PCR. DNA from parasite cultures was extracted using the High Pure PCR Template Preparation Kit (Roche Diagnostics, Mannheim, Germany) according to the manufacturer's instructions.

The F32-ART5 samples tested in the Ring-stage Survival Assay ($RSA^{0-3h}$) were collected at the time of the $17^{th}$, $48^{th}$ and $122^{nd}$ pressure cycles (0.04, 2.7 and 9 µM ART), respectively. The F32-TEM sample was collected at the last mock pressure cycle. The RSA0-3 h survival rates were determined in triplicate experiments with different batches of red blood cells, and evaluated as above using Giemsa-stained thin smears read by two independent microscopists (B.W. and F. B.-V.). Survival rates were compared using Mann-Whitney U test. The RSA0-3 h survival rates of the F32-ART5 samples were as follows: at drug-pressure cycles: #17 (n=3, median 0%, IQR 0-0.07%), #48 (n=3, median 11.7%, IQR 10.3-14.6; P=0.04 for #17 vs. #48, Mann-Whitney U test) and #122 (n=3, median 12.8%, IQR 10.6-14.5, P=0.04 and P=0.82 for #17 vs. #122 and #48 vs. #122). The $RSA^{0-3h}$ survival rate of the F32-TEM line was also determined in triplicate experiments (n=3, median 0%, IQR 0-0.05, P=0.81 for #TEM vs. #17, Mann-Whitney U test).

Example 12. Prevalence of K13-Propeller Mutations in 886 Clinical Parasite Isolates Collected in Six Cambodian Provinces in 2001-2012

The K13-propeller was genotyped by sequencing PCR products amplified from 886 archived blood samples. The number of samples analyzed from each province each year is indicated in FIG. 3. The Fisher's exact test was used to compare the frequency of isolates harboring a wildtype K13-propeller sequence in each province over time. A significant decrease of the frequency of the wildtype K13-propeller allele was observed in the western provinces during the decade. In Pailin, it decreased from 30.0% in 2001-2002 (12/40) to 4.8% in 2011-2012 (4/84), P=0.0002, Fisher's exact test; Battambang from 71.9% in 2001-2002 (46/64) to 7.0% in 2011-2012 (5/71), P<10-6; Pursat from 50.0% in 2003-2004 (5/10) to 10.5% in 2011-2012 (2/19), P=0.03; and in Kratie from 93.3% in 2001-2002 (14/15) to 29.4% in 2011-2012 (5/17), P=0.0003. Significant decreases in wildtype allele frequency were not observed in Preah Vihear [from 92.6% in 2001-2002 (25/27) to 84.2% in 2011-2012 (16/19), P=0.63]; or Ratanakiri [from 96.4% in 2001-2002 (54/56) to 94.3% in 2011-2012 (33/35), P=0.63]. The frequency of C580Y increased in Pailin from 45.0% (18/40) in 2001-2002 to 88.1% (74/84) in 2011-2012 (P<10-6), and in Battambang from 7.8% (5/64) in 2001-2002 to 87.3% (62/71) in 2011-2012 (P<10-6) indicating its rapid invasion of the population and near fixation in these provinces.

Example 13. 3D-Structure Modeling of the K13-Propeller

The 3D-structural model of the kelch propeller domain of PF3D7_1343700 ('K13-propeller') was obtained by homology modeling satisfying spatial restraints using Modeller v9.11 (Fiser A, Sali A (2003). "Modeller: generation and refinement of homology-based protein structure models". *Meth. Enzymol.* 374: 461-91.). The 295 amino acids composing the K13-propeller are 22%, 25% and 25% identical to the kelch propeller domain of the human Keap1 [Protein Data Bank (PDB) 2FLU], KLHL12 (PDB 2VPJ) and KLHL2 (PDB 2XN4) proteins, respectively, that were used as templates to model the 3D-structure of the K13-propeller. The reliability of the obtained model was assessed using two classical criteria. First, the significance of the sequence alignment between the K13 kelch domain and one template was confirmed by an E-value=0, as calculated by Modeller using the Built-Profile routine. Second, the model achieved a GA341 model score=1 (a score ≥0.7 corresponds to highly reliable models). Localization of the mutants in the K13 3D-model was prepared using the PyMOL Molecular Graphics System, version 1.5.0.4 (Schrödinger, Portland, Oreg.).

Example 14. Statistical Analysis

Data were analyzed with Microsoft Excel and MedCalc version 12 (Mariakerke, Belgium). Quantitative data were expressed as median, interquartile range (IQR). The Mann-Whitney U test (independent samples, two-sided) was used to compare two groups, and the Kruskal-Wallis test (H-test, two-sided) was used to compare more than two groups. The Spearman's rho rank correlation coefficient (and the 95% confidence interval for the correlation coefficient) was used to measure the strength of relationship between the prevalence of wildtype K13-propeller allele and the frequency of day 3 positivity (defined as persistence of microscopically-detectable parasites on the third day of artemisinin-based combination therapy)[2]. Fisher's exact test was used to compare frequency data and the Clopper-Pearson exact method based on the beta distribution was used to determine 95% confidence intervals for proportions. Differences were considered statistically significant when P values were less than 0.05.

Example 15. Additional SNPs

After the first collection of 941 clinical *P. falciparum* from Cambodian patients as described in Example 5, further blood samples from *P. falciparum* infected patients were collected in several African countries as Benin, Angola and Cameroon, and in South America following the same experimental procedure as in Example 5. A total of 9523 blood samples was collected.

| Continent | Country | Total | NI | available | rate |
|---|---|---|---|---|---|
| AFRICA | Benin | 232 | 31 | 201 | 87% |
| AFRICA | Cameroon | 593 | 4 | 589 | 99% |
| AFRICA | Central African Republic | 400 | 46 | 354 | 89% |
| AFRICA | Comoros | 27 | 0 | 27 | 100% |
| AFRICA | Comoros | 309 | 2 | 307 | 99% |
| AFRICA | Democratic Republic of Congo | 92 | 0 | 92 | 100% |
| AFRICA | Democratico Republic of Congo | 924 | 58 | 866 | 94% |
| AFRICA | Ethiopia | 146 | 20 | 126 | 86% |
| AFRICA | Gabon | 153 | 109 | 44 | 29% |
| AFRICA | Gabon | 56 | 7 | 49 | 88% |
| AFRICA | Kenya | 191 | 14 | 177 | 93% |
| AFRICA | Madagascar | 275 | 21 | 254 | 92% |
| AFRICA | Mali | 14 | 0 | 14 | 100% |
| AFRICA | Niger | 602 | 236 | 366 | 61% |
| AFRICA | Niger | 164 | 19 | 145 | 88% |
| AFRICA | Nigeria | 206 | 26 | 180 | 87% |
| AFRICA | Rwanda | 293 | 1 | 292 | 100% |
| AFRICA | Senegal | 108 | 67 | 41 | 38% |
| AFRICA | Senegal | 138 | 0 | 138 | 100% |
| AFRICA | Tanzania | 232 | 0 | 232 | 100% |
| AFRICA | Togo | 476 | 0 | 476 | 100% |
| AFRICA | Uganda | 279 | 11 | 268 | 96% |
| AFRICA | Zambia | 298 | 21 | 277 | 93% |
| ASIA | Bangladesh | 295 | 15 | 280 | 95% |
| ASIA | Cambodia | 882 | 0 | 882 | 100% |
| ASIA | China | 180 | 1 | 179 | 99% |
| ASIA | Indonesia | 110 | 4 | 106 | 96% |
| ASIA | Iran | 78 | 2 | 76 | 97% |
| ASIA | Lao PDR | 75 | 0 | 75 | 100% |
| ASIA | Lao PDR | 47 | 2 | 45 | 96% |
| ASIA | Philippines | 120 | 21 | 99 | 83% |
| ASIA | Thailand | 150 | 2 | 148 | 99% |
| ASIA | Thailand | 57 | 0 | 57 | 100% |
| ASIA | Vietnam | 177 | 1 | 176 | 99% |
| OCEANIA | Papua New Guinea | 55 | 13 | 42 | 76% |
| OCEANIA | Solomon Islands | 44 | 1 | 43 | 98% |
| S. AMERICA | Brazil | 237 | 0 | 237 | 100% |
| S. AMERICA | Colombia | 535 | 12 | 523 | 98% |
| S. AMERICA | French Guiana | 198 | 20 | 178 | 90% |
| S. AMERICA | Peru | 75 | 6 | 69 | 92% |
| | TOTAL | 9523 | 793 | 8730 | |

NI: non interpetable sample

The K13-propeller domain was genotyped by sequencing PCR products amplified from parasite DNA as described in Example 9.

Additional non synonymous SNPs were found in the K13 propeller domain. At the end the inventors identified 27 SNPs listed below:

F446I ttt/att
G449A ggt/gct
N458Y aat/tat
C469Y tgc/tac
W470stop tgg/tga
A481V gct/gtt
Y493H tac/cac
K503N aag/aat
S522C agt/tgt
V534A gtt/gct
R539T aga/aca
I543T att/act
G548D ggc/gac
P553L ccg/ctg
V555A gta/gca
A557S gca/tca
R561H cgt/cat
K563R aaa/aga
V568G gtg/ggg
P574L cct/ctt
A578S gct/tct
C580Y tgt/tat
F583L ttt/tta/g
D584V gat/gtt
V589I gtc/atc
Q613E caa/gaa
D641G gat/ggt

Example 16: Method to Detect Simultaneously all the Mutations in the K13 Propeller Domain (FIG. 13)

This example describes details relating to the method to detect simultaneously all the mutations in the K13 propeller domain (FIG. 13). SNP detection is performed in three steps: hybridization of all probes with amplified DNA (first step); ligation of the conserved probe with allele-specific probe (second step) and reading of the fluorescence issued from biotin and from allele-specific fluorescence (third step)

List of Detected Mutations

F446I ttt/att,
G449A ggt/gct
N458Y aat/tat
C469Y tgc/tac
W470stop tgg/tga
A481V gct/gtt
Y493H tac/cac
K503N aag/aat
S522C agt/tgt
V534A gtt/gct
R539T aga/aca
I543T att/act
G548D ggc/gac
P553L ccg/ctg
V555A gta/gca
A557S gca/tca
R561H cgt/cat
K563R aaa/aga
V568G gtg/ggg
P574L cct/ctt
A578S gct/tct
C580Y tgt/tat
F583L ttt/tta/g
D584V gat/gtt
V589I gtc/atc
Q613E caa/gaa
D641G gat/ggt.

Sequence of the K13 Propeller Domain with all the Mutations

GCCTTGTTGAAAGAAGCAGAATTTTATGGTATTA
AATTTTTACCATTCCCATTAGTATTTTGTATAGGT
GGATTTGATGGTGTAGAATATTTAAATTCGATG-
GAATTATTAGATATTAGTCAACAATGCTGGCTAT
GTGTACACCTATGTCTACCAAAAAAGCTTATTTTG-
GAAGTGCTGTATTGAATAATTTCTTATACGTTTTT
GGTGGTAATAACTATGATTATAAGGCTTTATTT-
GAAACTGAGGTGTATGATCGTTTAAGAGATGTATG

GTATGTTTCAAGTAATT-
TAAATATACCTAGAAGAAATAATTGTGGTGTTACGT-
CAAATGGTAGAATTT ATTGTATTGGGGGATAT-
GATGGCTCTTCTATTATACCGAATGTAGAAGCATAT
GATCATCGTATGAAA
GCATGGGTAGAGGTGGCACCTTTGAATACCCCTA-
GATCATCAGCTATGTGTGTTGCTTTTGATAATAA
AATTTATGTCATTGGTGGAACTAATGGTGAGAGAT-
TAAATTCTATTGAAGTATATGAAGAAAAAATGA
ATAAATGGGAACAATTTCCATATGCCTTATT-
AGAAGCTAGAAGTTCAGGAGCAGCTTTTAAT-
TACCTTA ATCAAATATATGTTGTTGGAGGTATTGA-
TAATGAACATAACATATTAGATTCCGTTGAACAATAT-
CAA
CCATTTAATAAAAGATGGCAAT-
TTCTAAATGGTGTACCAGAGAAAAAAATGAAT-
TTTGGAGCTGCCAC ATTGTCAGATTCTTATATAAT-
TACAGGAGGAGAAAATGGCGAAGTTCTAAATTCA
TGTCATTTCTTTC ACCAGATACAAAT-
GAATGGCAGCTTGGC (nt 1279-2127 of SEQ ID NO:1).

First STEP: PCR amplification of the Sequence of the K13 propeller domain

PCR amplification is performed according to Example 9.
For the primary PCR, primers are:
K13_1_F 5'-CGGAGTGACCAAATCTGGGA-3' (SEQ ID NO:9)
K13_4_R 5'-GGGAATCTGGTGGTAACAGC-3' (SEQ ID NO:10)
For the nested PCR, primers are:
K13_3_F 5'-GCCTTGTTGAAAGAAGCAGA-3' (SEQ ID NO:14)
K13_2_R 5'-GCCAAGCTGCCATTCATTTG-3' (SEQ ID NO:13)

Second STEP: SNPs detection

For each SNP one conserved probe hybridizing with the conserved sequence downstream the position of the mutated nucleotide is used. This probe has a phosphate [Phos] at the 5'extremity to permit ligation and a Biotin tag [BtnTg] at the 3' extremity; for each SNP two allele-specific probes hybridizing with the wildtype codon or the mutant codon were also used. Each of allele-specific probe has a specific fluorescent tag (Tag WT for tag specific for wildtype codon and Tag MT for tag specific for mutant codon).

List of Probes:
F446I ttt/att
[Phos]TTTGTATAGGTGGATTT[BtnTg] (SEQ ID NO:53)
Tag_WT_T CCATTCCCATTAGTAT (SEQ ID NO:54)
Tag_MT_A CCATTCCCATTAGTAA (SEQ ID NO:55)
G449A ggt/gct
[Phos]TGGATTTGATGGTGTAGAA[BtnTg] (SEQ ID NO:56)
Tag_WT_G CATTAGTATTTTGTATAGG (SEQ ID NO:57)
Tag_MT_C CATTAGTATTTTGTATAGC (SEQ ID NO:58)
N458Y aat/tat
[Phos]ATTCGATGGAATTATTAGATATTAGT-
CAACAA[BtnTg] (SEQ ID NO:59)
Tag_WT_A GSTGGATTTGATGGTGTAGAATATT-
TAA (SEQ ID NO:60)
Tag_MT_T GSTGGATTTGATGGTGTAGAATATTTAT (SEQ ID NO:61)
C469Y tgc/tac
[Phos]CTGGCGTATGTGTACAC[BtnTg] (SEQ ID NO:62)
Tag_WT_G ATATTAGTCAACAATG (SEQ ID NO:63)
Tag_MT_A ATATTAGTCAACAATA (SEQ ID NO:64)
W470stop tgg/tga
[Phos]CGTATGTGTACACCTATG[BtnTg] (SEQ ID NO:65)
Tag_WT_G ATTAGTCAACAATGCTGG (SEQ ID NO:66)
Tag_MT_A ATTAGTCAACAATGCTGA (SEQ ID NO:67)
A481V gct/gtt
[Phos]TTATTTTGGAAGTGCTGTA[BtnTg] (SEQ ID NO:68)
Tag_WT_C TATGTCTACCAAAAAAGC (SEQ ID NO:69)
Tag_MT_T TATGTCTACCAAAAAAGT (SEQ ID NO:70)
Y493H tac/cac
[Phos]ACGTTTTTGGTGGTAATAACTATGATT[BtnTg] (SEQ ID NO:71)
Tag_WT_T TGGAAGTGCTGTATTGAATAATTTCT-TAT (SEQ ID NO:72)
Tag_MT_C TGGAAGTGCTGTATTGAATAATTTCT-TAC (SEQ ID NO:73)
S522C agt/tgt
[Phos]GTAATTTAAATATACCTAGA[BtnTg] (SEQ ID NO:74)
Tag_WT_A GATGTATGGTATGTTTCAA (SEQ ID NO:75)
Tag_MT_T GATGTATGGTATGTTTCAT (SEQ ID NO:76)
V534A gtt/gct
[Phos]TACGTCAAATGGTAGAAT[BtnTg] (SEQ ID NO:77)
Tag_WT_T GAAGAAATAATTGTGGTGT (SEQ ID NO:78)
Tag_MT_C GAAGAAATAATTGTGGTGC (SEQ ID NO:79)
R539T aga/aca
[Phos]AATTTATTGTAYTGGGGGATATGATG[BtnTg] (SEQ ID NO:80)
Tag_WT_G TGTGGTGTTACGTCAAWTGGTAG (SEQ ID NO:81)
Tag_MT_C TGTGGTGTTACGTCAAWTGGTAC (SEQ ID NO:82)
I543 aTt/aCt
[Phos]TGGGGGATATGATGGCTCT [BtnTg] (SEQ ID NO:83)
Tag_WT_T TGTTACGTCAAWTGGTASAATTTAT-TGTAT (SEQ ID NO:84)
Tag_MT_C TGTTACGTCAAWTGGTASAATTTAT-TGTAC (SEQ ID NO:85)
G548D ggc/gac
[Phos]CTCTTCTATTATACCGA[BtnTg] (SEQ ID NO:86)
Tag_WT_G ATTGGGGGATATGATGG (SEQ ID NO:87)
Tag_WT_A ATTGGGGGATATGATGA (SEQ ID NO:88)
P553L ccg/ctg
[Phos]GAATGTAGAAGCATATGATCATCRTATG [BtnTg] (SEQ ID NO:89)
Tag_WT_C GGGATATGATGGCTCTTCTATTATACC (SEQ ID NO:90)
Tag_MT_T GGGATATGATGGCTCTTCTATTATACT (SEQ ID NO:91)
V555A gta/gca
[Phos]AGAAGCATATGATCATCG[BtnTg] (SEQ ID NO:92)

Tag_WT_T CTTCTATTATACCGAATGT (SEQ ID NO:93)
Tag_MT_T CTTCTATTATACCGAATGC (SEQ ID NO:94)
A557S gca/tca
[Phos]CATATGATCATCGTATGA[BtnTg] (SEQ ID NO:95)
Tag_WT_G TTATACCGAATGTAGAAG (SEQ ID NO:96)
Tag_MT_T TTATACCGAATGTAGAAT (SEQ ID NO:97)
R561H cgt/cat
[Phos]TATGAAAGCATGGGTAGA[BtnTg] (SEQ ID NO:98)
Tag_WT_G GAAGCATATGATCATCG (SEQ ID NO:99)
Tag_MT_A GAAGCATATGATCATCA (SEQ ID NO:100)
K563R aaa/aga
[Phos]AGCATGGGTAGAGGTGG[BtnTg] (SEQ ID NO:101)
Tag_WT_A CATATGATCATCGTATGAA (SEQ ID NO:102)
Tag_MT_G CATATGATCATCGTATGAG (SEQ ID NO:103)
V568G gtg/ggg
[Phos]GGCACCTTTGAATACCCYTAGAT[BtnTg] (SEQ ID NO:104)
Tag_WT_T CRTATGAAAGCATGGGTAGAGGT (SEQ ID NO:105)
Tag_MT_G CRTATGAAAGCATGGGTAGAGGG (SEQ ID NO:106)
P574L cct/ctt
[Phos]TAGATCATCAGCTATGTG[BtnTg] (SEQ ID NO:107)
Tag_WT_C GCACCTTTGAATACCCC (SEQ ID NO:108)
Tag_MT_T GCACCTTTGAATACCCT (SEQ ID NO:109)
A578S gct/tct
[Phos]CTATGTGTGTTGCTTTT[BtnTg] (SEQ ID NO:110)
Tag_WT_G GACCCCTAGATCATCAG (SEQ ID NO:111)
Tag_MT_T GACCCCTAGATCATCAT (SEQ ID NO:112)
C580Y tgt/tat
[Phos]TGTTGCTTTTGWTAATAAAATTTATGTC[BtnTg] (SEQ ID NO:113)
Tag_WT_G AATACCCYTAGATCATCAGCTATGTG (SEQ ID NO:114)
Tag_MT_A AATACCCYTAGATCATCAGCTATGTA (SEQ ID NO:115)
F583L/F583S/F583Y ttt/ctt/tct/tat
[Phos]TGATAATAAAATTTATGTCATTG[BtnTg] (SEQ ID NO:116)
Tag_WT_T CTATGTGTGTTGCTTT (SEQ ID NO:117)
Tag_MT_C1 CTATGTGTGTTGCTTC (SEQ ID NO:118)
Tag_MT_A CTATGTGTGTTGCTTA (SEQ ID NO:119)
[Phos]HTGATAATAAAATTTATGTCATTG[BtnTg] (SEQ ID NO:120)
Tag_WT_T2 CTATGTGTGTTGCTT (SEQ ID NO:121)
Tag_MT_C2 CTATGTGTGTTGCTC (SEQ ID NO:122)
D584V gat/gtt
[Phos]TAATAAAATTTATGTCATTGG[BtnTg] (SEQ ID NO:123)
Tag_WT_A ATGTGTGTTGCTTTTGA (SEQ ID NO:124)
Tag_MT_T ATGTGTGTTGCTTTTGT (SEQ ID NO:125)
V589I gtc/atc
[Phos]TCATTGGTGGAACTAATGG[BtnTg] (SEQ ID NO:126)
Tag_WT_G GCTTTTGATAATAAAATTTATG (SEQ ID NO:127)
Tag_MT_A GCTTTTGATAATAAAATTTATA (SEQ ID NO:128)
Q613E caa/gaa
[Phos] AATTTCCATATGCCTTAT[BtnTg] (SEQ ID NO:129)
Tag_WT_C AAAATGAATAAATGGGAAC (SEQ ID NO:130)
Tag_MT_G AAAATGAATAAATGGGAAG (SEQ ID NO:131)
D641G gat/ggt.
[Phos] TAATGAACATAACATATTAG[BtnTg] (SEQ ID NO:132)
Tag_WT_A GTTGTTGGAGGTATTGA (SEQ ID NO:133)
Tag_MT_G GTTGTTGGAGGTATTGG (SEQ ID NO:134)

We claim:

1. A kit for detecting a *Plasmodium* infection or for genotyping *Plasmodium*, comprising:
   a probe for detection of at least one non-synonymous SNP within a mutated K-13 propeller nucleic acid that encodes a mutated K13 propeller protein;
   wherein the probe comprises a fluorescent, radioactive or enzymatic label;
   wherein the protein mutation is a difference in an amino acid residue resulting from said non-synonymous SNP; and
   wherein the at least one non-synonymous SNP is selected from:
   G449A ggt/gct,
   N458Y aat/tat,
   A481V gct/gtt,
   Y493H tac/cac,
   R539T aga/aca,
   I543T att/act,
   P553L ccg/ctg,
   R561H cgt/cat,
   V568G gtg/ggg,
   P574L cct/ctt,
   C580Y tgt/tat, and
   D584V gat/gtt.

2. The kit of claim 1, wherein the probe comprises a fluorescent label.

3. The kit of claim 1, wherein the probe comprises an enzymatic label.

4. The kit of claim 1, wherein the probe is from 15 to 30 nucleotides in size.

5. The kit of claim 1, wherein the at least one non-synonymous SNP is selected from:
   Y493H tac/cac,
   R539T aga/aca,
   I543T att/act, and
   C580Y tgt/tat.

6. The kit of claim 5, wherein the kit comprises probes for detection of each of the following non-synonymous SNPs:
   Y493H tac/cac,
   R539T aga/aca,
   I543T att/act, and
   C580Y tgt/tat.

7. The kit of claim 1, wherein the at least one non-synonymous SNP is selected from:
   G449A ggt/gct,
   N458Y aat/tat,
   A481V gct/gtt,
   Y493H tac/cac,
   R539T aga/aca, I543T att/act,
P553L ccg/ctg,
R561H cgt/cat,
V568G gtg/ggg,
P574L cct/ctt,
C580Y tgt/tat, and
D584V gat/gtt.

8. The kit of claim 7, wherein the kit comprises probes for detection of each of the following non-synonymous SNPs:
G449A ggt/gct,
N458Y aat/tat,
A481V gct/gtt,
Y493H tac/cac,
R539T aga/aca,
I543T att/act,
P553L ccg/ctg,
R561H cgt/cat,
V568G gtg/ggg,
P574L cct/ctt,
C580Y tgt/tat, and
D584V gat/gtt.

9. A kit for detecting a *Plasmodium* infection or for genotyping *Plasmodium*, comprising:
a probe for detection of at least one non-synonymous SNP within a mutated K-13 propeller nucleic acid that encodes a mutated K13 propeller protein;
wherein the probe comprises a fluorescent, radioactive or enzymatic label;
wherein the protein mutation is a difference in an amino acid residue resulting from said non-synonymous SNP;
wherein the at least one non-synonymous SNP is selected from:
F446I ttt/att,
C469Y tgc/tac,
W470stop tgg/tga,
K503N aag/aat,
S522C agt/tgt,
V534A gtt/gct,
G548D ggc/gac,
V555A gta/gca,
A557S gca/tca,
K563R aaa/aga,
A578S gct/tct,
F583L ttt/tta/g,
V589I gtc/atc,
Q613E caa/gaa, and
D641G gat/ggt.

10. The kit of claim 9, wherein the kit comprises probes for detection of each of the following non-synonymous SNPs:
F446I ttt/att,
C469Y tgc/tac,
W470stop tgg/tga,
K503N aag/aat,
S522C agt/tgt,
V534A gtt/gct,
G548D ggc/gac,
V555A gta/gca,
A557S gca/tca,
K563R aaa/aga,
A578S gct/tct,
F583L ttt/tta/g,
V589I gtc/atc,
Q613E caa/gaa, and
D641G gat/ggt.

11. The kit of claim 1, wherein the kit further comprises at least one primer for amplifying a fragment of a mutated K-13 propeller nucleic acid, wherein the fragment comprises the at least one non-synonymous SNP.

12. The kit of claim 11, wherein the kit comprises a pair of primers for amplifying a fragment of a mutated K-13 propeller nucleic acid, wherein the fragment comprises the at least one non-synonymous SNP.

13. The kit of claim 12, wherein the fragment is at least 50 nucleotides in size.

14. The kit of claim 12, wherein the fragment is at least 300 nucleotides in size.

* * * * *